United States Patent
Miyoshi et al.

(10) Patent No.: US 12,164,230 B2
(45) Date of Patent: *Dec. 10, 2024

(54) ACTINIC RAY-SENSITIVE OR RADIATION-SENSITIVE RESIN COMPOSITION, ACTINIC RAY-SENSITIVE OR RADIATION-SENSITIVE FILM, PATTERN FORMING METHOD, METHOD FOR MANUFACTURING ELECTRONIC DEVICE, AND COMPOUND

(71) Applicant: FUJIFILM Corporation, Tokyo (JP)

(72) Inventors: Taro Miyoshi, Shizuoka (JP); Yasunori Yonekuta, Shizuoka (JP); Eiji Fukuzaki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 701 days.

This patent is subject to a terminal disclaimer.

(21) Appl. No.: 17/166,321

(22) Filed: Feb. 3, 2021

(65) Prior Publication Data

US 2021/0165325 A1   Jun. 3, 2021

Related U.S. Application Data

(63) Continuation of application No. PCT/JP2019/033802, filed on Aug. 28, 2019.

(30) Foreign Application Priority Data

Aug. 31, 2018 (JP) .................. 2018-164084
Dec. 28, 2018 (JP) .................. 2018-248642
Mar. 14, 2019 (JP) .................. 2019-047394

(51) Int. Cl.
G03F 7/039   (2006.01)
G03F 7/004   (2006.01)
G03F 7/20    (2006.01)

(52) U.S. Cl.
CPC .......... *G03F 7/0392* (2013.01); *G03F 7/0045* (2013.01); *G03F 7/20* (2013.01)

(58) Field of Classification Search
None
See application file for complete search history.

(56) References Cited

U.S. PATENT DOCUMENTS

| | | |
|---|---|---|
| 6,359,180 B1 | 3/2002 | Kumamoto et al. |
| 2002/0107415 A1 | 8/2002 | Kumamoto et al. |
| 2005/0079439 A1* | 4/2005 | Hayakawa ............ G03F 7/0045 430/270.1 |
| 2012/0003585 A1 | 1/2012 | Tsubaki et al. |
| 2012/0094235 A1* | 4/2012 | Tsuchihashi .......... G03F 7/0045 430/296 |
| 2012/0148957 A1* | 6/2012 | Enomoto ................ G03F 7/325 430/285.1 |
| 2013/0202999 A1* | 8/2013 | Iwato ....................... G03F 7/32 430/325 |
| 2015/0355544 A1 | 12/2015 | Fukushima et al. |
| 2016/0090355 A1* | 3/2016 | Domon ................... G03F 7/038 430/296 |
| 2017/0123313 A1* | 5/2017 | Kaur ..................... G03F 7/0397 |
| 2018/0237629 A1 | 8/2018 | Yachi et al. |
| 2023/0038825 A1* | 2/2023 | Ishihara ................ G03F 7/0392 |
| 2023/0075188 A1* | 3/2023 | Miyoshi ................ C08F 212/24 |
| 2023/0120139 A1* | 4/2023 | Miyoshi ................ C08F 212/24 430/270.1 |
| 2023/0148344 A1* | 5/2023 | Goto ..................... G03F 7/0392 430/270.1 |

FOREIGN PATENT DOCUMENTS

| | | | |
|---|---|---|---|
| CN | 107188781 A | * 9/2017 | .......... B01J 31/2252 |
| CN | 108299498 A | 7/2018 | |
| JP | 2000-344733 A | 12/2000 | |
| JP | 2009053518 A | * 3/2009 | |
| JP | 2010-237654 A | 10/2010 | |
| JP | 2015-232598 A | 12/2015 | |
| WO | 2017/033732 A1 | 3/2017 | |

OTHER PUBLICATIONS

International Search Report (PCT/ISA/210) dated Nov. 19, 2019 issued by the International Searching Authority in counterpart International Application No. PCT/JP2019/033802.
Written Opinion (PCT/ISA/237) dated Nov. 19, 2019 issued by the International Searching Authority in counterpart International Application No. PCT/JP2019/033802.
Office Action dated Dec. 13, 2022, issued by the Taiwan Intellectual Property Office in counterpart Taiwanese Patent Application No. 108131331.

* cited by examiner

*Primary Examiner* — Martin J Angebranndt
(74) *Attorney, Agent, or Firm* — Sughrue Mion, PLLC

(57) ABSTRACT

The present invention provides an actinic ray-sensitive or radiation-sensitive resin composition containing (A) a resin having a solubility in an alkali developer that increases through decomposition by an action of an acid and (B) a compound that generates an acid upon irradiation with actinic rays or radiation and is represented by a specific structure; an actinic ray-sensitive or radiation-sensitive film using the composition; a pattern forming method; a method for manufacturing an electronic device; and a compound.

9 Claims, No Drawings

ACTINIC RAY-SENSITIVE OR RADIATION-SENSITIVE RESIN COMPOSITION, ACTINIC RAY-SENSITIVE OR RADIATION-SENSITIVE FILM, PATTERN FORMING METHOD, METHOD FOR MANUFACTURING ELECTRONIC DEVICE, AND COMPOUND

CROSS REFERENCE TO RELATED APPLICATION

This is a continuation of International Application No. PCT/JP2019/033802 filed on Aug. 28, 2019 and claiming priority from Japanese Patent Application No. 2018-164084 filed on Aug. 31, 2018, Japanese Patent Application No. 2018-248642 filed on Dec. 28, 2018, and Japanese Patent Application No. 2019-047394 filed on Mar. 14, 2019, the entire contents of which are incorporated herein by reference.

BACKGROUND OF THE INVENTION

1. Field of the Invention

The present invention relates to an actinic ray-sensitive or radiation-sensitive resin composition, an actinic ray-sensitive or radiation-sensitive film, a pattern forming method, a method for manufacturing an electronic device, and a compound. More specifically, the present invention relates to an actinic ray-sensitive or radiation-sensitive resin composition, an actinic ray-sensitive or radiation-sensitive film, a pattern forming method, a method for manufacturing an electronic device, and a compound, each of which is suitably used for an ultra-microlithography process applicable to a process for manufacturing an ultra-large scale integration (LSI) and a high-capacity microchip, a process for creating a mold for a nanoimprint, a process for manufacturing a high-density information recording medium, and the like, and other photofabrication processes.

2. Description of the Related Art

In processes for manufacturing semiconductor devices such as an integrated circuit (IC) and an LSI, microfabrication by lithography using a photoresist composition has been performed in the related art. In recent years, along with the high integration of integrated circuits, the formation of ultrafine patterns in a submicron region or quarter micron region has been required. Along with this, the exposure wavelength also tends to be shortened from g-line to i-line, and further to KrF excimer laser light, and an exposure machine using an ArF excimer laser having a wavelength of 193 nm as a light source is currently being developed. In addition, the development of a so-called liquid immersion method in which a liquid having a high refractive index (hereinafter also referred to as an "immersion liquid") is filled between a projection lens and a sample as a technique for further enhancing a resolving power has been in progress since the related art.

Furthermore, at present, the development of lithography using electron beams (EB), X-rays, extreme ultraviolet rays (EUV), or the like in addition to excimer laser light is also in progress. Along with this, chemically amplified resist compositions which are effectively sensitive to various radiations and are excellent in a sensitivity and a resolution have been developed.

For example, JP2010-237654A describes an actinic ray-sensitive or radiation-sensitive resin composition containing a resin having a solubility in an alkali developer that increases through decomposition by an action of an acid, and a compound that generates an acid upon irradiation with actinic rays or radiation, and also describes that due to this configuration, it is possible to provide an actinic ray-sensitive or radiation-sensitive resin composition having excellent in characteristics regarding development residues and an out gas.

SUMMARY OF THE INVENTION

However, in recent years, there has been a demand for an actinic ray-sensitive or radiation-sensitive resin composition which can further improve a resolving power and further reduce development defects in a pattern forming method by further miniaturization of a pattern formed.

An object of the present invention is to provide an actinic ray-sensitive or radiation-sensitive resin composition which can attain both an improvement of a resolving power and a reduction in development defects at a high level. Furthermore, another object of the present invention is to provide an actinic ray-sensitive or radiation-sensitive film using the actinic ray-sensitive or radiation-sensitive resin composition, a pattern forming method, a method for manufacturing an electronic device, and a compound.

According to the studies conducted by the present inventors, it was found that the objects can be accomplished by using a compound having an aryl group at the 2- and 6-positions of a benzenesulfonate anion as a compound that generates an acid upon irradiation with actinic rays or radiation in an actinic ray-sensitive or radiation-sensitive resin composition, thereby completing the present invention.

That is, the present inventors have found that the objects can be accomplished by the following configurations.

[1] An actinic ray-sensitive or radiation-sensitive resin composition comprising the following (A) and (B):
(A) a resin having a solubility in an alkali developer that increases through decomposition by an action of an acid; and
(B) a compound that generates an acid upon irradiation with actinic rays or radiation and is represented by General Formula (1).

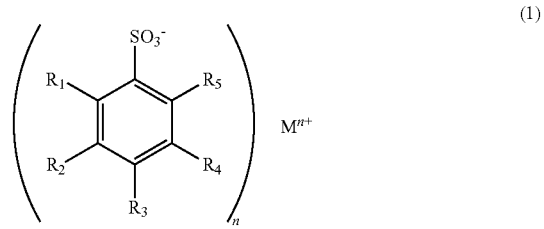

In General Formula (1), $R_1$ and $R_5$ each independently represent an aryl group or a heteroaryl group. $R_2$ to $R_4$ each independently represent a hydrogen atom or a substituent. $M^{n+}$ represents a cation. n represents an integer of 1 or more.

[2] The actinic ray-sensitive or radiation-sensitive resin composition as described in [1],
in which in General Formula (1), $R_3$ represents an aryl group.

[3] The actinic ray-sensitive or radiation-sensitive resin composition as described in [1] or [2], in which in General Formula (1), at least one of $R_1, \ldots,$ or $R_5$ is a group including a polar group, a group including a group having a polarity that increases through decomposition by an action of an acid, or a group including a group having a solubility in an alkali developer that increases through decomposition by an action of an alkali developer.

[4] The actinic ray-sensitive or radiation-sensitive resin composition as described in any one of [1] to [3],
in which in General Formula (1), $R_1$, $R_3$, and $R_5$ are each a group represented by General Formula (Ar).

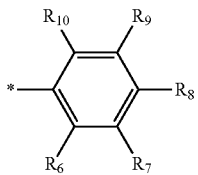

(Ar)

In General Formula (Ar), $R_6$ to $R_{10}$ each independently represent a hydrogen atom or a substituent. At least one of $R_6, \ldots,$ or $R_{10}$ is a group including a polar group, a group including a group having a polarity that increases through decomposition by an action of an acid, or a group including a group having a solubility in an alkali developer that increases through decomposition by an action of an alkali developer. * represents a bond to a benzene ring in General Formula (1).

[5] The actinic ray-sensitive or radiation-sensitive resin composition as described in any one of [1] to [3],
in which in General Formula (1), $R_1$, $R_3$, and $R_5$ are each a group represented by General Formula (Ar1).

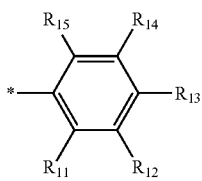

(Ar1)

In General Formula (Ar1),
$R_{11}$ to $R_{15}$ each independently represent a hydrogen atom or a substituent, and at least one of $R_{11}, \ldots,$ or $R_{15}$ represents the following substituent Y. * represents a bond to a benzene ring in General Formula (1).

Substituent Y: a hydroxyl group, a carboxyl group, a group having a carbonyl bond, an acyloxy group, an alkoxycarbonyloxy group, an aryloxycarbonyloxy group, an aryloxycarbonyl group, an alkoxycarbonyl group, a carbamoyl group, or an imido group.

[6] The actinic ray-sensitive or radiation-sensitive resin composition as described in any one of [1] to [5],
in which a pKa of an acid generated from the compound (B) upon irradiation with actinic rays or radiation is from −10 to 5.

[7] An actinic ray-sensitive or radiation-sensitive film formed of the actinic ray-sensitive or radiation-sensitive resin composition as described in any one of [1] to [6].

[8] A pattern forming method comprising:
a resist film forming step of forming a resist film using the actinic ray-sensitive or radiation-sensitive resin composition as described in any one of [1] to [6];
an exposing step of exposing the resist film; and
a developing step of developing the exposed resist film using a developer.

[9] A method for manufacturing an electronic device, comprising the pattern forming method as described in [8].

[10] A compound represented by General Formula (1).

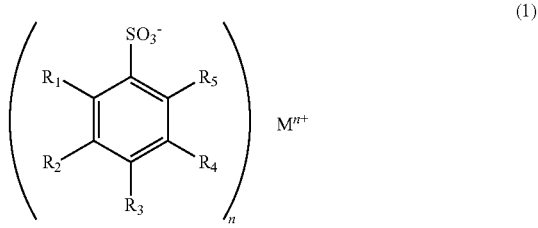

(1)

In General Formula (1),
$R_1$, $R_3$, and $R_5$ each represent a group represented by General Formula (Ar).
$R_2$ and $R_4$ each independently represent a hydrogen atom or a substituent.
$M^{n+}$ represents a cation. n represents an integer of 1 or more.

(Ar)

In General Formula (Ar), $R_6$ to $R_{10}$ each independently represent a hydrogen atom or a substituent. At least one of $R_6, \ldots,$ or $R_{10}$ is a group including a polar group, a group including a group having a polarity that increases through decomposition by an action of an acid, or a group including a group having a solubility in an alkali developer that increases through decomposition by an action of an alkali developer. * represents a bond to a benzene ring in General Formula (1).

According to the present invention, it is possible to provide an actinic ray-sensitive or radiation-sensitive resin composition which can attain both an improvement of a resolving power and a reduction in development defects at a high level. According to the present invention, it is possible to provide an actinic ray-sensitive or radiation-sensitive film using the actinic ray-sensitive or radiation-sensitive resin composition, a pattern forming method, a method for manufacturing an electronic device, and a compound.

DESCRIPTION OF THE PREFERRED EMBODIMENTS

Hereinafter, the present invention will be described in detail.

Description of configuration requirements described below is made on the basis of representative embodiments of the present invention in some cases, but the present invention is not limited to such embodiments.

"Actinic rays" or "radiation" in the present specification means, for example, a bright line spectrum of a mercury lamp, far ultraviolet rays typified by an excimer laser, extreme ultraviolet rays (EUV light), X-rays, soft X-rays, electron beams (EB), or the like. "Light" in the present specification means actinic rays or radiation. Unless otherwise specified, "exposure" in the present specification encompasses not only exposure by a bright line spectrum of a mercury lamp, far ultraviolet rays typified by an excimer laser, extreme ultraviolet rays, X-rays, EUV, or the like, but also lithography by particle rays such as electron beams and ion beams.

In the present specification, a numerical range expressed using "to" is used in a meaning of a range that includes the preceding and succeeding numerical values of "to" as the lower limit value and the upper limit value, respectively.

In the present specification, (meth)acrylate represents at least one of acrylate or methacrylate. In addition, (meth) acrylic acid represents at least one of acrylic acid or methacrylic acid.

In the present specification, the weight-average molecular weight (Mw), the number-average molecular weight (Mn), and the dispersity (also referred to as a molecular weight distribution) (Mw/Mn) of a resin are each defined as a value converted in terms of polystyrene by means of gel permeation chromatography (GPC) measurement (solvent: tetrahydrofuran, flow amount (amount of a sample injected): 10 μL, columns: TSK gel Multipore HXL-M manufactured by Tosoh Corporation, column temperature: 40° C., flow rate: 1.0 mL/min, detector: differential refractive index detector) using a GPC apparatus (HLC-8120 GPC manufactured by Tosoh Corporation).

In citations for a group (atomic group) in the present specification, in a case where the group is cited without specifying whether it is substituted or unsubstituted, the group includes both a group having no substituent and a group having a substituent. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

The actinic ray-sensitive or radiation-sensitive resin composition according to an embodiment of the present invention (hereinafter also referred to as "the composition of the embodiment of the present invention") is an actinic ray-sensitive or radiation-sensitive resin composition containing the following (A) and (B).

(A) A resin having a solubility in an alkali developer that increases through decomposition by an action of an acid.
(B) A compound that generates an acid upon irradiation with actinic rays or radiation and is represented by General Formula (1).

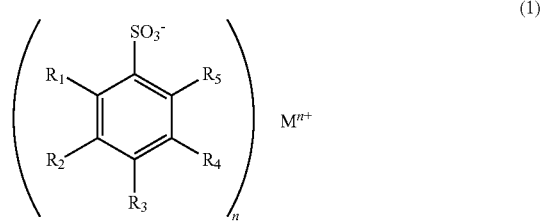

(1)

In General Formula (1), $R_1$ and $R_5$ each independently represent an aryl group or a heteroaryl group. $R_2$ to $R_4$ each independently represent a hydrogen atom or a substituent. $M^{n+}$ represents a cation. n represents an integer of 1 or more.

The composition of the embodiment of the present invention is preferably a resist composition, and may be either a positive tone resist composition or a negative tone resist composition. In addition, the composition may be either a resist composition for alkali development or a resist composition for organic solvent development. Among those, the positive tone resist composition, which is a resist composition for alkali development, is preferable.

Furthermore, the composition of the embodiment of the present invention is preferably a chemically amplified resist composition, and more preferably a chemically amplified positive tone resist composition.

[(A) Resin has Solubility in Alkali Developer that Increases Through Decomposition by Action of Acid]

(A) A resin having a solubility in an alkali developer that increases through decomposition by an action of an acid (also referred to as a "resin (A)") will be described.

Examples of the resin (A) include a resin (hereinafter also referred to as an "acid-decomposable resin") having a group having a polarity that increases through decomposition by an action of an acid (hereinafter also referred to as an "acid-decomposable group").

Since the acid-decomposable resin has the acid-decomposable group, it has a solubility in an alkali developer that increases through decomposition by an action of an acid.

The resin (A) preferably has a repeating unit having an acid-decomposable group.

As the resin (A), a known resin can be appropriately used. For example, the known resins disclosed in paragraphs [0055] to [0191] of the specification of US2016/0274458A1, paragraphs [0035] to [0085] of the specification of US2015/0004544A1, or paragraphs [0045] to [0090] of the specification of US2016/0147150A1 can be suitably used as the resin (A).

The acid-decomposable group preferably has a structure in which a polar group is protected with a group that is eliminated through decomposition by an action of an acid (eliminable group).

Examples of the polar group include an acidic group (typically a group which dissociates in a 2.38%-by-mass aqueous tetramethylammonium hydroxide solution), such as a carboxyl group, a phenolic hydroxyl group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol group (for example, a hexafluoroisopropanol group) having the α-position substituted with an electron-withdrawing group such as a fluorine atom is excluded as a hydroxyl group. The alcoholic hydroxyl group is preferably a hydroxyl group having an acid dissociation constant (pKa) from 12 to 20.

Among those, as the polar group, the carboxyl group, the phenolic hydroxyl group, the fluorinated alcohol group (preferably the hexafluoroisopropanol group), or the sulfonic acid group is preferable.

Examples of the group that is eliminated through decomposition by an action of an acid (eliminable group) include groups represented by Formulae (Y1) to (Y4).

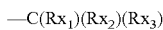  Formula (Y1):

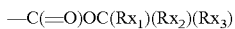  Formula (Y2):

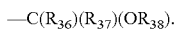  Formula (Y3):

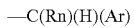  Formula (Y4):

In Formula (Y1) and Formula (Y2), $Rx_1$ to $Rx_3$ each independently represent an (linear or branched) alkyl group or a (monocyclic or polycyclic) cycloalkyl group. Furthermore, in a case where all of $Rx_1$ to $Rx_3$ are (linear or branched) alkyl groups, it is preferable that at least two of $Rx_1$, $Rx_2$, or $Rx_3$ are methyl groups.

Among those, it is preferable that $Rx_1$ to $Rx_3$ each independently represent a linear or branched alkyl group, and it is more preferable that $Rx_1$ to $Rx_3$ each independently represent a linear alkyl group.

Two of $Rx_1$ to $Rx_3$ may be bonded to each other to form a monocycle or polycycle.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group, and a polycyclic cycloalkyl group such as a norbornyl group, a tetracyclodecanyl group, a tetracyclododecanyl group, and an adamantyl group are preferable, and a monocyclic cycloalkyl group having 5 or 6 carbon atoms is more preferable.

In the cycloalkyl group formed by the bonding of two of $Rx_1$ to $Rx_3$, for example, one of the methylene groups constituting the ring may be substituted with a heteroatom such as an oxygen atom or a group having a heteroatom, such as a carbonyl group.

With regard to the group represented by Formula (Y1) or Formula (Y2), for example, an aspect in which $Rx_1$ is a methyl group or an ethyl group, and $Rx_2$ and $Rx_3$ are bonded to each other to form a cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. It is also preferable that $R_{36}$ is the hydrogen atom.

As Formula (Y3), a group represented by Formula (Y3-1) is preferable.

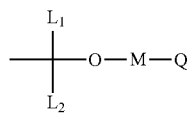  (Y3-1)

Here, $L_1$ and $L_2$ each independently represent a hydrogen atom, an alkyl group, a cycloalkyl group, an aryl group, or a group formed by combination thereof (for example, a group formed by a combination of an alkyl group and an aryl group).

M represents a single bond or a divalent linking group.

Q represents an alkyl group which may include a heteroatom, a cycloalkyl group which may include a heteroatom, an aryl group which may include a heteroatom, an amino group, an ammonium group, a mercapto group, a cyano group, an aldehyde group, or a group formed by combination thereof (for example, a group formed by a combination of an alkyl group and a cycloalkyl group).

In the alkyl group and the cycloalkyl group, for example, one of the methylene groups may be substituted with a heteroatom such as an oxygen atom or a group having a heteroatom, such as a carbonyl group.

In addition, it is preferable that one of $L_1$ or $L_2$ is a hydrogen atom, and the other is an alkyl group, a cycloalkyl group, an aryl group, or a group formed by a combination of an alkylene group and an aryl group.

At least two of Q, M, or $L_1$ may be bonded to each other to form a ring (preferably a 5-membered or 6-membered ring).

From the viewpoint of pattern miniaturization, $L_2$ is preferably a secondary or tertiary alkyl group, and more preferably the tertiary alkyl group. Examples of the secondary alkyl group include an isopropyl group, a cyclohexyl group, and a norbornyl group, and examples of the tertiary alkyl group include a tert-butyl group and an adamantane group. In these aspects, since the glass transition temperature (Tg) and the activation energy are higher, it is possible to suppress fogging in addition to ensuring film hardness.

In Formula (Y4), Ar represents an aromatic ring group. Rn represents an alkyl group, a cycloalkyl group, or an aryl group. Rn and Ar may be bonded to each other to form a non-aromatic ring. Ar is more preferably an aryl group.

The resin (A) preferably has an acetal structure.

The acid-decomposable group preferably has an acetal structure. The acetal structure is, for example, a structure in which a polar group such as a carboxyl group, a phenolic hydroxyl group, and a fluorinated alcohol group is protected with the group represented by Formula (Y3).

As the repeating unit having an acid-decomposable group, a repeating unit represented by Formula (A) is preferable.

  (A)

$L_1$ represents a divalent linking group, $R_1$ to $R_3$ each independently represent a hydrogen atom or a monovalent substituent, and $R_4$ represents a group that is eliminated through decomposition by an action of an acid.

$L_1$ represents a divalent linking group. Examples of the divalent linking group include —CO—, —O—, —S—, —SO—, —SO$_2$—, a hydrocarbon group (for example, an alkylene group, a cycloalkylene group, an alkenylene group, and an arylene group), and a linking group in which a plurality of these groups are linked. Among those, Lt is preferably —CO— or the arylene group.

The arylene group is preferably a phenylene group.

The alkylene group may be linear or branched. The number of carbon atoms of the alkylene group is not particularly limited, but is preferably 1 to 10, more preferably 1 to 3.

$R_1$ to $R_3$ each independently represent a hydrogen atom or a monovalent substituent. Examples of the monovalent substituent include an alkyl group, a cycloalkyl group, and a halogen atom.

The alkyl group may be linear or branched. The number of carbon atoms of the alkyl group is not particularly limited, but is preferably 1 to 10, and more preferably 1 to 3.

The cycloalkyl group may be monocyclic or polycyclic. This cycloalkyl group preferably has 3 to 8 carbon atoms.

Examples of the halogen atom include a fluorine atom, a chlorine atom, a bromine atom, and an iodine atom.

$R_4$ represents a group that is eliminated through decomposition by an action of an acid (eliminable group).

Among those, examples of the eliminable group include the groups represented by Formulae (Y1) to (Y4), and the group represented by Formula (Y3) is preferable.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The substituent preferably has 8 or less carbon atoms.

As the repeating unit having an acid-decomposable group, a repeating unit represented by General Formula (AI) is also preferable.

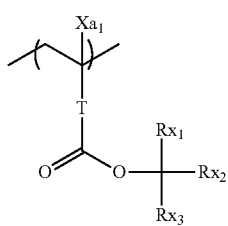

(AI)

In General Formula (AI), $Xa_1$ represents a hydrogen atom or an alkyl group.

T represents a single bond or a divalent linking group.

$Rx_1$ to $Rx_3$ each independently represent an (linear or branched) alkyl group or a (monocyclic or polycyclic) cycloalkyl group. It should be noted that in a case where all of $Rx_1$ to $Rx_3$ are (linear or branched) alkyl groups, at least two of $Rx_1$, $Rx_2$, or $Rx_3$ are preferably methyl groups.

Two of $Rx_1$ to $Rx_3$ may be bonded to each other to form a (monocyclic or polycyclic) cycloalkyl group.

Examples of the alkyl group represented by $Xa_1$ include a methyl group and a group represented by $-CH_2-R_{11}$. $R_{11}$ represents a halogen atom (a fluorine atom or the like), a hydroxyl group, or a monovalent organic group, examples thereof include an alkyl group having 5 or less carbon atoms and an acyl group having 5 or less carbon atoms, the alkyl group having 3 or less carbon atoms is preferable, and a methyl group is more preferable. $Xa_1$ is preferably a hydrogen atom, a methyl group, a trifluoromethyl group, or a hydroxymethyl group.

Examples of the divalent linking group of T include an alkylene group, an aromatic ring group, a —COO-Rt- group, and an —O-Rt- group. In Formulae, Rt represents an alkylene group or a cycloalkylene group.

T is preferably the single bond or the —COO-Rt- group. In a case where T represents the —COO-Rt- group, Rt is preferably an alkylene group having 1 to 5 carbon atoms, and is more preferably a $-CH_2-$ group, a $-(CH_2)_2-$ group, or a $-(CH_2)_3-$ group.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group is preferable, and in addition, a polycyclic cycloalkyl group such as a norbornyl group, a tetracyclodecanyl group, a tetracyclododecanyl group, and an adamantyl group is preferable. Among those, a monocyclic cycloalkyl group having 5 or 6 carbon atoms is preferable.

In the cycloalkyl group formed by the bonding of two of $Rx_1$ to $Rx_3$, for example, one of the methylene groups constituting the ring may be substituted with a heteroatom such as an oxygen atom or a group having a heteroatom, such as a carbonyl group.

With regard to the repeating unit represented by General Formula (AI), for example, an aspect in which $Rx_1$ is a methyl group or an ethyl group, and $Rx_2$ and $Rx_3$ are bonded to each other to form the above-mentioned cycloalkyl group is preferable.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The substituent preferably has 8 or less carbon atoms.

The repeating unit represented by General Formula (AI) is preferably an acid-decomposable tertiary alkyl (meth) acrylate ester-based repeating unit (the repeating unit in which $Xa_1$ represents a hydrogen atom or a methyl group, and T represents a single bond).

The resin (A) may include only one kind of the repeating units having an acid-decomposable group or a combination of two or more kinds of the repeating units.

The content of the repeating unit having an acid-decomposable group included in the resin (A) (in a case where a plurality of the repeating units having an acid-decomposable group are present, a total content thereof) is preferably 10% to 90% by mole, more preferably 20% to 80% by mole, and still more preferably 30% to 70% by mole, with respect to all the repeating units of the resin (A).

(Repeating Unit Having Lactone Group or Sultone Group)

The resin (A) may further have a repeating unit having a lactone group or a sultone group.

As the lactone group or the sultone group, any of groups having a lactone structure or a sultone structure can be used, but a group having a 5- to 7-membered ring lactone structure or a 5- to 7-membered ring sultone structure is preferable; and the group in which another ring structure is fused to the 5- to 7-membered ring lactone structure so as to form a bicyclo structure or a spiro structure, or the group in which another ring structure is fused to the 5- to 7-membered ring sultone structure so as to form a bicyclo structure or a spiro structure is more preferable. The resin (A) more preferably has a repeating unit having a group having lactone structure represented by any of General Formulae (LC1-1) to (LC1-21) or a group having a sultone structure represented by any of General Formula (SL1-1), (SL1-2), or (SL1-3). Further, a group having a lactone structure or a sultone structure may be bonded directly to the main chain. As the preferred structure, groups represented by General Formula (LC1-1), General Formula (LC1-4), General Formula (LC1-5), General Formula (LC1-6), General Formula (LC1-13), and General Formula (LC1-14) are preferable.

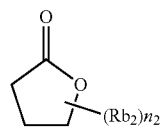

LC1-1

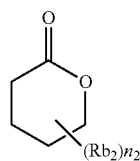

LC1-2

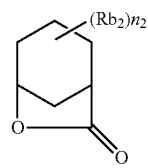

LC1-3

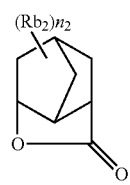

LC1-4

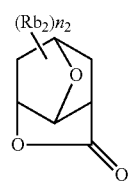

LC1-5

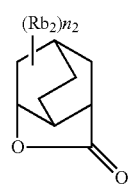

LC1-6

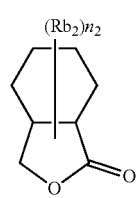

LC1-7

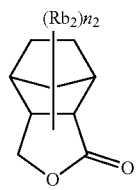

LC1-8

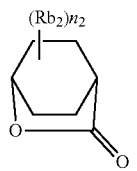

LC1-9

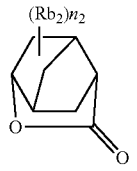

LC1-10

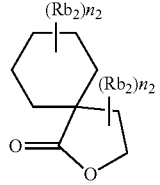

LC1-11

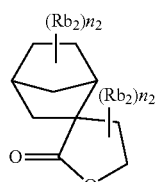

LC1-12

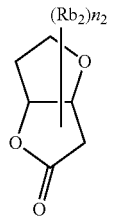

LC1-13

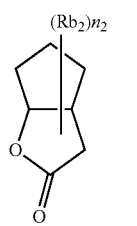

LC1-14

LC1-15

LC1-16

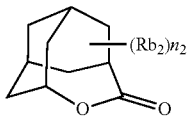

LC1-17

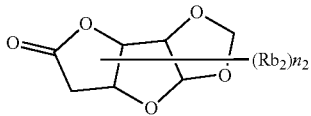

LC1-18

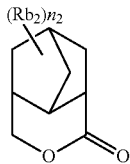

LC1-19

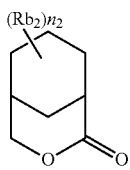

LC1-20

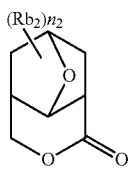

LC1-21

SL1-1

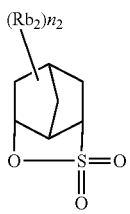

SL1-2

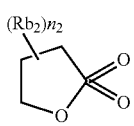

SL1-3

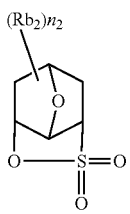

The lactone structural moiety or the sultone structural moiety may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, and an acid-decomposable group. n2 represents an integer of 0 to 4. In a case where n2 is 2 or more, $Rb_2$'s which are present in a plural number may be different from each other and $Rb_2$'s which are present in a plural number may be bonded to each other to form a ring.

Examples of the repeating unit having the group having a lactone structure or a sultone structure include a repeating unit represented by General Formula (AI).

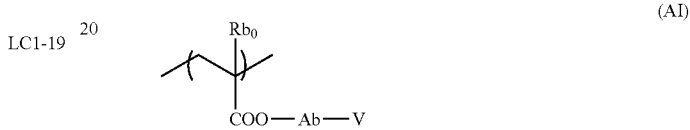

In General Formula (AI), $Rb_0$ represents a hydrogen atom, a halogen atom, or an alkyl group having 1 to 4 carbon atoms.

Preferred examples of the substituent which may be contained in the alkyl group of $Rb_0$ include a hydroxyl group and a halogen atom.

Examples of the halogen atom of $Rb_0$ include a fluorine atom, a chlorine atom, a bromine atom, and an iodine atom. $Rb_0$ is preferably the hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent group formed by combination thereof. Among those, the single bond or a linking group represented by -Ab-$CO_2$— is preferable. Abi is a linear or branched alkylene group or a monocyclic or polycyclic cycloalkylene group, and preferably a methylene group, an ethylene group, a cyclohexylene group, an adamantylene group, or a norbornylene group.

V represents a group having a lactone structure or a sultone structure.

As the group having the lactone structure or the sultone structure of V, a group represented by any of General Formulae (LC1-1) to (LC1-21) and General Formulae (SL1-1) to (SL1-3) is preferable.

The repeating unit having the group having a lactone structure or a sultone structure usually has optical isomers, and any of optical isomers may be used. In addition, one kind of optical isomers may be used singly or a plurality of kinds of optical isomers may be mixed and used. In a case where one kind of optical isomers is mainly used, an optical purity (ee) thereof is preferably 90 or more, and more preferably 95 or more.

Specific examples of the repeating unit having the group having a lactone structure or a sultone structure are shown below, but the present invention is not limited thereto. In the formulae, Rx represents H, $CH_3$, $CH_2OH$, or $CF_3$.

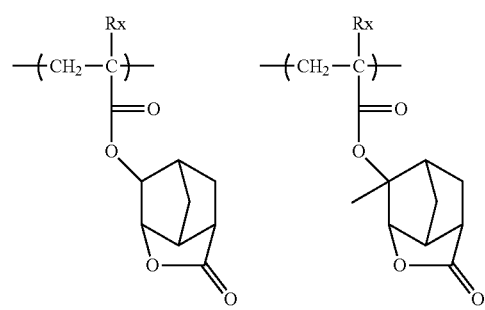
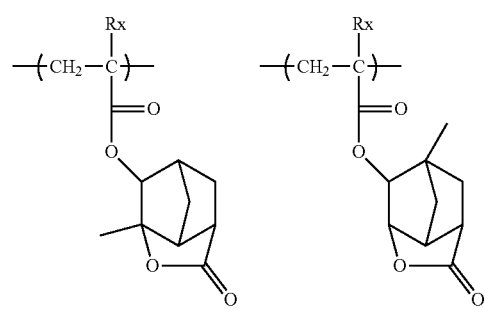
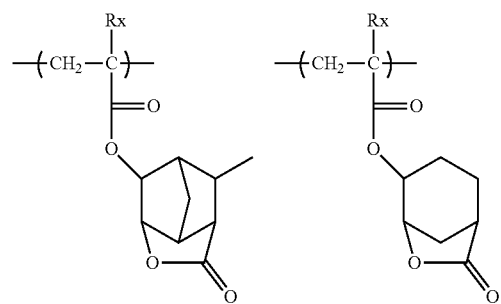
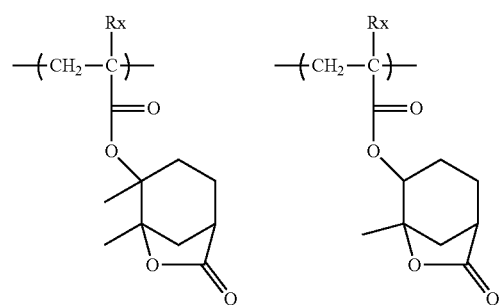
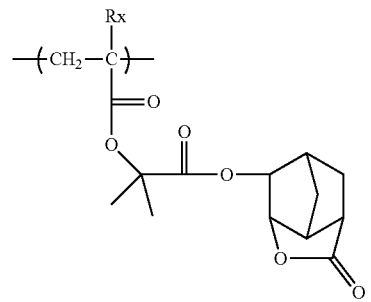
-continued
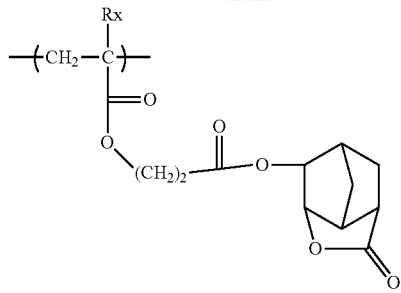
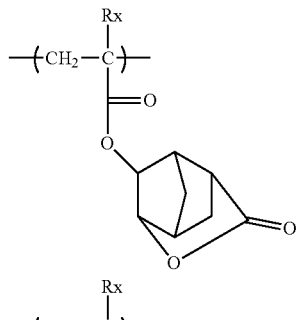
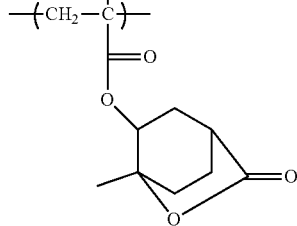
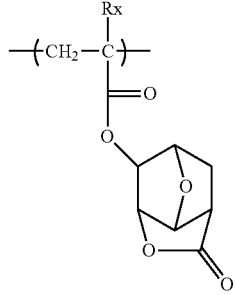
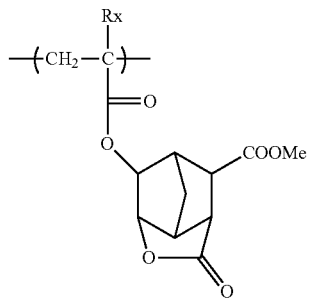
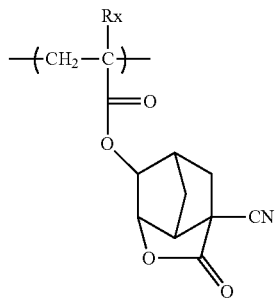

-continued

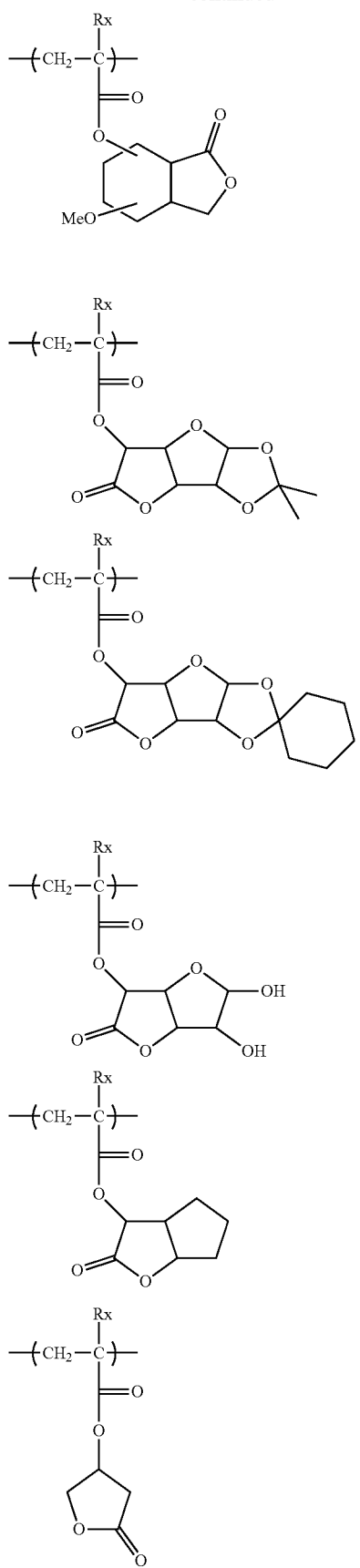

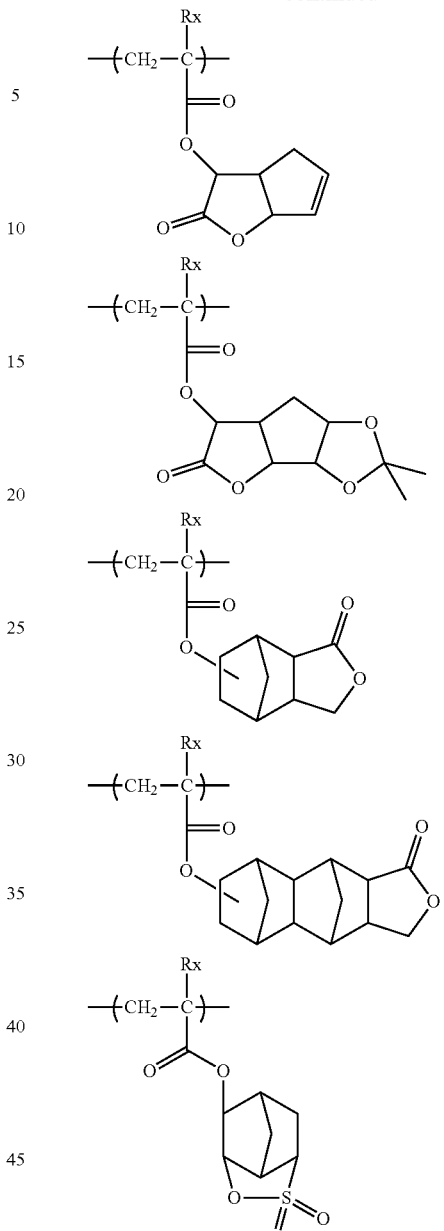

The content of the repeating unit having a lactone group or a sultone group is preferably 1% to 60% by mole, more preferably 5% to 50% by mole, and still more preferably 10% to 40% by mole, with respect to all the repeating units in the resin (A).

(Repeating Unit Having Acid Group)

The resin (A) may have a repeating unit having an acid group.

As the acid group, an acid group having an acid dissociation constant (pKa) of 13 or less is preferable.

The pKa is the same as the pKa in the pKa of an acid generated by the compound (B) which will be described later, upon irradiation with actinic rays or radiation.

As the repeating unit having an acid group, a repeating unit represented by Formula (B) is preferable.

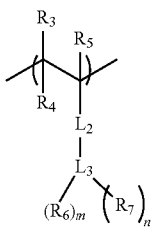
(B)

$R_3$ represents a hydrogen atom or a monovalent organic group.

As the monovalent organic group, a group represented by -$L_4$-$R_8$ is preferable. $L_4$ represents a single bond or an ester group. Examples of $R_8$ include an alkyl group, a cycloalkyl group, an aryl group, and a group formed by combination thereof.

$R_4$ and $R_5$ each independently represent a hydrogen atom, a halogen atom, or an alkyl group.

Examples of the halogen atom include a fluorine atom, a chlorine atom, a bromine atom, or an iodine atom.

$L_2$ represents a single bond or an ester group.

$L_3$ represents an (n+m+1)-valent aromatic hydrocarbon ring group or an (n+m+1)-valent alicyclic hydrocarbon ring group. Examples of the aromatic hydrocarbon ring group include a benzene ring group and a naphthalene ring group. The alicyclic hydrocarbon ring group may be either a monocycle or a polycycle, and examples thereof include a cycloalkyl ring group.

$R_6$ represents a hydroxyl group or a fluorinated alcohol group (preferably a hexafluoroisopropanol group). In addition, in a case where $R_6$ is a hydroxyl group, $L_3$ is preferably the (n+m+1)-valent aromatic hydrocarbon ring group.

$R_7$ represents a halogen atom. Examples of the halogen atom include a fluorine atom, a chlorine atom, a bromine atom, or an iodine atom.

m represents an integer of 1 or more. m is preferably an integer of 1 to 3 and more preferably an integer of 1 or 2.

n represents 0 or an integer of 1 or more. n is preferably an integer of 1 to 4.

In addition, (n+m+1) is preferably an integer of 1 to 5.

As the repeating unit having an acid group, a repeating unit represented by General Formula (I) is also preferable.

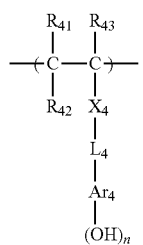
(I)

In General Formula (I), $R_{41}$, $R_{42}$, and $R_{43}$ each independently represent a hydrogen atom, an alkyl group, a cycloalkyl group, a halogen atom, a cyano group, or an alkoxycarbonyl group. It should be noted that $R_{42}$ may be bonded to Ara to form a ring, in which case $R_{42}$ represents a single bond or an alkylene group.

$X_4$ represents a single bond, —COO—, or —CONR$_{64}$—, and $R_{64}$ represents a hydrogen atom or an alkyl group.

$L_4$ represents a single bond or an alkylene group.

$Ar_4$ represents an (n+1)-valent aromatic ring group, and in a case where Ar4 is bonded to $R_{42}$ to form a ring, Ar4 represents an (n+2)-valent aromatic ring group.

n represents an integer of 1 to 5.

As the alkyl group represented by each of Rai, $R_{42}$, and $R_{43}$ in General Formula (I), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group is preferable, an alkyl group having 8 or less carbon atoms is more preferable, and an alkyl group having 3 or less carbon atoms is still more preferable.

The cycloalkyl group of each of $R_{41}$, $R_{42}$, and $R_{43}$ in General Formula (I) may be monocyclic or polycyclic. Among those, a cycloalkyl group having 3 to 8 carbon atoms, such as a cyclopropyl group, a cyclopentyl group, and a monocyclic cyclohexyl group, is preferable.

Examples of the halogen atom of each of $R_{41}$, $R_{42}$, and $R_{43}$ in General Formula (I) include a fluorine atom, a chlorine atom, a bromine atom, and an iodine atom, and the fluorine atom is preferable.

As the alkyl group included in the alkoxycarbonyl group of each of $R_{41}$, $R_{42}$, and $R_{43}$ in General Formula (I), the same ones as the alkyl group in each of $R_{41}$, $R_{42}$, and $R_{43}$ are preferable.

Preferred examples of the substituent in each of the groups include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The substituent preferably has 8 or less carbon atoms.

$Ar_4$ represents an (n+1)-valent aromatic ring group. The divalent aromatic ring group in a case where n is 1 may have a substituent, and is preferably, for example, an arylene group having 6 to 18 carbon atoms, such as a phenylene group, a tolylene group, a naphthylene group, and an anthracenylene group, or an aromatic ring group including a heterocycle such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring.

Specific examples of the (n+1)-valent aromatic ring group in a case where n is an integer of 2 or more include groups formed by removing any (n−1) hydrogen atoms from the above-described specific examples of the divalent aromatic ring group.

The (n+1)-valent aromatic ring group may further have a substituent.

Examples of the substituent which can be contained in the alkyl group, the cycloalkyl group, the alkoxycarbonyl group, the alkylene group, and the (n+1)-valent aromatic ring group as mentioned above include the alkyl group; the alkoxy group such as a methoxy group, an ethoxy group, a hydroxyethoxy group, a propoxy group, a hydroxypropoxy group, and a butoxy group; an aryl group such as a phenyl group; and the like, as mentioned for each of $R_{41}$, $R_{42}$, and $R_{43}$ in General Formula (I).

Examples of the alkyl group of $R_{64}$ in —CONR$_{64}$— represented by $X_4$ ($R_{64}$ represents a hydrogen atom or an alkyl group) include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, and an alkyl group having 8 or less carbon atoms is preferable.

As $X_4$, the single bond, —COO—, or —CONH— is preferable, and the single bond or —COO— is more preferable.

As the alkylene group in $L_4$, an alkylene group having 1 to 8 carbon atoms, such as a methylene group, an ethylene group, a propylene group, a butylene group, a hexylene group, and an octylene group, is preferable.

As $Ar_4$, an aromatic ring group having 6 to 18 carbon atoms is preferable, and a benzene ring group, a naphthalene ring group, and a biphenylene ring group are more preferable.

The repeating unit represented by General Formula (I) preferably has a hydroxystyrene structure. That is, $Ar_4$ is preferably the benzene ring group.

The repeating unit represented by General Formula (I) is preferably a repeating unit represented by General Formula (1).

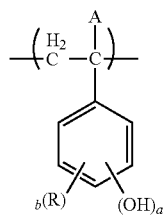

(1)

In General Formula (1),

A represents a hydrogen atom, an alkyl group, a cycloalkyl group, a halogen atom, or a cyano group.

R represents a halogen atom, an alkyl group, a cycloalkyl group, an aryl group, an alkenyl group, an aralkyl group, an alkoxy group, an alkylcarbonyloxy group, an alkylsulfonyloxy group, an alkyloxycarbonyl group, or an aryloxycarbonyl group, and in a case where a plurality of R's are present, R's may be the same as or different from each other. In a case where there are a plurality of R's, R's may be combined with each other to form a ring. As R, the hydrogen atom is preferable.

a represents an integer of 1 to 3.

b represents an integer of 0 to (3-a).

Specific examples of the repeating unit represented by General Formula (I) will be shown below, but the present invention is not limited thereto. In the formula, a represents 1 or 2.

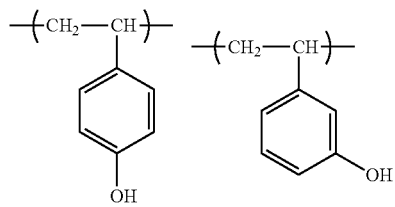

-continued

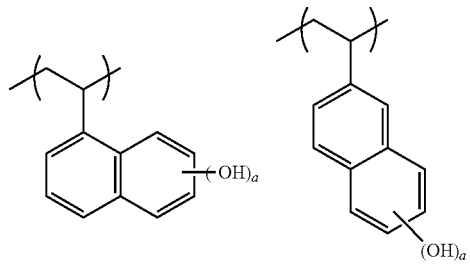

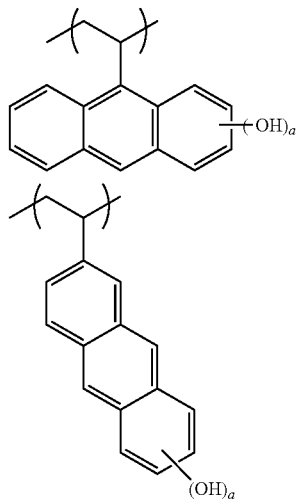

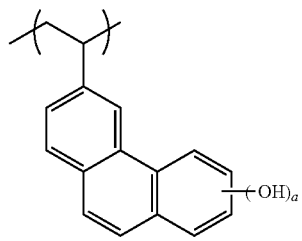

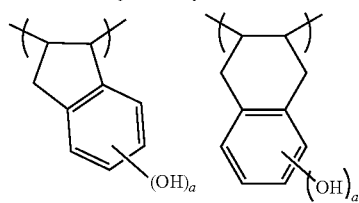

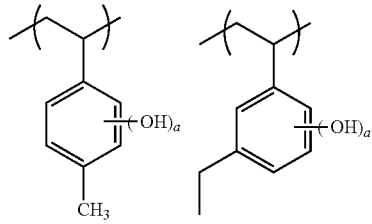

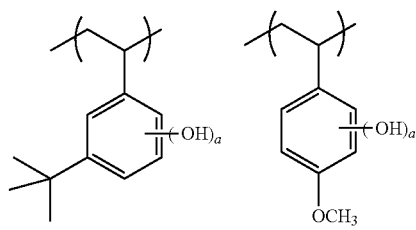

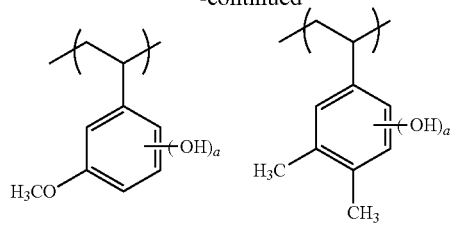
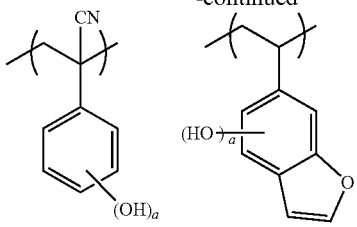
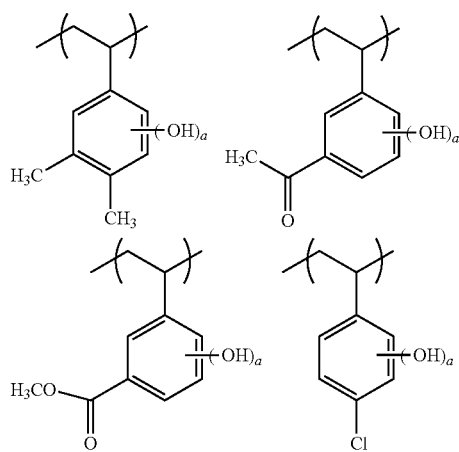
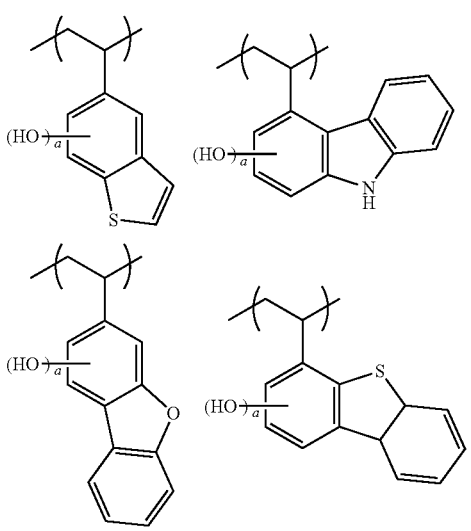
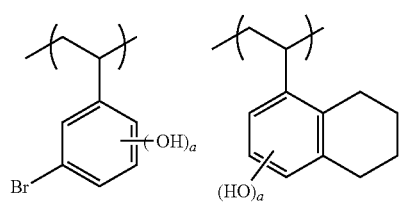
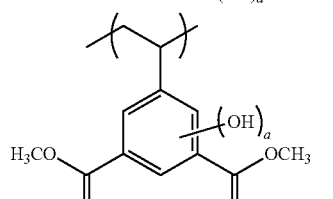
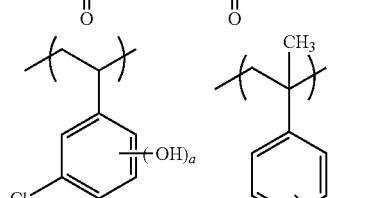
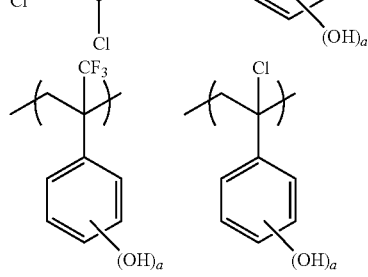
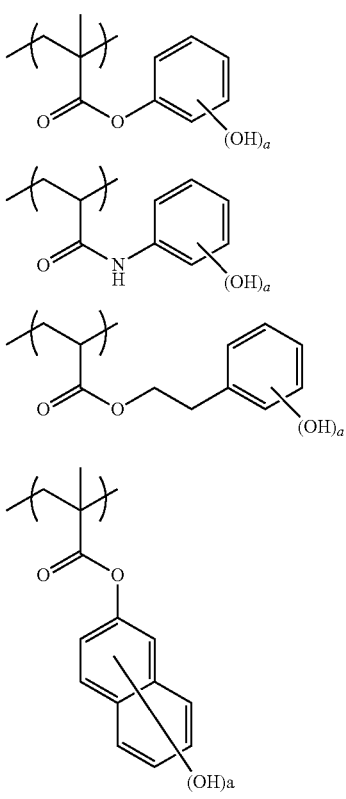

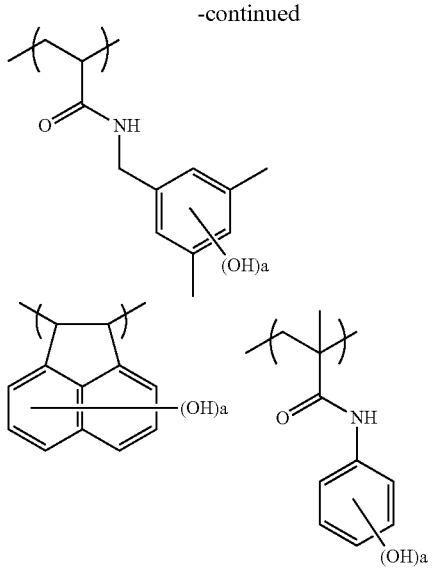
Moreover, among the repeating units, the repeating units specifically described below are preferable. In the formulae, R represents a hydrogen atom or a methyl group, and a represents 1, 2, or 3.
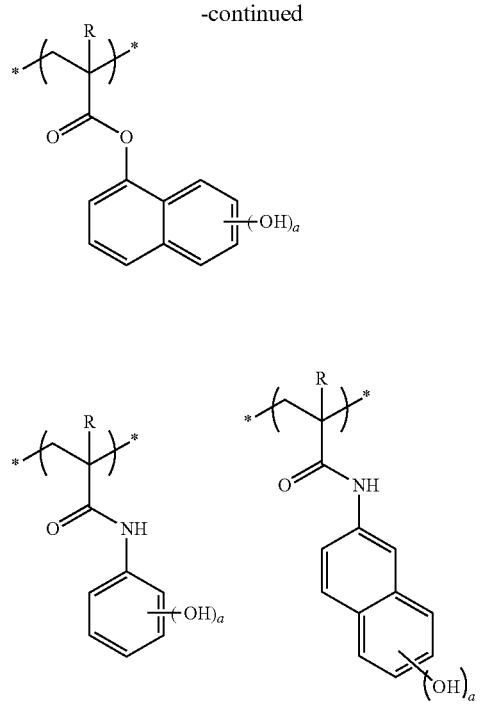

-continued

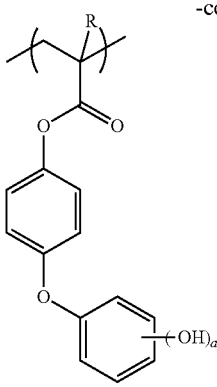

The content of the repeating unit having an acid group is preferably 10% to 80% by mole, more preferably 15%/to 75% by mole, and still more preferably 20% to 70% by mole, with respect to all the repeating units in the resin (A).

The resin (A) may have a variety of repeating units, in addition to the above-mentioned repeating structural units, for the purpose of adjusting dry etching resistance, suitability for a standard developer, adhesiveness to a substrate, a resist profile, a resolving power, heat resistance, sensitivity, and the like; and other purposes.

The resin (A) can be synthesized in accordance with an ordinary method (for example, radical polymerization). Examples of the general synthesis method include (1) a batch polymerization method in which polymerization is performed by dissolving monomer species and an initiator in a solvent and heating the solution, and (2) a dropwise addition polymerization method in which a solution containing monomer species and an initiator is added dropwise to a heating solvent for 1 to 10 hours.

The weight-average molecular weight (Mw) of the resin (A) is preferably 1,000 to 200,000, more preferably 2,000 to 30,000, and still more preferably 3,000 to 25,000. The dispersity (Mw/Mn) is usually 1.0 to 3.0, preferably 1.0 to 2.6, more preferably 1.0 to 2.0, and still more preferably 1.1 to 2.0.

The resin (A) may be used singly or in combination of two or more kinds thereof.

The content of the resin (A) in the composition of the embodiment of the present invention is usually 20% by mass or more in many cases, preferably 40% by mass or more, more preferably 50% by mass or more, and still more preferably 60% by mass or more, with respect to the total solid content. The upper limit is not particularly limited, but is preferably 99.5% by mass or less, more preferably 99% by mass or less, and still more preferably 98% by mass or less.

In addition, the total solid content of the composition of the embodiment of the present invention means other components (components that can constitute an actinic ray-sensitive or radiation-sensitive film) excluding the solvent.

[(B) Compound that Generates Acid Upon Irradiation with Actinic Rays or Radiation and is Represented by General Formula (1)]

As described above, the actinic ray-sensitive or radiation-sensitive resin composition of the embodiment of the present invention contains (B) a compound that generates an acid upon irradiation with actinic rays or radiation and is represented by General Formula (1) (hereinafter also referred to as a "compound (B)" or a "photoacid generator (B)").

The compound (B) is a compound that generates an acid upon irradiation with actinic rays or radiation (photoacid generator).

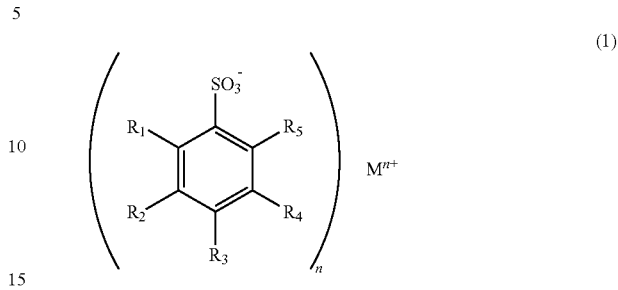

In General Formula (1), $R_1$ and $R_5$ each independently represent an aryl group or a heteroaryl group. $R_2$ to $R_4$ each independently represent a hydrogen atom or a substituent. $M^{n+}$ represents a cation. n represents an integer of 1 or more.

According to the present invention, it is possible to obtain an actinic ray-sensitive or radiation-sensitive resin composition which can attain both an improvement of a resolving power and a reduction in development defects at a high level by using the compound (B) in addition to the resin (A), and a reason thereof is not clear but is presumed as follows.

First, in General Formula (1), $R_1$ and $R_5$ each independently represent an aryl group or a heteroaryl group. Here, since $R_1$ and $R_5$ are each at the 2-position and the 6-position with respect to the carbon atom bonded to a sulfonate anion, it can be said that $R_1$ and $R_5$ are at adjacent positions of the sulfonate anion. Further, the aryl group or the heteroaryl group is a bulky group. Therefore, it is considered that $R_1$ and $R_5$ can each function as a sterically hindered group for the sulfonate anion. As a result, it is presumed that an acid generated in the exposed area of the compound (B) having such a sulfonate anion is less likely to be excessively diffused in the unexposed area, and thus, the resolving power is improved.

Meanwhile, in general, in a case where a bulky group is introduced into an acid generator, an increase in the hydrophobicity of the acid generator, and the like are caused, and there is thus a possibility that development defects associated with the development residues easily occur during alkali development.

However, in a case where the compound (B) of the present invention in which $R_1$ and $R_5$ are each an aryl group or a heteroaryl group is used, development defects associated with development residues are remarkably further suppressed, as compared with a case where an acid generator or the like in which $R_1$ and $R_5$ are each substituted with a cycloalkyl group which are also bulky is used. A detailed reason thereof is not clear, but it is considered that since the ClogP value of the aryl group or the heteroaryl group is lower than the ClogP value of the cycloalkyl group, and the compound (B) of the present invention has a high affinity for an alkali developer, the development defects associated with the development residues are suppressed while having the aryl group or the heteroaryl group as a bulky group.

In General Formula (1), $R_1$ and $R_5$ each independently represent an aryl group or a heteroaryl group. $R_2$ to $R_4$ each independently represent a hydrogen atom or a substituent. $M^{n+}$ represents a cation. n represents an integer of 1 or more.

Examples of the aryl group as each of $R_1$ and $R_5$ include an aryl group having 6 to 15 carbon atoms, and specifically, preferred examples thereof include a phenyl group, a naphthyl group, and an anthryl group.

Examples of the heteroaryl group as each of $R_1$ and $R_5$ include a heteroaryl group having 2 to 15 carbon atom and a 5- to 10-membered ring, and specifically include a furyl group, a thienyl group, a pyrrolyl group, an oxazolyl group, a pyridyl group, a quinolinyl group, and a carbazolyl group.

The substituent as each of $R_2$ to $R_4$ is not particularly limited as long as it is a monovalent substituent, but examples thereof include an alkyl group; an alkenyl group; a cycloalkyl group; an aryl group; a halogen atom; a group including a heteroatom such as an oxygen atom, a sulfur atom, a nitrogen atom, and a silicon atom; and a combination of two or more kinds thereof.

Examples of the alkyl group as each of $R_2$ to $R_4$ include an alkyl group having 1 to 30 carbon atoms. The alkyl group is preferably an alkyl group having 1 to 20 carbon atoms, such as a methyl group, an ethyl group, a propyl group, an isopropyl group, an n-butyl group, a sec-butyl group, a hexyl group, a 2-ethylhexyl group, an octyl group, and a dodecyl group, and more preferably an alkyl group having 1 to 8 carbon atoms.

Examples of the alkenyl group as each of $R_2$ to $R_4$ include an alkenyl group having 2 to 30 carbon atoms, and an alkenyl group having 2 to 8 carbon atoms is preferable.

The cycloalkyl group as each of $R_2$ to $R_4$ may be monocyclic or polycyclic. The number of carbon atoms of this cycloalkyl group is not particularly limited, but is preferably 3 to 8.

Examples of the aryl group as each of $R_2$ to $R_4$ include an aryl group having 6 to 15 carbon atoms, and specifically, preferred examples thereof include a phenyl group, a naphthyl group, and an anthryl group.

Examples of the halogen atom as each of $R_2$ to $R_4$ include a fluorine atom, a chlorine atom, a bromine atom, and an iodine atom.

Examples of the group including a heteroatom include a hydroxyl group, a carboxyl group, an alkoxy group, a thiol group, a thioether group, a nitro group, a nitroso group, a cyano group, an amino group, an acyloxy group, an acylamido group, a heteroaryl group, an ether bond, a carbonyl bond, and a combination of two or more kinds thereof.

Each of the alkoxy group, the acyloxy group, and the acylamido group preferably has 20 or less carbon atoms, and more preferably has 8 or less carbon atoms. Examples of the alkoxy group include a methoxy group, an ethoxy group, a propoxy group, an isopropoxy group, an n-butyloxy group, a t-butoxy group, and an octyloxy group. Among these, a methoxy group, an ethoxy group, a propoxy group, an isopropoxy group, and a t-butoxy group are particularly preferable. Further, examples of the thioether group also include the same ones as those of the alkoxy group, except that a sulfur atom is used instead of the oxygen atom. Examples of the acyloxy group include an acetyloxy group. Examples of the acylamido group include an acetylamido group.

Examples of the heteroaryl group include the same groups as ones of the heteroaryl groups as each of $R_1$ and $R_5$.

The aryl group and the heteroaryl group as one of $R_1$ and $R_5$ may each further have a substituent. Examples of the substituent to be further contained include an alkyl group; an alkenyl group; a cycloalkyl group; an aryl group; a halogen atom; a group including a heteroatom such as an oxygen atom, a sulfur atom, a nitrogen atom, and a silicon atom; and a combination of two or more kinds thereof.

The alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof are the same as the alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof in the specific examples of the substituent of each of $R_2$ to $R_4$, respectively.

In a case where the aryl group or the heteroaryl group as each of $R_1$ and $R_5$ have a plurality of substituents, at least two of the plurality of substituents may be bonded to each other to form a ring.

The alkyl group; the alkenyl group; the cycloalkyl group; the aryl group; and the group including a heteroatom such as an oxygen atom, a sulfur atom, a nitrogen atom, and a silicon atom as the substituent of each of $R_2$ to $R_4$ may further have a substituent. Examples of the substituent to be further contained include an alkyl group, an alkenyl group, a cycloalkyl group, an aryl group, an amino group, an amido group, a ureido group, a urethane group, a hydroxyl group, a carboxy group, a halogen atom, an alkoxy group, a thioether group, an acyl group, an acyloxy group, an alkoxycarbonyl group, a cyano group, a nitro group, and a combination of two or more kinds thereof.

$R_1$ and $R_5$ can each constitute a group including a polar group, a group including a group having a polarity that increases through decomposition by an action of an acid, or a group including a group having a solubility in an alkali developer that increases through decomposition by an action of an alkali developer, each of which will be described later.

$R_2$ to $R_4$ can each constitute the group including a polar group, the group including a group having a polarity that increases through decomposition by an action of an acid, or the group including a group having a solubility in an alkali developer that increases through decomposition by an action of an alkali developer, each of which will be described later.

In General Formula (1), $R_3$ preferably represents an aryl group.

Examples of the aryl group as $R_3$ include the same ones as those of the aryl groups as each of $R_1$ and $R_5$.

The aryl group as $R_3$ may further have a substituent. Examples of the substituent to be further contained include the respective groups described above as the specific examples of the substituents which may be further contained in each of $R_1$ and $R_5$ as mentioned above. In a case where the aryl group as $R_3$ has a plurality of substituents, at least two of the plurality of substituents may be bonded to each other to form a ring.

In General Formula (1), from the viewpoint that it is possible to further reduce development defects, it is preferable that at least one of $R_1, \ldots,$ or $R_5$ is a group including a polar group, a group including a group having a polarity that increases through decomposition by an action of an acid, or a group including a group having a solubility in an alkali developer that increases through decomposition by an action of an alkali developer.

Examples of the polar group in the group including a polar group as at least one of $R_1, \ldots,$ or $R_5$ include an acidic group such as a carboxyl group, a phenolic hydroxyl group, a fluorinated alcohol group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl) imido group, a bis(alkylsulfonyl)methylene group, a bis (alkylsulfonyl)imido group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol group (for example, a hexafluoroisopropanol group) having the α-position substituted with an electron-withdrawing group such as a fluorine atom is excluded as a hydroxyl group. The alcoholic hydroxyl group is preferably a hydroxyl group having an acid dissociation constant (pKa) from 12 to 20.

Among those, as the polar group, the carboxyl group, the phenolic hydroxyl group, or the fluorinated alcohol group (preferably the hexafluoroisopropanol group) is preferable.

Examples of the group including a polar group also include a group having a carbonyl bond.

Examples of the group having a carbonyl bond include an alkylcarbonyl group and an arylcarbonyl group.

Examples of the alkyl group include the same ones as those of the alkyl group as each of $R_2$ to $R_4$.

Examples of the aryl group include the same ones as those of the aryl group as each of $R_1$ and $R_5$.

The group having a carbonyl bond is a group in which a carbonyl bond and an ether bond are not adjacent to be bonded to each other.

The alkylcarbonyl group or the arylcarbonyl group as the group having a carbonyl bond may further have a substituent.

Examples of the substituent to be further contained include an alkyl group; an alkenyl group; a cycloalkyl group; an aryl group; a halogen atom; a group including a heteroatom such as an oxygen atom, a sulfur atom, a nitrogen atom, and a silicon atom; and a combination of two or more kinds thereof.

The alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof are the same as the alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof in the specific examples of the substituent of each of $R_2$ to $R_4$, respectively.

The group including a polar group is not particularly limited, but examples thereof include an organic group including a polar group. Examples of the organic group including a polar group include an alkyl group; an alkenyl group; a cycloalkyl group; an aryl group; a halogen atom; a group including a heteroatom such as an oxygen atom, a sulfur atom, a nitrogen atom, and a silicon atom; and a combination of two or more kinds thereof, each of which includes a polar group.

The alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof are the same as the alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof in the specific examples of the substituent of each of $R_2$ to $R_4$, respectively.

Examples of the group including a polar group include an alkyl group including a polar group and an aryl group including a polar group.

Examples of the alkyl group in the alkyl group including a polar group include the same ones as those of the alkyl group as each of $R_2$ to $R_4$.

Examples of the aryl group in the aryl group including a polar group include the same ones as those of the aryl group as each of $R_1$ and $R_5$.

In addition, the group including a polar group may be a polar group itself.

The group having a polarity that increases through decomposition by an action of an acid (hereinafter also referred to as an "acid-decomposable group") in the group having a group having a polarity that increases through decomposition by an action of an acid as at least one of $R_1$, ..., or $R_5$ preferably has a structure in which a polar group is protected with a group that is eliminated through decomposition by an action of an acid (eliminable group).

Examples of the polar group include the same ones as those of the polar group in the group including a polar group as at least one of $R_1$, ..., or $R_5$.

Examples of the group that is eliminated through decomposition by an action of an acid (eliminable group) include groups represented by Formulae (Y1) to (Y4).

  Formula (Y1):

—C($Rx_1$)($Rx_2$)($Rx_3$)

  Formula (Y2):

—C(=O)OC($Rx_1$)($Rx_2$)($Rx_3$)

  Formula (Y3):

—C($R_{36}$)($R_{37}$)($OR_{38}$).

  Formula (Y4):

—C(Rn)(H)(Ar)

In Formula (Y1) and Formula (Y2), $Rx_1$ to $Rx_3$ each independently represent an (linear or branched) alkyl group or a (monocyclic or polycyclic) cycloalkyl group. Furthermore, in a case where all of $Rx_1$ to $Rx_3$ are (linear or branched) alkyl groups, it is preferable that at least two of $Rx_1$, $Rx_2$, or $Rx_3$ are methyl groups.

Among those, it is preferable that $Rx_1$ to $Rx_3$ each independently represent a linear or branched alkyl group, and it is more preferable that $Rx_1$ to $Rx_3$ each independently represent a linear alkyl group.

Two of $Rx_1$ to $Rx_3$ may be bonded to each other to form a monocycle or polycycle.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group, and a polycyclic cycloalkyl group such as a norbornyl group, a tetracyclodecanyl group, a tetracyclododecanyl group, and an adamantyl group are preferable, and a monocyclic cycloalkyl group having 5 or 6 carbon atoms is more preferable.

In the cycloalkyl group formed by the bonding of two of $Rx_1$ to $Rx_3$, for example, one of the methylene groups constituting the ring may be substituted with a heteroatom such as an oxygen atom or a group having a heteroatom, such as a carbonyl group.

With regard to the group represented by Formula (Y1) or Formula (Y2), for example, an aspect in which $Rx_1$ is a methyl group or an ethyl group, and $Rx_2$ and $Rx_3$ are bonded to each other to form a cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. It is also preferable that $R_{36}$ is the hydrogen atom.

As Formula (Y3), a group represented by Formula (Y3-1) is preferable.

(Y3-1)

Here, $L_1$ and $L_2$ each independently represent a hydrogen atom, an alkyl group, a cycoalkyl group, an aryl group, or a group formed by combination thereof (for example, a group formed by a combination of an alkyl group and an aryl group).

M represents a single bond or a divalent linking group.

Q represents an alkyl group which may include a heteroatom, a cycloalkyl group which may include a heteroatom, an aryl group which may include a heteroatom, an amino group, an ammonium group, a mercapto group, a cyano group, an aldehyde group, or a group formed by combination thereof (for example, a group formed by a combination of an alkyl group and a cycloalkyl group).

In the alkyl group and the cycloalkyl group, for example, one of the methylene groups may be substituted with a heteroatom such as an oxygen atom or a group having a heteroatom, such as a carbonyl group.

In addition, it is preferable that one of $L_1$ or $L_2$ is a hydrogen atom, and the other is an alkyl group, a cycloalkyl group, an aryl group, or a group formed by combination of an alkylene group and an aryl group.

At least two of Q, M, or $L_1$ may be bonded to each other to form a ring (preferably a 5-membered or 6-membered ring).

From the viewpoint of pattern miniaturization, $L_2$ is preferably a secondary or tertiary alkyl group, and more preferably the tertiary alkyl group. Examples of the secondary alkyl group include an isopropyl group, a cyclohexyl group, and a norbornyl group, and examples of the tertiary alkyl group include a tert-butyl group and an adamantane group. In these aspects, since the glass transition temperature (Tg) and the activation energy are higher, it is possible to suppress fogging in addition to ensuring film hardness.

In Formula (Y4), Ar represents an aromatic ring group. Rn represents an alkyl group, a cycloalkyl group, or an aryl group. Rn and Ar may be bonded to each other to form a non-aromatic ring. Ar is more preferably an aryl group.

The acid-decomposable group preferably has an acetal structure. The acetal structure is, for example, a structure in which a polar group such as a carboxyl group, a phenolic hydroxyl group, and a fluorinated alcohol group is protected with the group represented by Formula (Y3).

The group including an acid-decomposable group is not particularly limited as long as it is a group including an acid-decomposable group, and examples thereof include an organic group including an acid-decomposable group. Examples of the organic group including an acid-decomposable group include an alkyl group; an alkenyl group; a cycloalkyl group; an aryl group; a halogen atom; a group including a heteroatom such as an oxygen atom, a sulfur atom, a nitrogen atom, and a silicon atom; and a combination of two or more kinds thereof, each of which has an acid-decomposable group.

The alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof are the same as the alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof in the specific examples of the substituent of each of $R_2$ to $R_4$, respectively.

Examples of the group including an acid-decomposable group include an alkyl group including an acid-decomposable group and an aryl group including an acid-decomposable group.

Examples of the alkyl group in the alkyl group including an acid-decomposable group include the same ones as those of the alkyl group as each of $R_2$ to $R_4$.

Examples of the aryl group in the aryl group including an acid-decomposable group include the same ones as those of the aryl group as each of $R_1$ and $R_5$.

In addition, the group including the acid-decomposable group may be an acid-decomposable group itself.

The group having a solubility in an alkali developer that increases through decomposition by an action of an alkali developer in the group having the group having a solubility in an alkali developer that increases through decomposition by an action of an alkali developer as at least one of $R_1, \ldots,$ or $R_5$ is also referred to as a "polarity conversion group", and specific examples thereof include a lactone group, a carboxylic acid ester group (—COO—), an acid anhydride group (—C(O)OC(O)—), an acid imido group (—NHCONH—), a carboxylic acid thioester group (—COS—), a carbonic acid ester group (—OC(O)O—), a sulfuric acid ester group (—OSO$_2$O—), and a sulfonic acid ester group (—SO$_2$O—).

Examples of the group including a polarity conversion group include an acyloxy group, an alkoxycarbonyloxy group, an aryloxycarbonyloxy group, an aryloxycarbonyl group, an alkoxycarbonyl group, a carbamoyl group, and an imido group.

The acyl group in the acyloxy group preferably has 1 to 30 carbon atoms, and more preferably has 1 to 8 carbon atoms.

The alkoxy group in the alkoxycarbonyloxy group preferably has 1 to 30 carbon atoms, and more preferably has 1 to 8 carbon atoms.

The aryl group in the aryloxycarbonyloxy group preferably has 6 to 14 carbon atoms, and more preferably has 6 to 10 carbon atoms.

The aryl group in the arloxycarbonyl group preferably has 6 to 14 carbon atoms, and more preferably 6 to 10 carbon atoms.

The alkoxy group in the alkoxycarbonyl group preferably has 1 to 30 carbon atoms, and more preferably has 1 to 8 carbon atoms.

The imido group is a group obtained by removing one hydrogen atom from an imide.

The acyloxy group, the alkoxycarbonyloxy group, the aryloxycarbonyloxy group, the aryloxycarbonyl group, the alkoxycarbonyl group, the carbamoyl group, and the imido group may further have a substituent.

Examples of the substituent to be further contained include the respective groups described above as the specific examples of the substituents which may be further contained in each of $R_1$ and $R_5$ as mentioned above.

In one preferred aspect of the present invention, the polarity conversion group is a group represented by X in a partial structure represented by General Formula (KA-1) or (KB-1).

(KA-1)

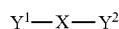

(KB-1)

X in General Formula (KA-1) or (KB-1) represents a carboxylic acid ester group; —COO—, an acid anhydride group: —C(O)OC(O)—, an acid imido group: —NHCONH—, a carboxylic acid thioester group: —COS—, a carbonic acid ester group: —OC(O)O—, a sulfuric acid ester group: —OSO$_2$O—, and a sulfonic acid ester group: —SO$_2$O—.

$Y^1$ and $Y^2$ may be the same as or different from each other, and each represent an electron-withdrawing group.

In addition, in one preferred aspect of the present invention, the compound (B) has a group having the partial structure represented by General Formula (KA-1) or (KB-1) as a group containing a polarity conversion group, but in a case where the partial structure does not have a bond, such as a case of the partial structure represented by General Formula (KA-1) and the partial structure represented by General Formula (KB-1) in which $Y^1$ and $Y^2$ are monovalent, the group having the partial structure is a group having a monovalent or higher-valent group obtained by removing at least any one hydrogen atom in the partial structure.

The partial structure represented by General Formula (KA-1) is a structure that forms a ring structure together with the group as X.

As X in General Formula (KA-1), a carboxylic acid ester group (that is, in a case of forming a lactone ring structure as KA-1), an acid anhydride group, or a carbonic acid ester group is preferable. The carboxylic acid ester group is more preferable.

The ring structure represented by General Formula (KA-1) may have a substituent, and for example, may have nka substituents $Z_{ka1}$.

In a case where a plurality of $Z_{ka1}$'s are present, $Z_{ka1}$'s each independently represent an alkyl group, a cycloalkyl group, an ether group, a hydroxyl group, an amido group, an aryl group, a lactone ring group, or an electron-withdrawing group.

$Z_{ka1}$'s may be linked to each other to form a ring. Examples of the ring formed by the mutual linkage of $Z_{ka1}$'s include a cycloalkyl ring and a heterocycle (a cyclic ether ring, a lactone ring, and the like).

nka represents an integer of 0 to 10. nka is preferably an integer of 0 to 8, more preferably an integer of 0 to 5, still more preferably an integer of 1 to 4, and most preferably an integer of 1 to 3.

The electron-withdrawing group as $Z_{ka1}$ is the same as the electron-withdrawing group as each of $Y^1$ and $Y^2$ which will be described later, typified by a halogen atom.

In addition, the electron-withdrawing group may be substituted with another electron-withdrawing group.

$Z_{ka1}$ is preferably the alkyl group, the cycloalkyl group, the ether group, the hydroxyl group, or the electron-withdrawing group, and more preferably the alkyl group, the cycloalkyl group, or the electron-withdrawing group. In addition, the ether group is preferably an ether group substituted with an alkyl group, a cycloalkyl group, or the like, that is, an alkyl ether group or the like. Preferred examples of the electron-withdrawing group are the same ones as those of the electron-withdrawing group as each of $Y^1$ and $Y^2$ which will be described later.

Examples of the halogen atom as $Z_{ka1}$ include a fluorine atom, a chlorine atom, a bromine atom, and an iodine atom, and the fluorine atom is preferable.

The alkyl group as $Z_{ka1}$ may have a substituent and may be either linear or branched. The linear alkyl group preferably has 1 to 30 carbon atoms, and more preferably has 1 to 20 carbon atoms, and examples thereof include a methyl group, an ethyl group, an n-propyl group, an n-butyl group, a sec-butyl group, a t-butyl group, an n-pentyl group, an n-hexyl group, an n-heptyl group, an n-octyl group, an n-nonyl group, and an n-decanyl group. The branched alkyl group preferably has 3 to 30 carbon atoms, and more preferably has 3 to 20 carbon atoms, and examples thereof include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, and a t-decanoyl group. The alkyl groups having 1 to 4 carbon atoms, such as a methyl group, an ethyl group, an n-propyl group, an i-propyl group, an n-butyl group, an i-butyl group, and a t-butyl group, are preferable.

The cycloalkyl group as $Z_{ka1}$ may have a substituent, may be monocyclic or polycyclic, and may also be bridged. For example, the cycloalkyl group may have a bridged structure. As the monocyclic group, a cycloalkyl group having 3 to 8 carbon atoms is preferable, and examples thereof include a cyclopropyl group, a cyclopentyl group, a cyclohexyl group, a cyclobutyl group, and a cyclooctyl group. Examples of the polycyclic group include groups having 5 or more carbon atoms, having a bicyclo, tricyclo, or tetracyclo structure, or the like, cycloalkyl groups having 6 to 20 carbon atoms are preferable, and examples thereof include an adamantyl group, a norbornyl group, an isobornyl group, a camphanyl group, a dicyclopentyl group, an α-pinene group, a tricyclodecanyl group, a tetracyclododecyl group, and an androstanyl group. The following structure is also preferable as the cycloalkyl group. In addition, some of the carbon atoms in the cycloalkyl group may be substituted with heteroatoms such as an oxygen atom.

(1)

(2)

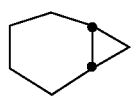

(3)

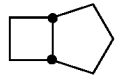

(4)

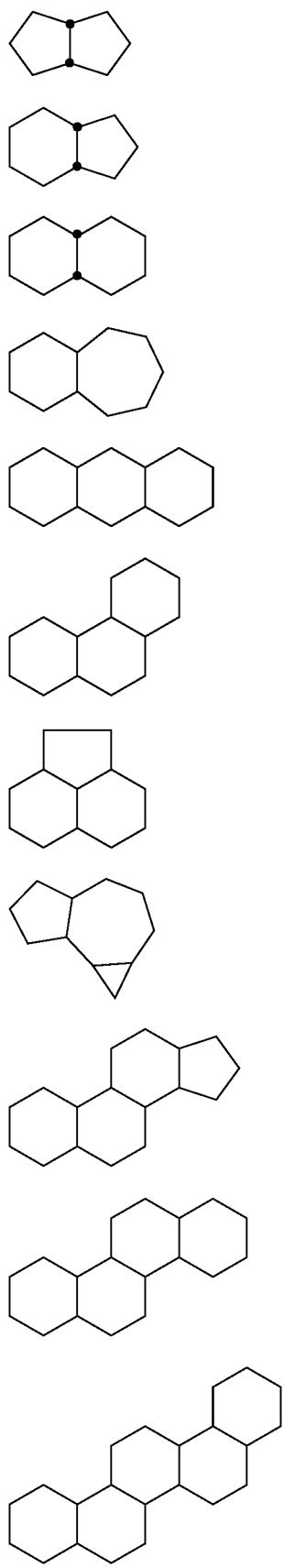
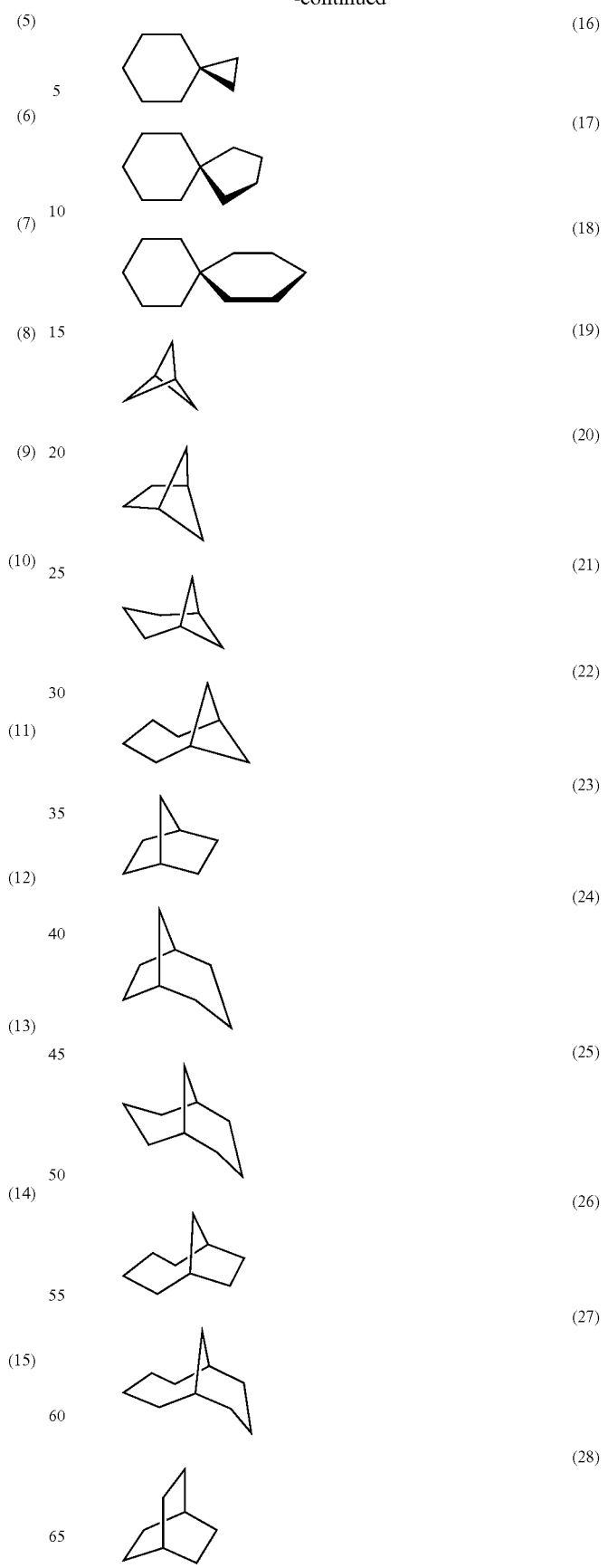

-continued

(29) 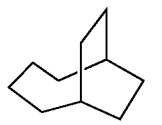

(30) 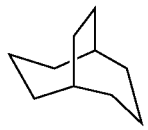

(31) 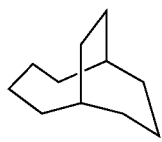

(32) 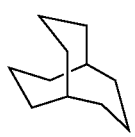

(33) 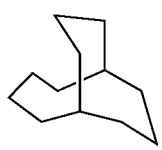

(34) 

(35) 

(36) 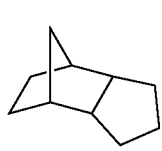

(37) 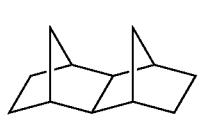

(38) 

(39) 

(40) 

-continued

(41) 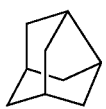

(42) 

(43) 

(44) 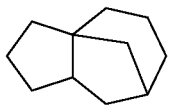

(45) 

(46) 

(47) 

(48) 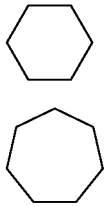

(49)

(50) 

Preferred examples of the alicyclic moiety include an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group, and a cyclododecanyl group. More preferred are the adamantyl group, the decalin group, the norbornyl group, the cedrol group, the cyclohexyl group, the cycloheptyl group, the cyclooctyl group, the cyclodecanyl group, the cyclododecanyl group, and the tricyclodecanyl group.

Examples of the substituent having the alicyclic structure include an alkyl group, a halogen atom, a hydroxyl group, an alkoxy group, a carboxyl group, and an alkoxycarbonyl group. As the alkyl group, a lower alkyl group such as a methyl group, an ethyl group, a propyl group, an isopropyl group, and a butyl group is preferable, and the methyl group, the ethyl group, the propyl group, or the isopropyl group is more preferable. As the alkoxy group, those having 1 to 4 carbon atoms, such as a methoxy group, an ethoxy group, a propoxy group, and a butoxy group, are preferable. Examples of the substituent which may be contained in each of the alkyl group and the alkoxy group include a hydroxyl group, a halogen atom, and an alkoxy group (preferably having 1 to 4 carbon atoms).

Examples of the lactone ring group of $Z_{ka1}$ include groups obtained by removing a hydrogen atom from a structure represented by any of (KA-1-1) to (KA-1-17) which will be described later.

Examples of the aryl group of $Z_{ka1}$ include a phenyl group and a naphthyl group.

Examples of the substituent which can further be contained in the alkyl group, the cycloalkyl group, or the aryl group of $Z_{ka1}$ include a hydroxyl group, a halogen atom (fluorine, chlorine, bromine, and iodine), a nitro group, a cyano group, an alkyl group, an alkoxy group such as a methoxy group, an ethoxy group, a hydroxyethoxy group, a propoxy group, a hydroxypropoxy group, an n-butoxy group, an isobutoxy group, a sec-butoxy group, and a t-butoxy group, an alkoxycarbonyl group such as a methoxycarbonyl group and an ethoxycarbonyl group, an aralkyl group such as a benzyl group, a phenethyl group, and a cumyl group, an aralkyloxy group, an acyl group such as a formyl group, an acetyl group, a butyryl group, a benzoyl group, a cynamyl group, and a valeryl group, an acyloxy group such as a butyryloxy group, an alkenyl group, an alkenyloxy group such as a vinyloxy group, a propenyloxy group, an allyloxy group, and a butenyloxy group, an aryl group, an aryloxy group such as a phenoxy group, and an aryloxycarbonyl group such as a benzoyloxy group.

It is preferable that X in General Formula (KA-1) is the carboxylic acid ester group and the partial structure represented by General Formula (KA-1) is the lactone ring, and preferably a 5- to 7-membered lactone ring.

In addition, as in (KA-1-1) to (KA-1-17), it is preferable that another ring structure is fused to the 5- to 7-membered lactone ring as the partial structure represented by General Formula (KA-1) to form a bicyclo structure or a spiro structure.

Examples of the peripheral ring structure to which the ring structure represented by General Formula (KA-1) may be bonded include the rings for (KA-1-1) to (KA-1-17), or a ring equivalent thereto.

As a structure containing the lactone ring structure represented by General Formula (KA-1), the structures represented by any of (KA-1-1) to (KA-1-17) are more preferable. Further, the lactone structure may be directly bonded to the main chain. Preferred examples of the structure include (KA-1-1), (KA-1-4), (KA-1-5), (KA-1-6), (KA-1-13), (KA-1-14), and (KA-1-17).

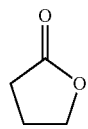

KA-1-1

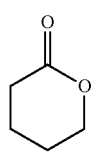

KA-1-2

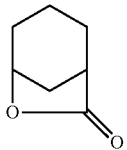

KA-1-3

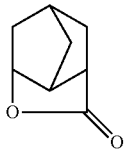

KA-1-4

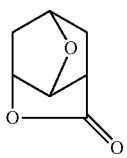

KA-1-5

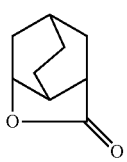

KA-1-6

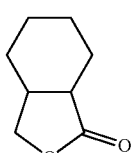

KA-1-7

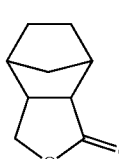

KA-1-8

KA-1-9

KA-1-10

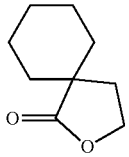

KA-1-11

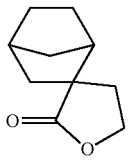

KA-1-12

KA-1-13-
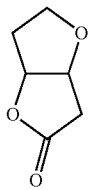

KA-1-14
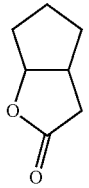

KA-1-15
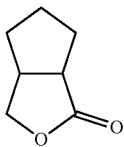

KA-1-16
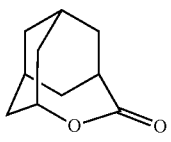

KA-1-17
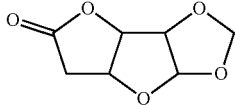

The structure containing the lactone ring structure may or may not have a substituent. Preferred examples of the substituent include the same ones as those of the substituent which may be contained in the ring structure represented by General Formula (KA-1).

The lactone structure may have an optically active substance, but any of optically active substances may be used. In addition, one kind of optically active substances may be used singly or a plurality of kinds of optically active substances may be mixed and used. In a case where one kind of optically active substance is mainly used, an optical purity (ee) thereof is preferably 90% or more, more preferably 95% or more, and most preferably 98% or more.

Preferred examples of X in General Formula (KB-1) include a carboxylic acid ester group (—COO—).

$Y^1$ and $Y^2$ in General Formula (KB-1) each independently represent an electron-withdrawing group.

The electron-withdrawing group is preferably a partial structure represented by Formula (EW). In Formula (EW), * represents a bond directly linked to (KA-1) or a bond directly linked to X in (KB-1).

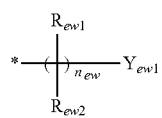

(EW)

In Formula (EW), $n_{ew}$ is a repetition number of the linking groups represented by —C($R_{ew1}$)($R_{ew2}$)— and represents an integer of 0 or 1. In a case where $n_{ew}$ is 0, this indicates that the bonding is formed by a single bond and $Y_{ew1}$ is directly bonded.

$Y_{ew1}$ is a halogen atom, a cyano group, a nitrile group, a nitro group, a halo(cyclo)alkyl group or haloaryl group represented by —C($R_{f1}$)($R_{f2}$)—$R_{f3}$ which will be described later, an oxy group, a carbonyl group, a sulfonyl group, a sulfinyl group, or a combination thereof, and the electron-withdrawing group may be, for example, the following structure. In addition, the "halo(cyclo)alkyl group" represents an alkyl or cycloalkyl group which is at least partially halogenated. $R_{ew3}$ and $R_{ew4}$ each independently represent any structure. Regardless of the structures of $R_{ew3}$ and $R_{ew4}$, the partial structure represented by Formula (EW) has an electron-withdrawing property, and is preferably an alkyl group, a cycloalkyl group, or a fluorinated alkyl group.

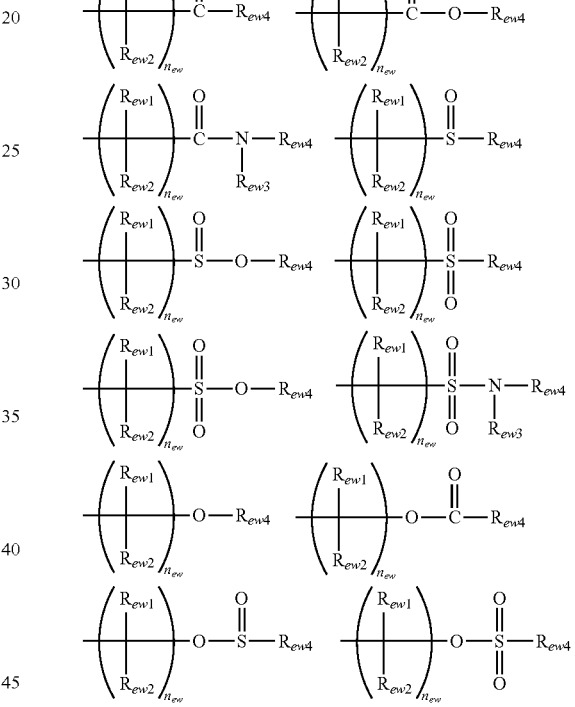

In a case where $Y_{ew1}$ is a divalent or higher-valent group, the remaining bond forms a bond with any atom or substituent.

$Y_{ew1}$ is preferably a halogen atom, or a halo(cyclo)alkyl group or haloaryl group represented by —C($R_{f1}$)($R_{f2}$)—$R_{f3}$.

$R_{ew1}$ and $R_{ew2}$ each independently represent any substituent, and represent, for example, a hydrogen atom, an alkyl group, a cycloalkyl group, or an aryl group.

At least two of $R_{ew1}$, $R_{ew2}$, or $Y_{ew1}$ may be linked to each other to form a ring.

Here, $R_{f1}$ represents a halogen atom, a perhaloalkyl group, a perhalocycloalkyl group, or a perhaloaryl group, more preferably represents a fluorine atom, the perfluoroalkyl group, or the perfluorocycloalkyl group, and still more preferably represents the fluorine atom or a trifluoromethyl group.

$R_{f2}$ and $R_{f3}$ each independently represent a hydrogen atom, a halogen atom, or an organic group, and $R_{f2}$ and $R_{f3}$ may be linked to each other to form a ring. Examples of the organic group include an alkyl group, a cycloalkyl group, and an alkoxy group, and these may be substituted with a halogen atom (preferably a fluorine atom), and $R_{f2}$ and $R_{f3}$ are more preferably (halo)alkyl groups. It is more preferable that Rn represents the same group as $R_{f1}$ or is linked to $R_{f3}$ to form a ring.

$R_{f1}$ and $R_{f3}$ may be linked to form a ring, and examples of the ring formed include a (halo)cycloalkyl ring and a (halo) aryl ring.

Examples of the (halo)alkyl group in Rn to Rn include the alkyl group for $Z_{ka1}$ described above and a halogenated structure thereof.

Examples of the (per)halocycloalkyl group and the (per) haloaryl group in each of Rn to Rn or in the ring formed by the linkage between $R_{f2}$ and $R_{f3}$ include structures resulting from halogenation of the cycloalkyl groups in $Z_{ka1}$, and more preferably a fluorocycloalkyl group represented by —$C_{(n)}F_{(2n+2)}H$ and a perfluoroaryl group represented by —$C_{(n)}F_{(n+1)}$. Here, the number n of carbon atoms is not particularly limited, but is preferably 5 to 13, and more preferably 6.

Preferred examples of a ring which may be formed by the mutual linkage of at least two of $R_{ew1}$, $R_{ew2}$, or $Y_{ew1}$ include a cycloalkyl group and a heterocyclic group, and as the heterocyclic group, a lactone ring group is preferable. Examples of the lactone ring include the structures represented by Formulae (KA-1-1) to (KA-1-17).

Moreover, the compound (B) may have a plurality of the partial structures represented by General Formula (KA-1), a plurality of the partial structures represented by General Formula (KB-1), or both the partial structures of General Formula (KA-1) and General Formula (KB-1).

Furthermore, a part or a whole of the partial structure of General Formula (KA-1) may also serve as the electron-withdrawing group as $Y^1$ or $Y^2$ in General Formula (KB-1). For example, in a case where X in General Formula (KA-1) is a carboxylic acid ester group, the carboxylic acid ester group can function as an electron-withdrawing group as $Y^1$ or $Y^2$ in General Formula (KB-1).

The group including a polarity conversion group is not particularly limited, and examples thereof include an organic group including a polarity conversion group. Examples of the organic group including a polarity conversion group include an alkyl group; an alkenyl group; a cycloalkyl group; an aryl group, a halogen atom; a group including a heteroatom such as an oxygen atom, a sulfur atom, a nitrogen atom, and a silicon atom; and a combination of two or more kinds thereof, each of which includes a polarity conversion group.

The alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof are the same as the alkyl group; the alkenyl group; the cycloalkyl group; the aryl group; the halogen atom; the group including a heteroatom such as an oxygen atom, a sulfur atom, a nitrogen atom, and a silicon atom; and a combination of two or more kinds thereof in the specific examples of the substituent of each of $R_2$ to $R_4$, respectively.

Examples of the group including a polarity conversion group include an alkyl group including a polarity conversion group, and an aryl group including a polarity conversion group.

Examples of the alkyl group in the alkyl group including a polarity conversion group include the same ones as those of the alkyl group as each of $R_2$ to $R_4$.

Examples of the aryl group in the aryl group including a polarity conversion group include the same ones as those of the aryl groups as each of $R_1$ and $R_5$.

In General Formula (1), it is preferable that $R_1$, $R_3$, and $R_5$ are each a group represented by General Formula (Ar).

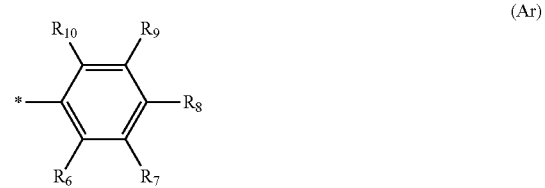

(Ar)

In General Formula (Ar), $R_6$ to $R_{10}$ each independently represent a hydrogen atom or a substituent. At least one of $R_6, \ldots,$ or $R_{10}$ is a group including a polar group, a group including a group having a polarity that increases through decomposition by an action of an acid, or a group including a group having a solubility in an alkali developer that increases through decomposition by an action of an alkali developer. * represents a bond to a benzene ring in General Formula (1).

Specific examples of the substituent as each of $R_6$ to $R_{10}$ are the same ones as the above-mentioned specific examples of the substituent as each of $R_2$ to $R_4$.

At least one of $R_6, \ldots,$ or $R_{10}$ is a group including a polar group, a group including a group having a polarity that increases through decomposition by an action of an acid, or a group including a group having a solubility in an alkali developer that increases through decomposition by an action of an alkali developer.

The group including a polar group is the same as the group including a polar group as at least one of $R_1, \ldots,$ or $R_5$.

The group including a group having a polarity that increases through decomposition by an action of an acid is the same as the group including a group having a polarity that increases through decomposition by an action of an acid as at least one of $R_1, \ldots,$ or $R_5$.

The group including a group having a solubility in an alkali developer that increases through decomposition by an action of an alkali developer is the same as the group including a group having a solubility in an alkali developer that increases through decomposition by an action of an alkali developer as at least one of $R_1, \ldots,$ or $R_5$.

Furthermore, in General Formula (1), it is preferable that $R_1$, $R_3$, and $R_5$ are each a group represented by General Formula (Ar1).

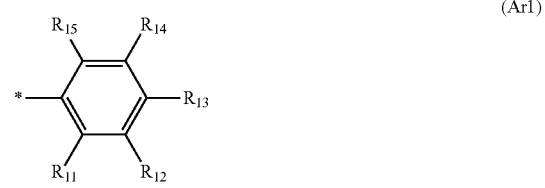

(Ar1)

In General Formula (Ar1), $R_{11}$ to $R_{15}$ each independently represent a hydrogen atom or a substituent, and at least one of $R_{11}, \ldots,$ or $R_{15}$ represents the following substituent Y. * represents a bond to a benzene ring in General Formula (1).

Substituent Y: a hydroxyl group, a carboxyl group, a group having a carbonyl bond, an acyloxy group, an alkoxycarbonyloxy group, an aryloxycarbonyloxy group, an aryloxycarbonyl group, an alkoxycarbonyl group, a carbamoyl group, or an imido group.

Specific examples of the substituent as each of $R_{11}$ to $R_{15}$ are the same ones as the above-mentioned specific examples of the substituent as each of $R_2$ to $R_4$.

At least one of $R_{11}, \ldots,$ or $R_{15}$ represents the substituent Y.

Specific examples of the group having a carbonyl bond as the substituent Y are the same as the above-mentioned specific examples of the group having a carbonyl bond as the group having a polar group.

The acyl group in the acyloxy group as the substituent Y preferably has 1 to 30 carbon atoms, and more preferably has 1 to 8 carbon atoms.

The alkoxy group in the alkoxycarbonyloxy group as the substituent Y preferably has 1 to 30 carbon atoms, and more preferably has 1 to 8 carbon atoms.

The aryl group in the aryloxycarbonyloxy group as the substituent Y preferably has 6 to 14 carbon atoms, and more preferably 6 to 10 carbon atoms.

The aryl group in the aryloxycarbonyl group as the substituent Y preferably has 6 to 14 carbon atoms, and more preferably 6 to 10 carbon atoms.

The alkoxy group in the alkoxycarbonyl group as the substituent Y preferably 1 to 30 carbon atoms, and more preferably has 1 to 8 carbon atoms.

The imido group as the substituent Y is a group obtained by removing one hydrogen atom from an imide.

The group having a carbonyl bond, the acyloxy group, the alkoxycarbonyloxy group, the aryloxycarbonyloxy group, the aryloxycarbonyl group, the alkoxycarbonyl group, and the imido group as the substituent Y may further have a substituent.

Examples of the substituent to be further contained include the respective groups described above as the specific examples of the substituents which may be further contained in each of $R_1$ and $R_5$ as mentioned above.

n in the anionic moiety of General Formula (1) represents the number of anions. n represents an integer of 1 or more. The upper limit value of n is not particularly limited, but is, for example, 4.

n is preferably 1.

$M^{n+}$ in General Formula (1) represents a cation.

n in the cationic moiety of General Formula (1) represents a valence of the cation. n represents an integer of 1 or more. The upper limit value of n is not particularly limited, but is, for example, 4.

n is preferably 1.

The cation as $M^{n+}$ is not particularly limited as long as it is a monovalent or higher cation, but is preferably an onium cation, and a cation represented by General Formula (ZIA) or General Formula (ZIIA) is preferable.

(ZIA)

(ZIIA)

In General Formula (ZIA), $R_{201}$, $R_{202}$, and $R_{203}$ each independently represent an organic group.

The organic group as each of $R_{201}$, $R_{202}$, and $R_{203}$ generally has 1 to 30 carbon atoms, and preferably has 1 to 20 carbon atoms.

In addition, two of $R_{201}$ to $R_{203}$ may be bonded to each other to form a ring structure, and the ring may include an oxygen atom, a sulfur atom, an ester bond, an amide bond, or a carbonyl group. Examples of the group formed by the bonding of two of $R_{201}$ to $R_{203}$ include an alkylene group (for example, a butylene group and a pentylene group), and —$CH_2$—$CH_2O$—$CH_2$—$CH_2$—.

Preferred aspects of the cation as General Formula (ZIA) include a cation (ZI-11), a cation (ZI-12), a cation represented by General Formula (ZI-13) (cation (ZI-13)), and a cation represented by General Formula (ZI-14) (cation (ZI-14)), each of which will be described later.

The divalent or higher cation in a case where n is 2 or more may be a cation having a plurality of structures represented by General Formula (ZIA). Examples of such the cation include a divalent cation having a structure in which at least one of $R_{201}$, $R_{202}$, or $R_{203}$ of a cation represented by General Formula (ZIA) and at least one of $R_{201}$, $R_{202}$, or $R_{203}$ of another cation represented by General Formula (ZIA) are bonded via a single bond or a linking group.

First, the cation (ZI-11) will be described.

The cation (ZI-11) is a cation, that is, an arylsulfonium cation in which at least one of $R_{201}, \ldots,$ or $R_{203}$ of General Formula (ZIA) is an aryl group.

In the arylsulfonium cation, any of $R_{201}$ to $R_{203}$ may be an aryl group, or some of $R_{201}$ to $R_{203}$ may be an aryl group, and the rest may be an alkyl group or a cycloalkyl group.

Examples of the arylsulfonium cation include a triarylsulfonium cation, a diarylalkylsulfonium cation, an aryldialkylsulfonium cation, a diarylcycloalkylsulfonium cation, and an aryldicycloalkylsulfonium cation.

As the aryl group included in the arylsulfonium cation, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium cation has two or more aryl groups, the two or more aryl groups may be the same as or different from each other.

The alkyl group or the cycloalkyl group contained in the arylsulfonium cation, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of each of $R_{201}$ to $R_{203}$ may each independently have an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group, a lactone ring group, or a phenylthio group as a substituent.

Examples of the lactone ring group include groups obtained by removing a hydrogen atom from the above-mentioned structure represented by any of (KA-1-1) to (KA-1-17).

Next, the cation (ZI-12) will be described.

The cation (ZI-12) is a compound in which $R_{201}$ to $R_{203}$ in Formula (ZIA) each independently represent an organic group having no aromatic ring. Here, the aromatic ring also includes an aromatic ring including a heteroatom.

The organic group having no aromatic ring as each of $R_{201}$ to $R_{203}$ generally has 1 to 30 carbon atoms, and preferably has 1 to 20 carbon atoms.

$R_{201}$ to $R_{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Preferred examples of the alkyl group and the cycloalkyl group of each of $R_{201}$ to $R_{203}$ include a linear alkyl group having 1 to 10 carbon atoms or branched alkyl group having 3 to 10 carbon atoms (for example, a methyl group, an ethyl group, a propyl group, a butyl group, and a pentyl group), and a cycloalkyl group having 3 to 10 carbon atoms (for example, a cyclopentyl group, a cyclohexyl group, and a norbornyl group).

$R_{201}$ to $R_{203}$ may be further substituted with a halogen atom, an alkoxy group (for example, having 1 to 5 carbon atoms), a hydroxyl group, a cyano group, or a nitro group.

Next, the cation (ZI-13) will be described.

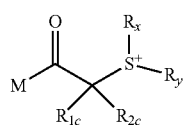

(ZI-13)

In General Formula (ZI-13), M represents an alkyl group, a cycloalkyl group, or an aryl group, and in a case where M has a ring structure, the ring structure may include at least one of an oxygen atom, a sulfur atom, an ester bond, an amide bond, or a carbon-carbon double bond. $R_{1c}$ and $R_{2c}$ each independently represent a hydrogen atom, an alkyl group, a cycloalkyl group, a halogen atom, a cyano group, or an aryl group. $R_{1c}$ and $R_{2c}$ may be bonded to each other to form a ring. $R_x$ and $R_y$ each independently represent an alkyl group, a cycloalkyl group, or an alkenyl group. $R_x$ and $R_y$ may be bonded to each other to form a ring. In addition, at least two selected from M, $R_{1c}$, or $R_{2c}$ may be bonded to each other to form a ring structure, and the ring structure may include a carbon-carbon double bond.

In General Formula (ZI-13), as the alkyl group and the cycloalkyl group represented by M, a linear alkyl group having 1 to 15 carbon atoms (preferably having 1 to 10 carbon atoms), a branched alkyl group having 3 to 15 carbon atoms (preferably having 3 to 10 carbon atoms), or a cycloalkyl group having 3 to 15 carbon atoms (preferably having 1 to 10 carbon atoms) is preferable, and specific examples thereof include a methyl group, an ethyl group, a propyl group, an n-butyl group, a sec-butyl group, a t-butyl group, a cyclopropyl group, a cyclobutyl group, a cyclohexyl group, and a norbornyl group.

The aryl group represented by M is preferably a phenyl group or a naphthyl group, and more preferably the phenyl group. The aryl group may be an aryl group which has a heterocyclic structure having an oxygen atom, a sulfur atom, or the like. Examples of the heterocyclic structure include a furan ring, a thiophene ring, a benzofuran ring, and a benzothiophene ring.

M may further have a substituent. In this aspect, examples of M include a benzyl group.

In addition, in a case where M has a ring structure, the ring structure may include at least one of an oxygen atom, a sulfur atom, an ester bond, an amide bond, or a carbon-carbon double bond.

Examples of the alkyl group, the cycloalkyl group, and the aryl group represented by each of $R_{1c}$ and $R_{2c}$ include the same ones as those of M as mentioned above, and preferred aspects thereof are also the same. Further, $R_{1c}$ and $R_{2c}$ may be bonded to each other to form a ring.

Examples of the halogen atom represented by each of $R_{1c}$ and $R_{2c}$ include a fluorine atom, a chlorine atom, a bromine atom, and an iodine atom.

Examples of the alkyl group and the cycloalkyl group represented by each of $R_x$ and $R_y$ include the same ones as those of M as mentioned above, and preferred aspects thereof are also the same.

The alkenyl group represented by each of $R_x$ and $R_y$ is preferably an allyl group or a vinyl group.

$R_x$ and $R_y$ may further have a substituent. In this aspect, examples of each of $R_x$ and $R_y$ include a 2-oxoalkyl group or an alkoxycarbonylalkyl group.

Examples of the 2-oxoalkyl group represented by each of $R_x$ and $R_y$ include those having 1 to 15 carbon atoms (preferably having 1 to 10 carbon atoms), and specifically a 2-oxopropyl group and a 2-oxobutyl group.

Examples of the alkoxycarbonylalkyl group represented by each of $R_x$ and $R_y$ include those having 1 to 15 carbon atoms (preferably having 1 to 10 carbon atoms). In addition, $R_x$ and $R_y$ may be bonded to each other to form a ring.

The ring structure formed by the mutual linkage of $R_x$ and $R_y$ may include an oxygen atom, a sulfur atom, an ester bond, an amide bond, or a carbon-carbon double bond.

In General Formula (ZI-13), M and $R_{1c}$ may be bonded to each other to form a ring structure, and the ring structure formed may include a carbon-carbon double bond.

Among those, the cation (ZI-13) is preferably a cation (ZI-13A).

The cation (ZI-13A) is a phenacylsulfonium cation represented by General Formula (ZI-13A).

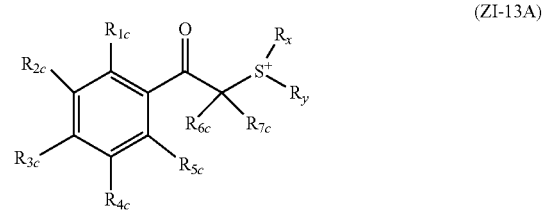

(ZI-13A)

In General Formula (ZI-13A), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ have the same definitions as $R_{1c}$ and $R_{2c}$ in General Formula (ZI-13) as mentioned above, respectively, and preferred aspects thereof are also the same.

$R_x$ and $R_y$ have the same definitions as $R_x$ and $R_y$ in General Formula (ZI-13) as mentioned above, respectively, and preferred aspects thereof are also the same.

Any two or more of $R_{1c}, \ldots,$ or $R_{5c}$, or $R_x$ and $R_y$ may be bonded to each other to form a ring structure, and the ring structure may each independently include an oxygen atom, a sulfur atom, an ester bond, an amide bond, or a carbon-carbon double bond. Furthermore, $R_{5c}$ and $R_{6c}$, or $R_{5c}$ and $R_x$ may be bonded to each other to form a ring structure, and the ring structure may each independently include a carbon-carbon double bond. In addition, $R_{6c}$ and $R_{7c}$ may be bonded to each other to form a ring structure.

Examples of the ring structure include an aromatic or non-aromatic hydrocarbon ring, an aromatic or non-aromatic heterocycle, and a polycyclic fused ring in which two or more of these rings are combined with each other. Examples of the ring structure include a 3- to 10-membered ring and the ring structure is preferably a 4- to 8-membered ring, and more preferably a 5- or 6-membered ring.

Examples of the group formed by the bonding of any two or more of $R_{1c}, \ldots,$ or $R_{5c}$, $R_{6c}$ and $R_{7c}$, and $R_x$ and $R_y$ include a butylene group and a pentylene group.

As the group formed by the bonding of $R_{5c}$ and $R_{6c}$, and $R_{5c}$ and $R_x$, a single bond or an alkylene group is preferable. Examples of the alkylene group include a methylene group and an ethylene group.

Next, the cation (ZI-14) will be described.

The cation (ZI-14) is represented by General Formula (ZI-14).

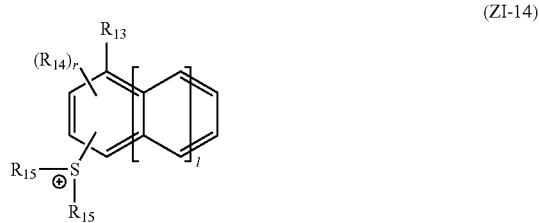

(ZI-14)

In General Formula (ZI-14), l represents an integer of 0 to 2.

r represents an integer of 0 to 8.

$R_{13}$ represents a group having a hydrogen atom, a fluorine atom, a hydroxyl group, an alkyl group, a cycloalkyl group, an alkoxy group, an alkoxycarbonyl group, or a group having a monocyclic or polycyclic cycloalkyl skeleton. These groups may have a substituent.

In a case where a plurality of $R_{14}$'s are present, $R_{14}$'s each independently represent an alkyl group, a cycloalkyl group, an alkoxy group, an alkylsulfonyl group, a cycloalkylsulfonyl group, an alkylcarbonyl group, an alkoxycarbonyl group, or an alkoxy group having a monocyclic or polycyclic cycloalkyl skeleton. These groups may have a substituent.

$R_{15}$'s each independently represent an alkyl group, a cycloalkyl group, or a naphthyl group. These groups may have a substituent. Two of $R_{15}$'s may be bonded to each other to forma ring. In a case where two of $R_{15}$'s are bonded to each other to form a ring, the ring skeleton may include a heteroatom such as an oxygen atom and a nitrogen atom. In one aspect, it is preferable that two of $R_{15}$'s are alkylene groups and are bonded to each other to form a ring structure.

In General Formula (ZI-14), the alkyl group of each of $R_{13}$, $R_{14}$, and $R_{15}$ is linear or branched. The alkyl group preferably has 1 to 10 carbon atoms. As the alkyl group, a methyl group, an ethyl group, an n-butyl group, a t-butyl group, or the like is more preferable.

Next, General Formula (ZIIA) will be described.

In General Formula (ZIIA), $R_{204}$ and $R_{205}$ each independently represent an aryl group, an alkyl group, or a cycloalkyl group.

As the aryl group of each of $R_{204}$ and $R_{205}$, a phenyl group or a naphthyl group is preferable, and the phenyl group is more preferable. The aryl group of each of $R_{204}$ and $R_{205}$ may be an aryl group which has a heterocyclic structure having an oxygen atom, a nitrogen atom, a sulfur atom, or the like. Examples of the skeleton of the aryl group having a heterocyclic structure include pyrrole, furan, thiophene, indole, benzofuran, and benzothiophene.

As the alkyl group and the cycloalkyl group of each of $R_{204}$ and $R_{205}$, a linear alkyl group having 1 to 10 carbon atoms or branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R_{204}$ and $R_{205}$ may each independently have a substituent. Examples of the substituent which may be contained in each of the aryl group, the alkyl group, and the cycloalkyl group of each of $R_{204}$ to $R_{207}$ include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, a lactone ring group, and a phenylthio group.

Examples of the lactone ring group include groups obtained by removing a hydrogen atom from the above-mentioned structure represented by any of (KA-1-1) to (KA-1-17).

Preferred examples of $M^{n+}$ (cation) in General Formula (1) are shown below, but the present invention is not limited thereto. Me represents a methyl group and Bu represents an n-butyl group.

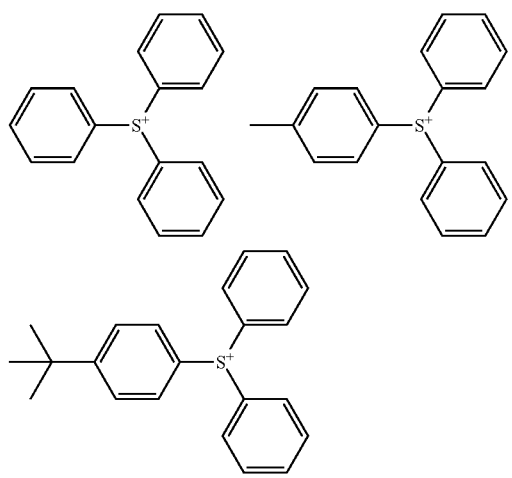

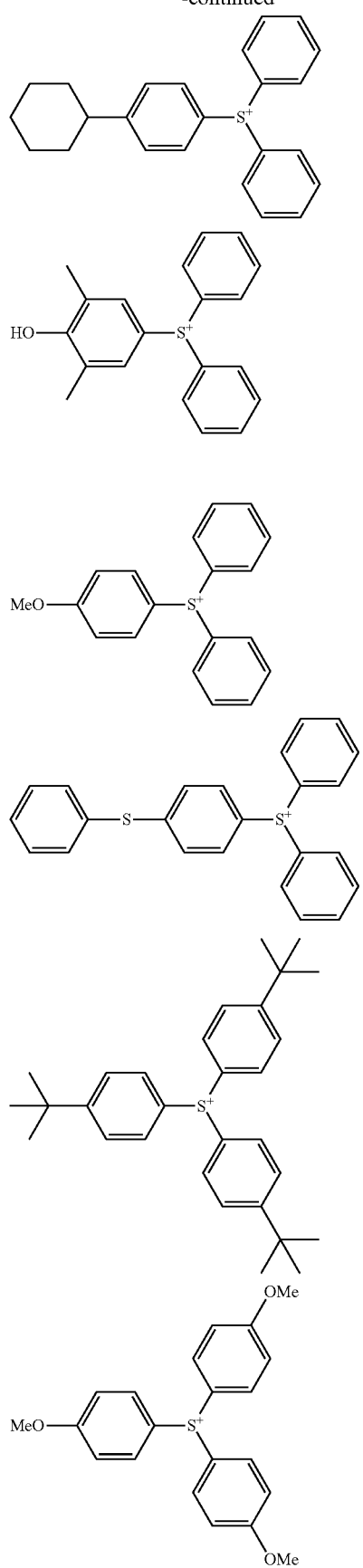
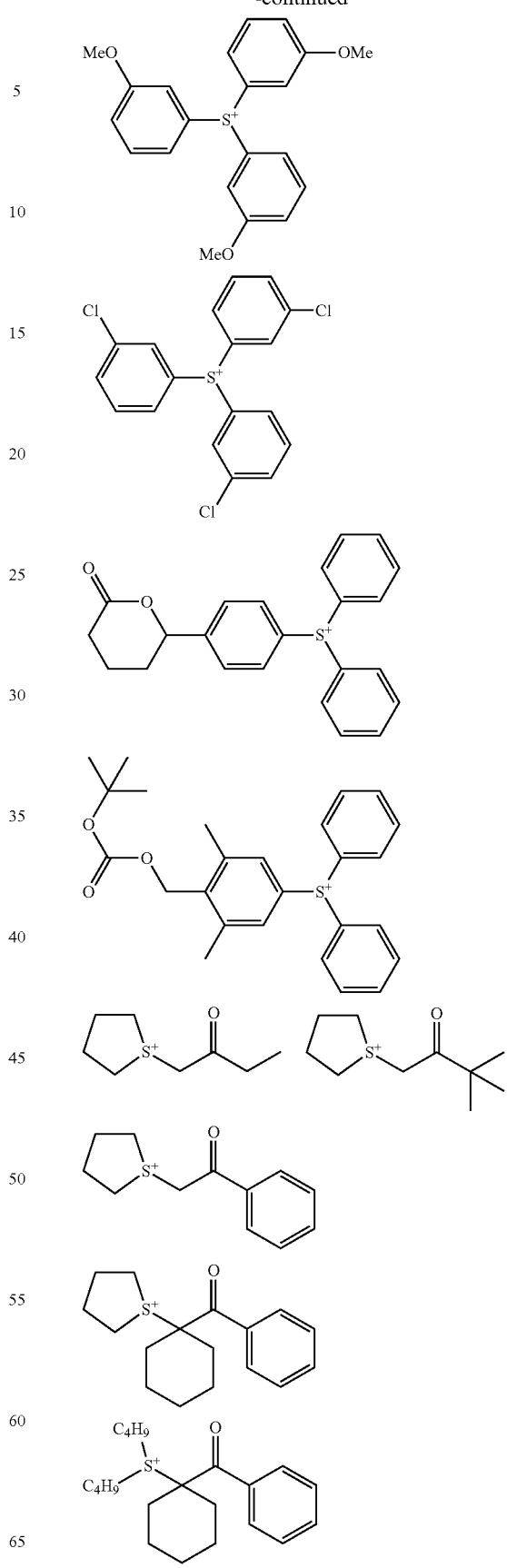

55
-continued
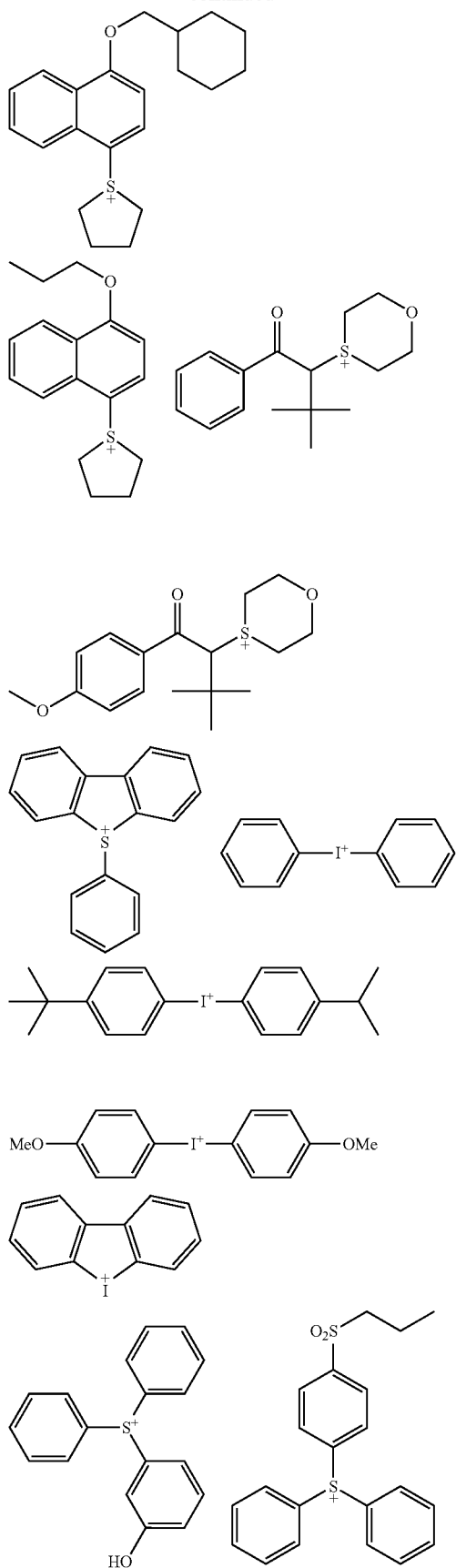
56
-continued
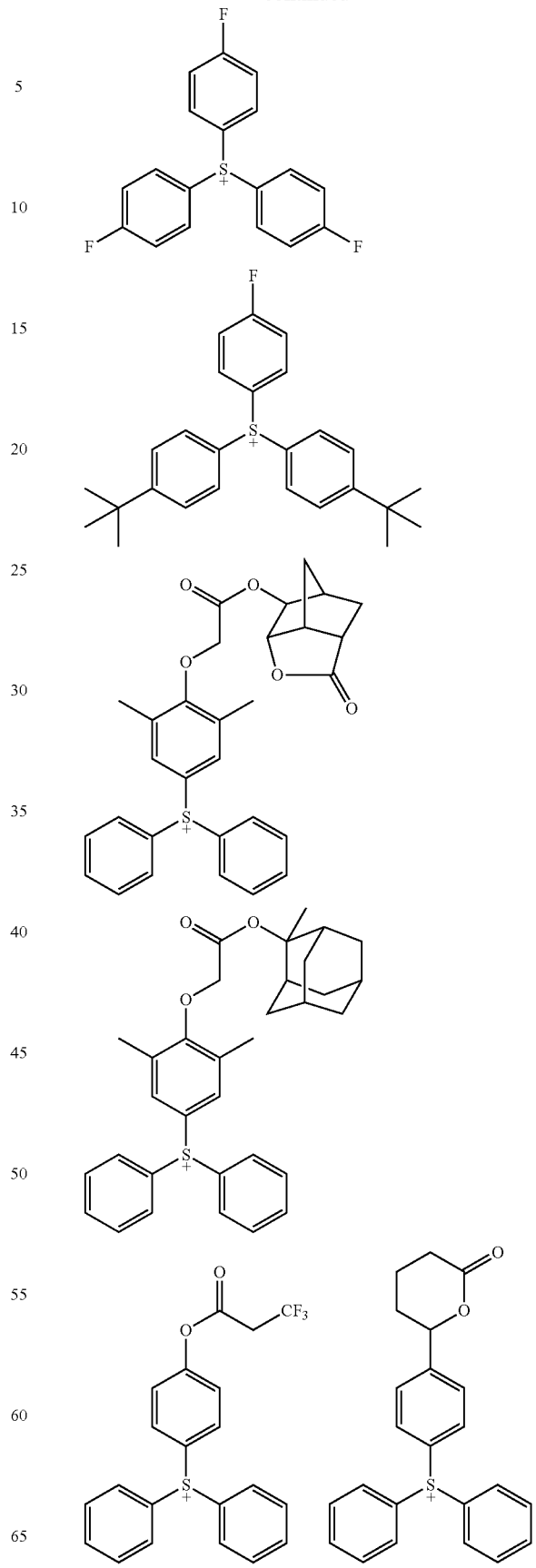

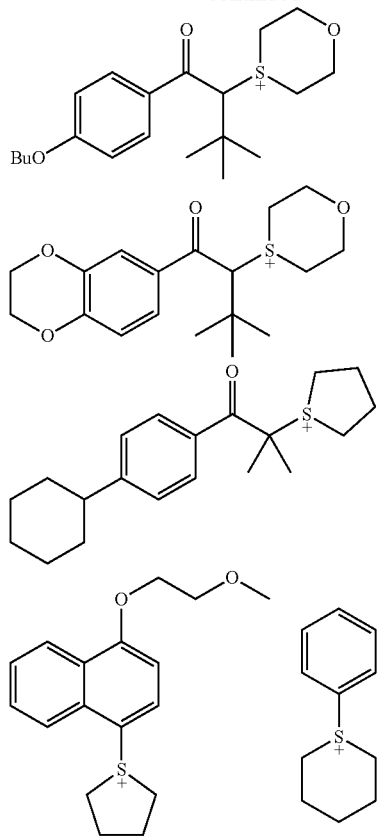
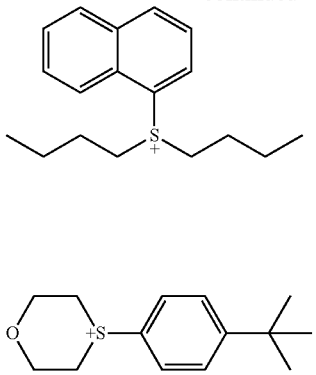
Preferred examples of the anionic moiety in General Formula (1) are shown below, but the present invention is not limited thereto. Me represents a methyl group.
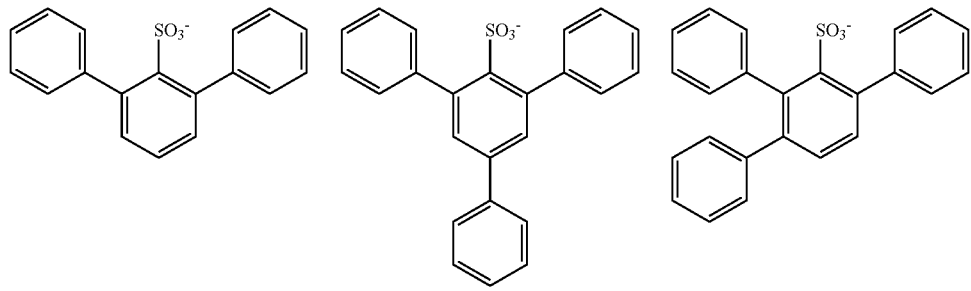
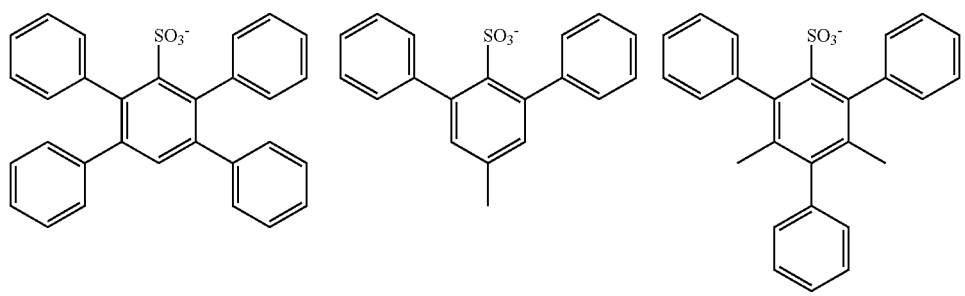

-continued
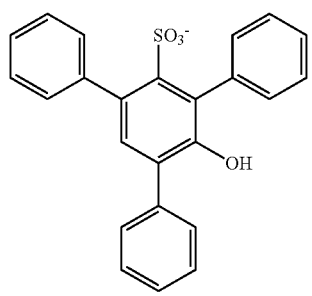 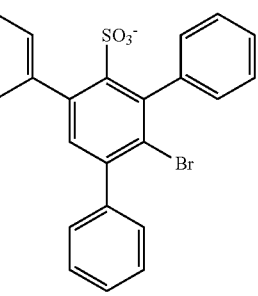 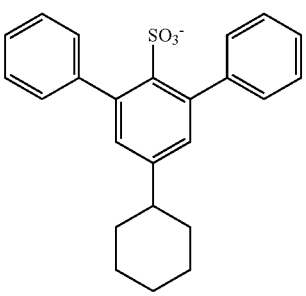
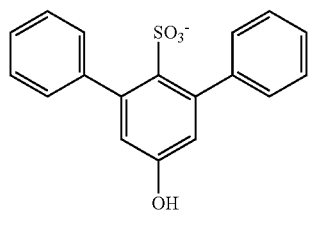 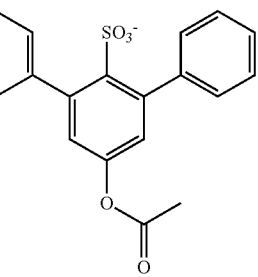 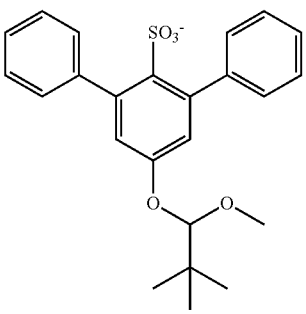
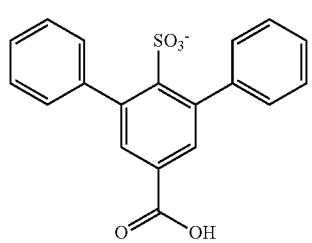 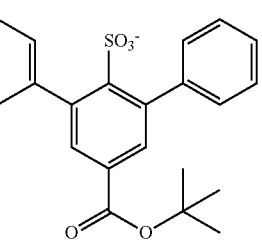 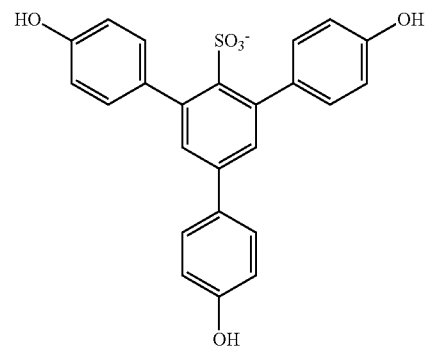
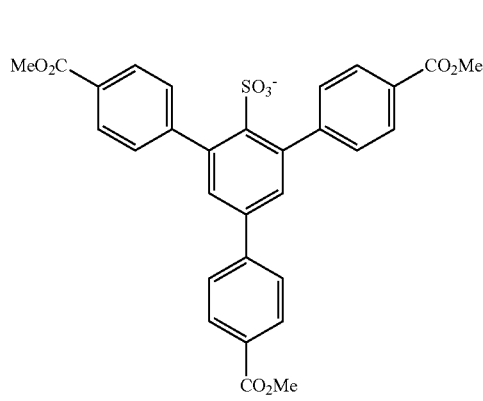 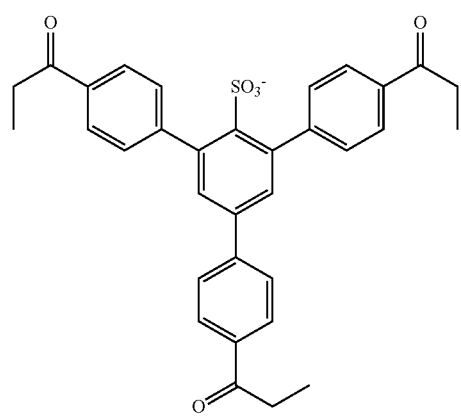

61
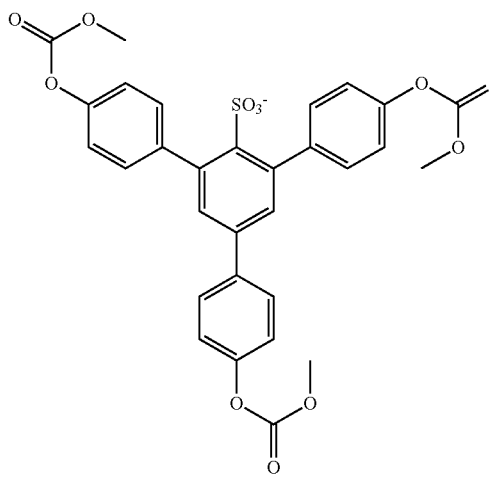
-continued
62
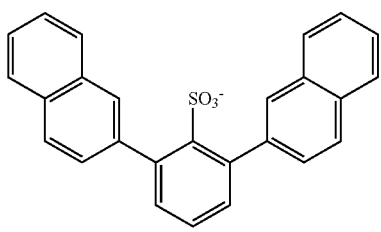
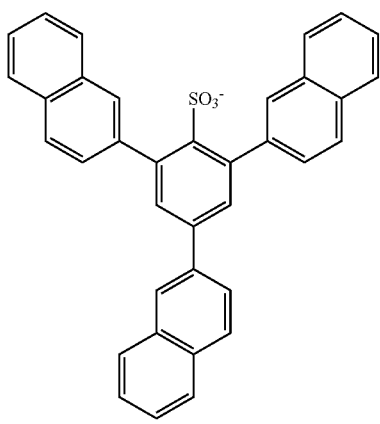
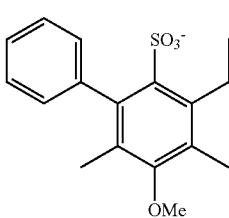
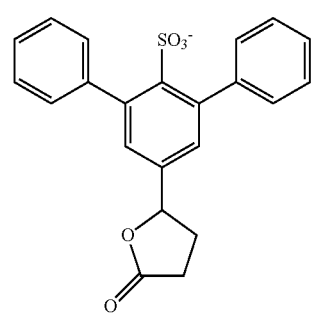
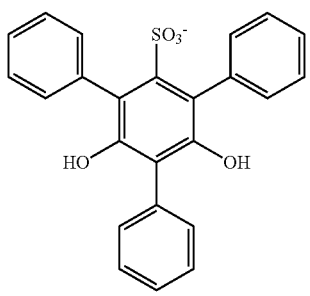
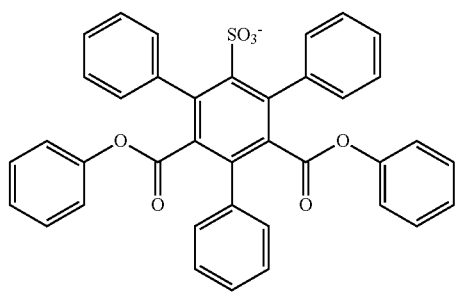
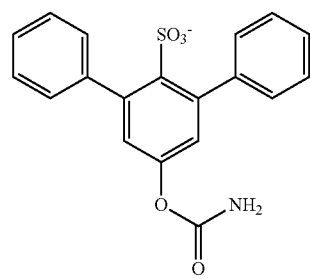
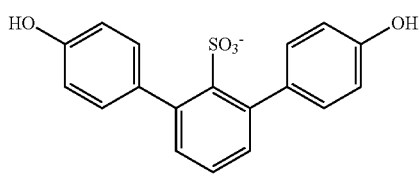
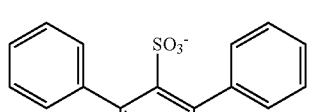
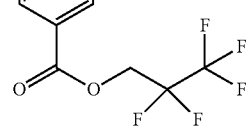

-continued
63
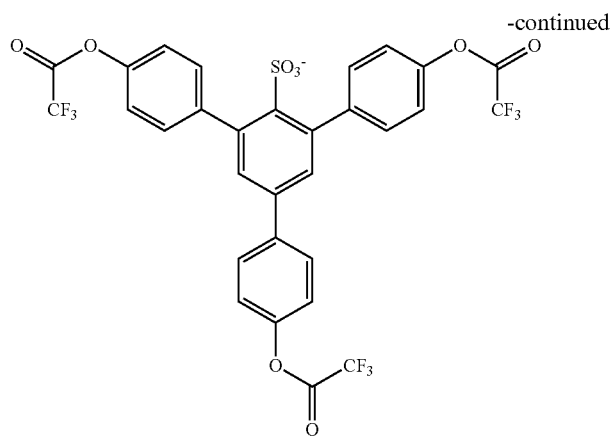
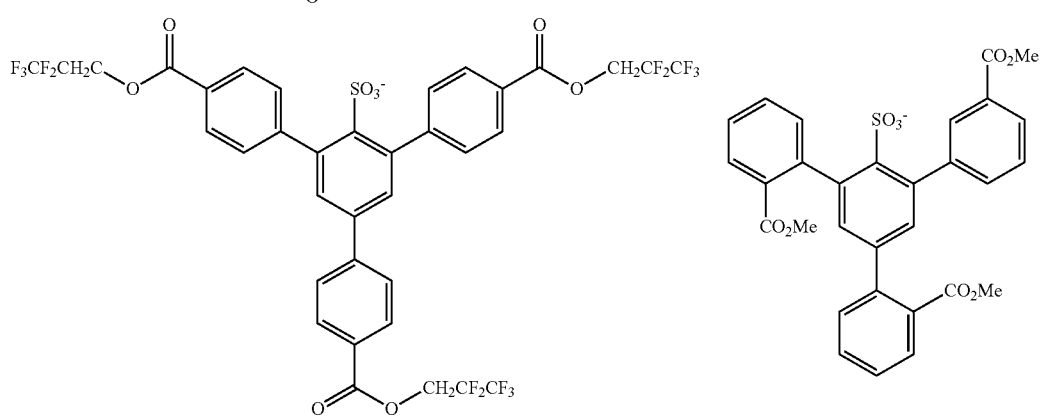
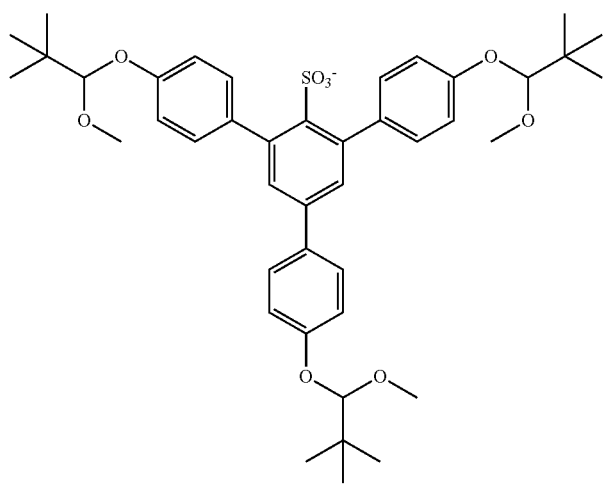
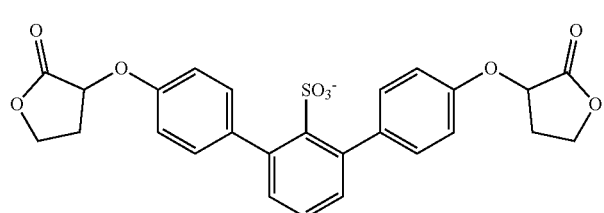
64
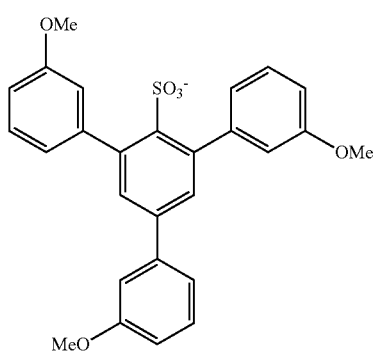
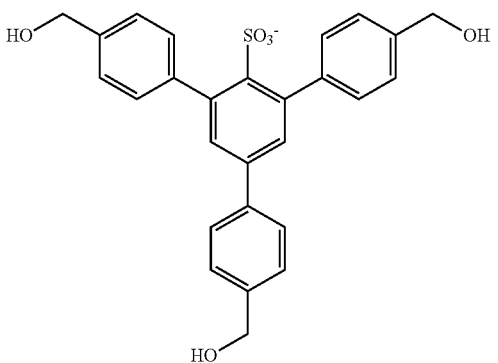

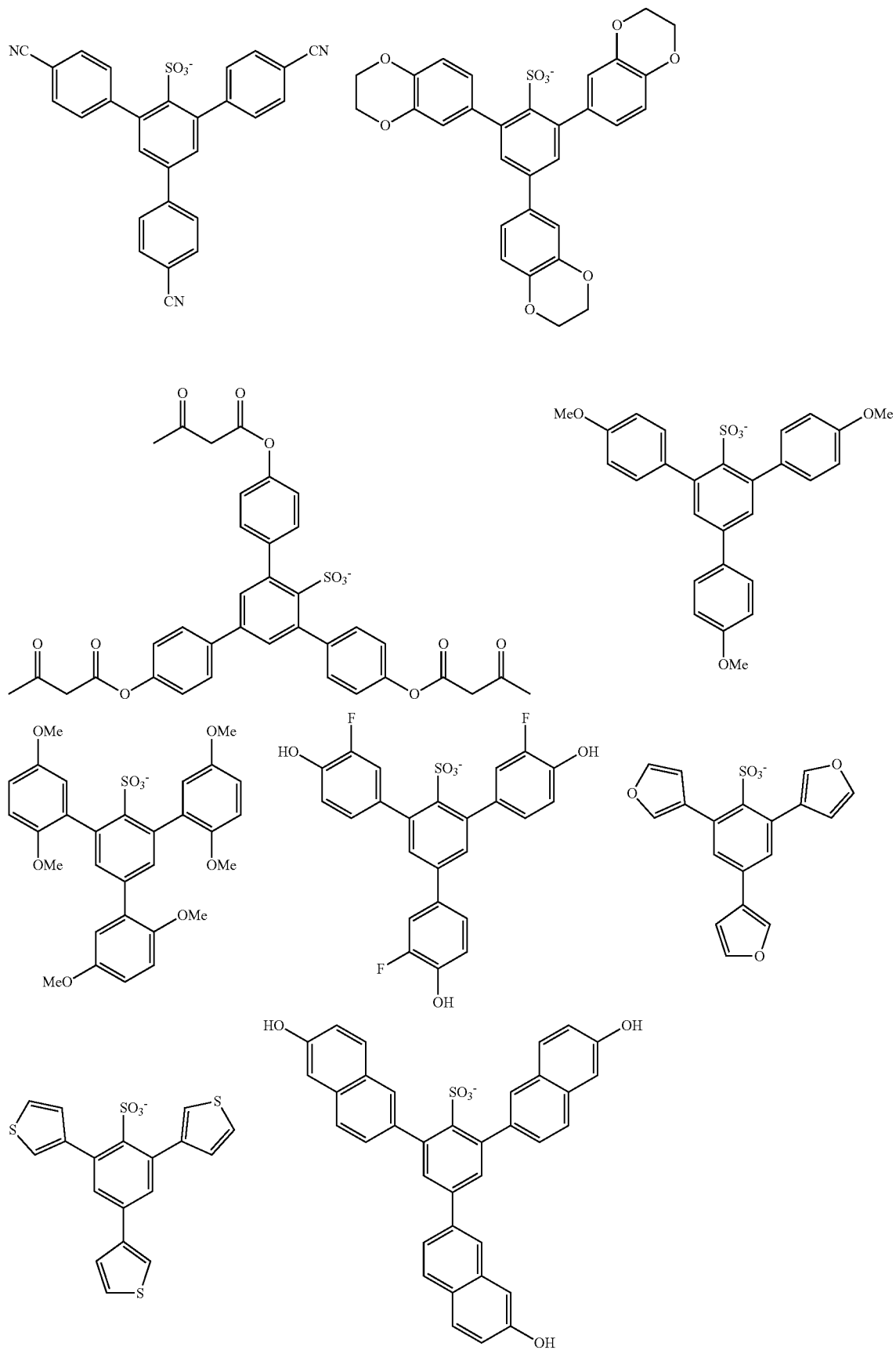

-continued
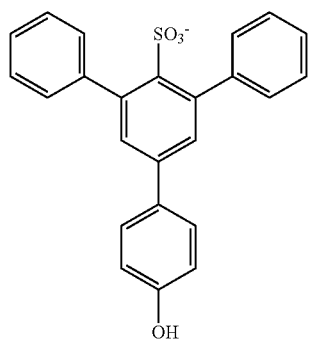 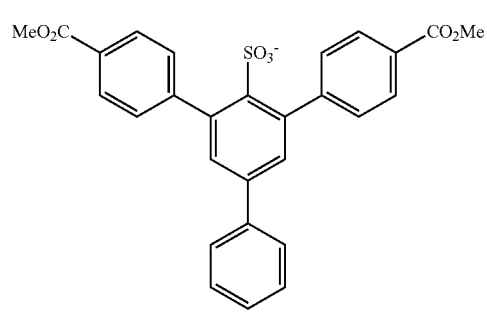
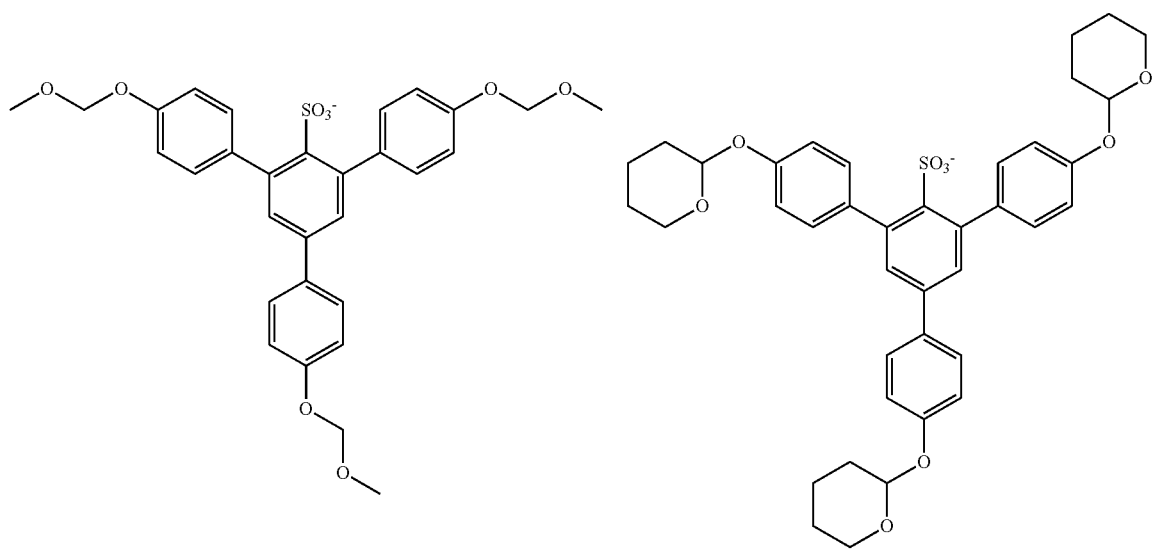
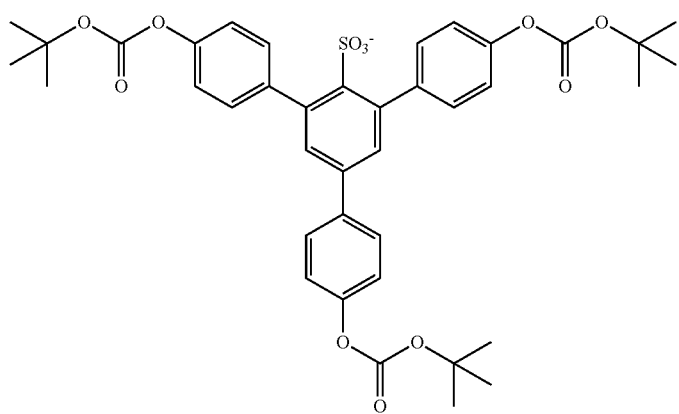

-continued
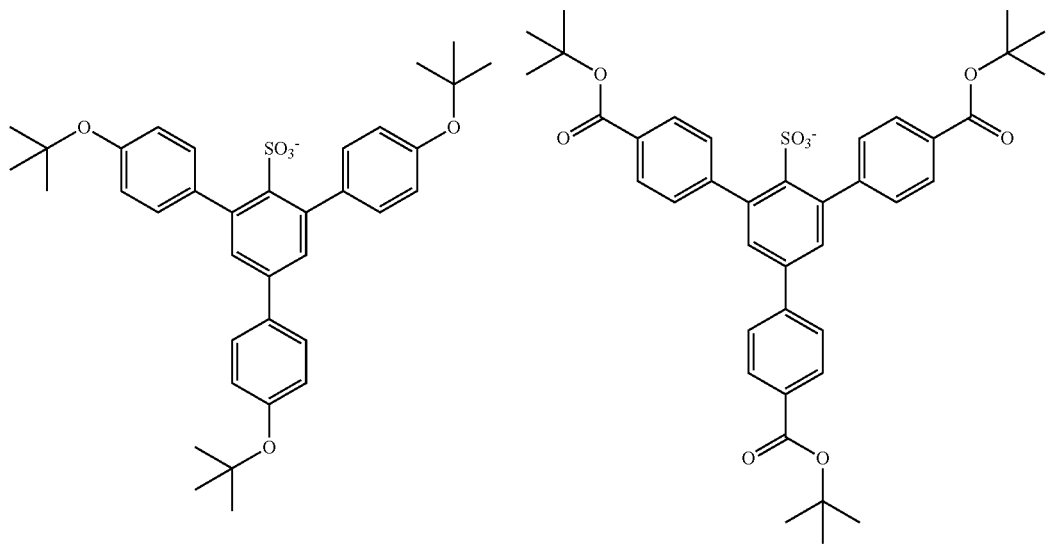
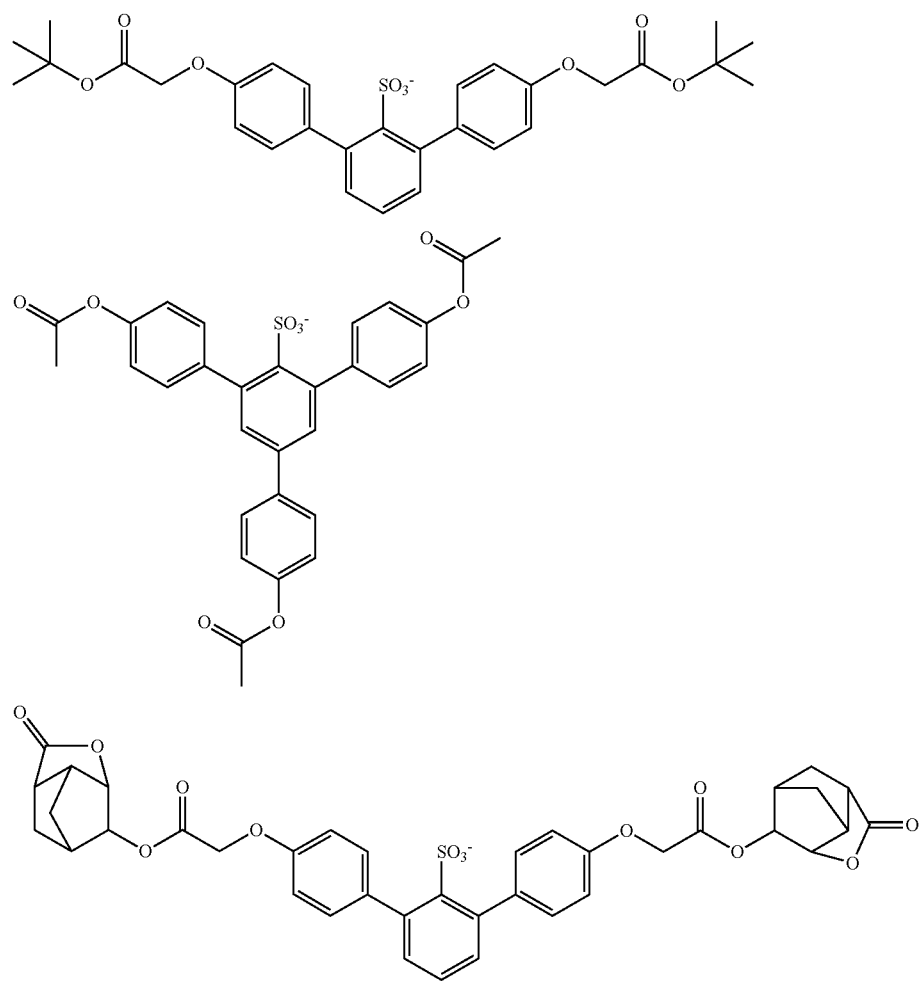

It is preferable that the pKa of an acid generated by the compound (B) is from −10 to 5.

The acid dissociation constant (pKa) refers to a pKa in an aqueous solution, and is defined in Chemical Handbook (II)(Revised 4$^{th}$ Edition, 1993, compiled by the Chemical Society of Japan, Maruzen Company, Ltd.). A lower value of the pKa indicates higher acid strength. Specifically, the pKa in an aqueous solution can be actually measured by using an infinite-dilution aqueous solution and measuring the acid dissociation constant at 25° C. Alternatively, the acid dissociation constant pKa can also be determined using the following software package 1 by computation from a value with respect to a Hammett substituent constant and the database of publicly known literature values. Any of the values of pKa described in the present specification indicate values determined by computation using the software package.

Software Package 1: Advanced Chemistry Development (ACD/Labs) Software V 8.14 for Solaris (1994-2007 ACD/Labs).

Preferred examples of the compound (B) are shown below, but the present invention is not limited thereto. Me represents a methyl group. Moreover, preferred examples of the compound (B) also include a compound obtained by combination of the anion and the cation.

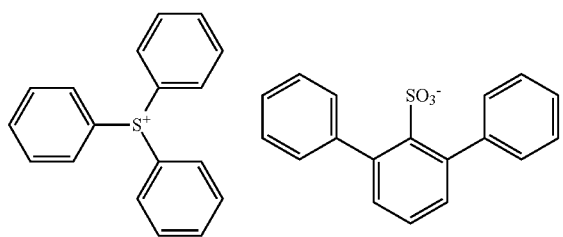

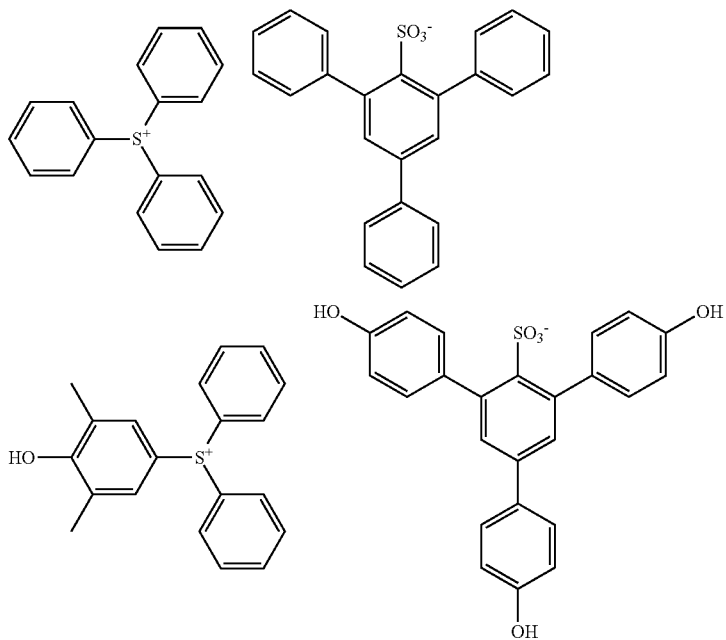

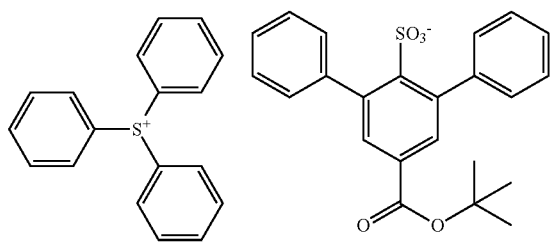

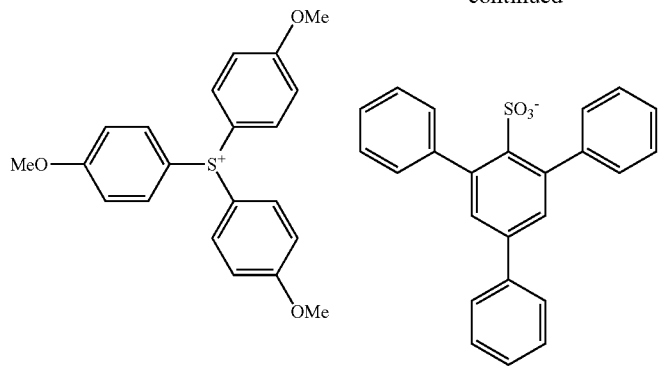
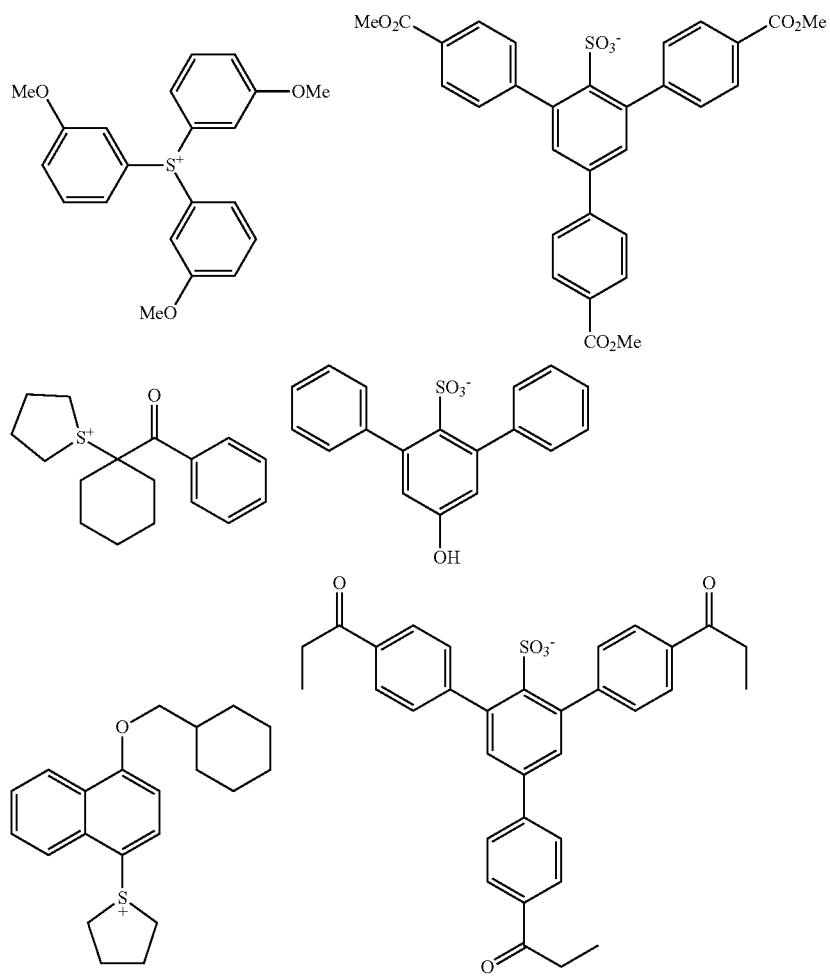
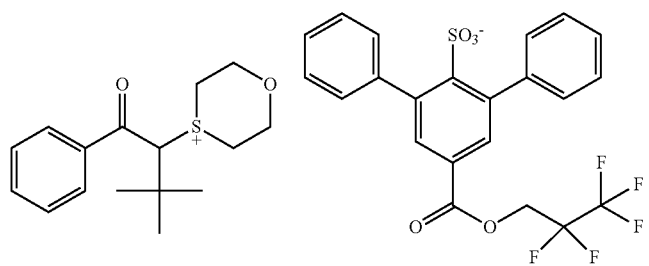

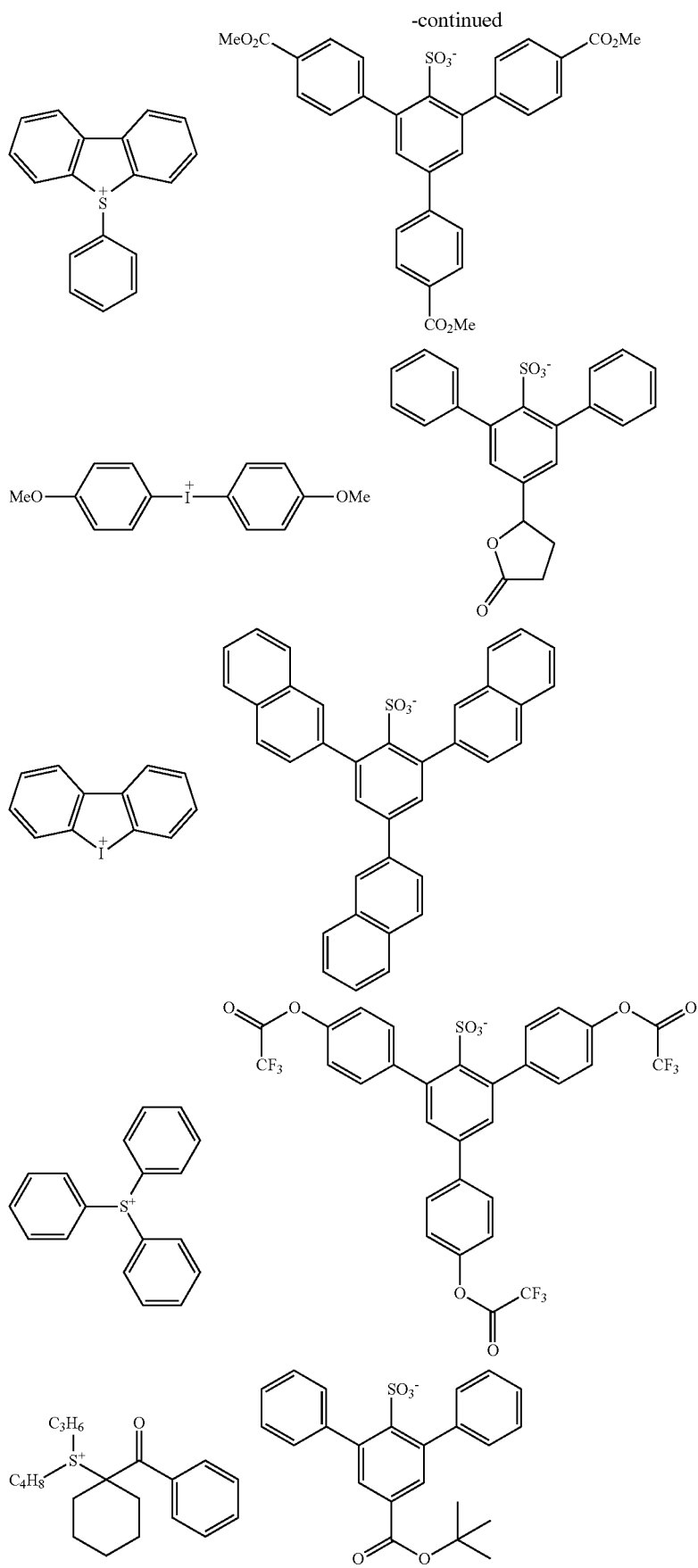

-continued
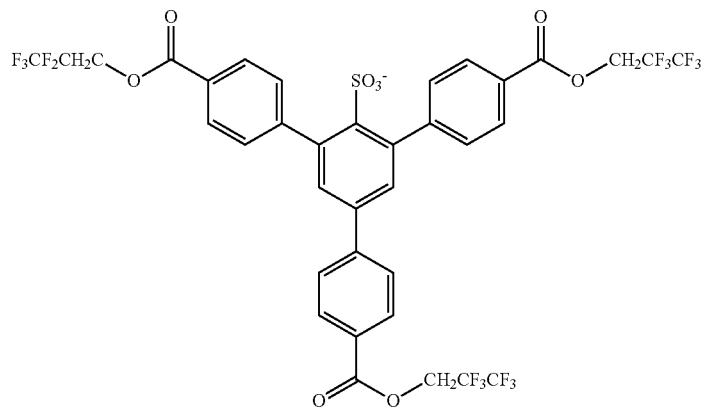
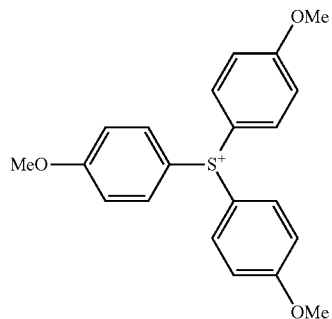
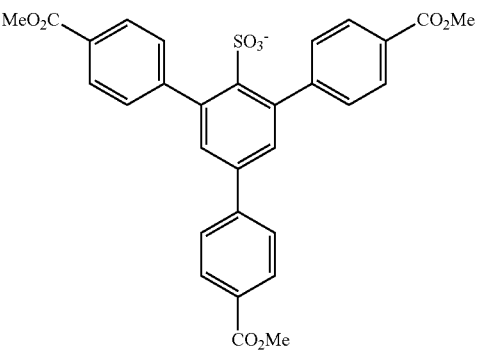
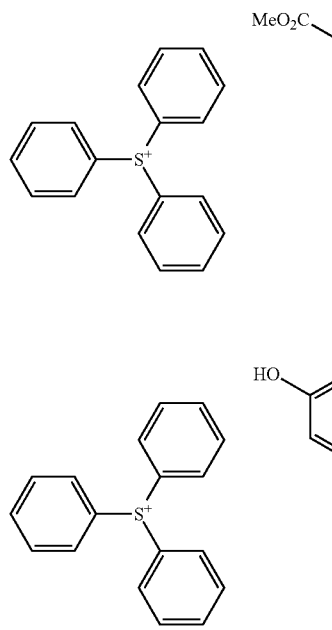
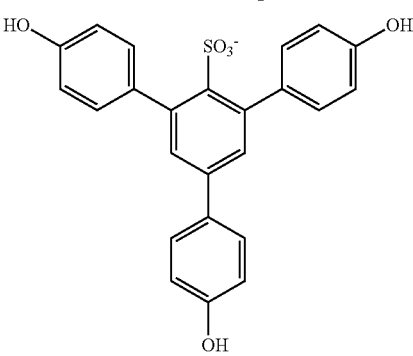
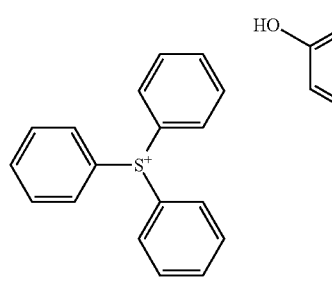
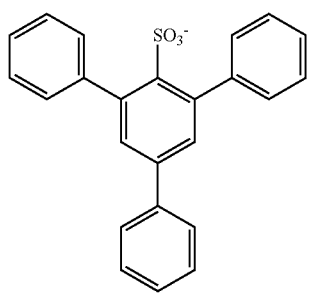
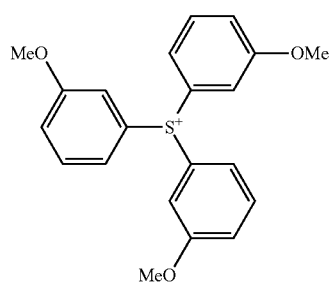
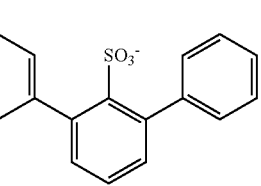
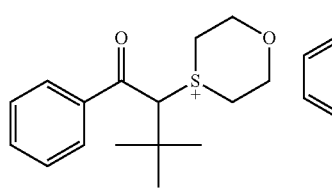

-continued
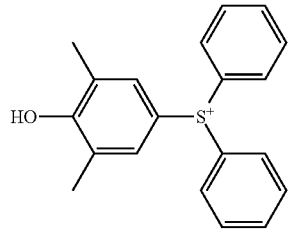
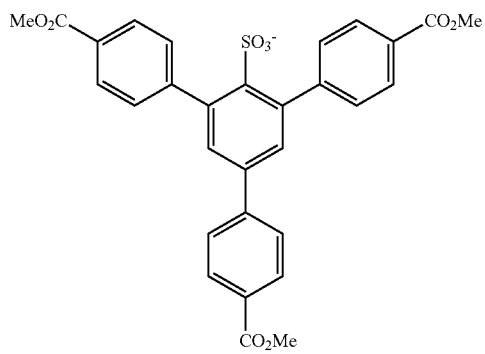
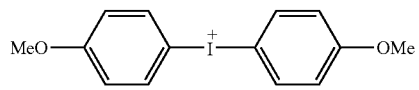
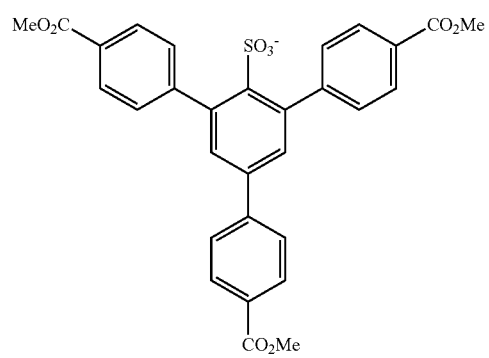
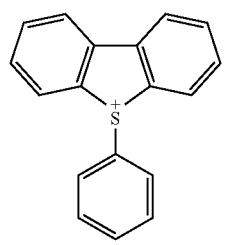
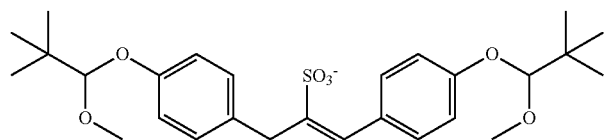
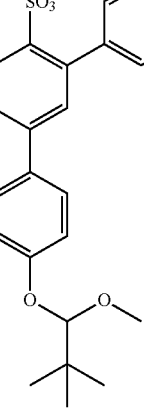
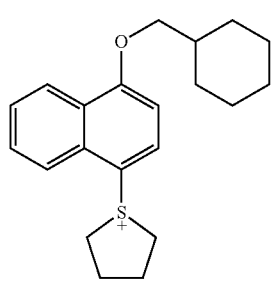
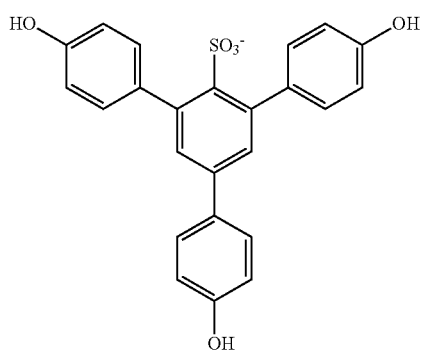

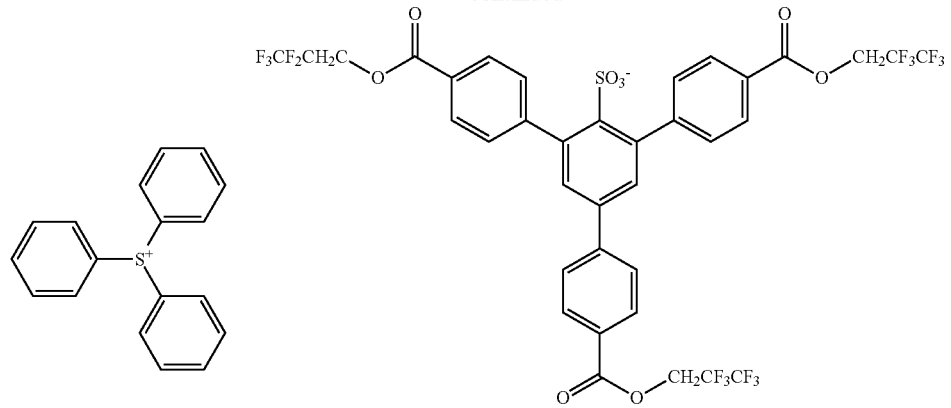
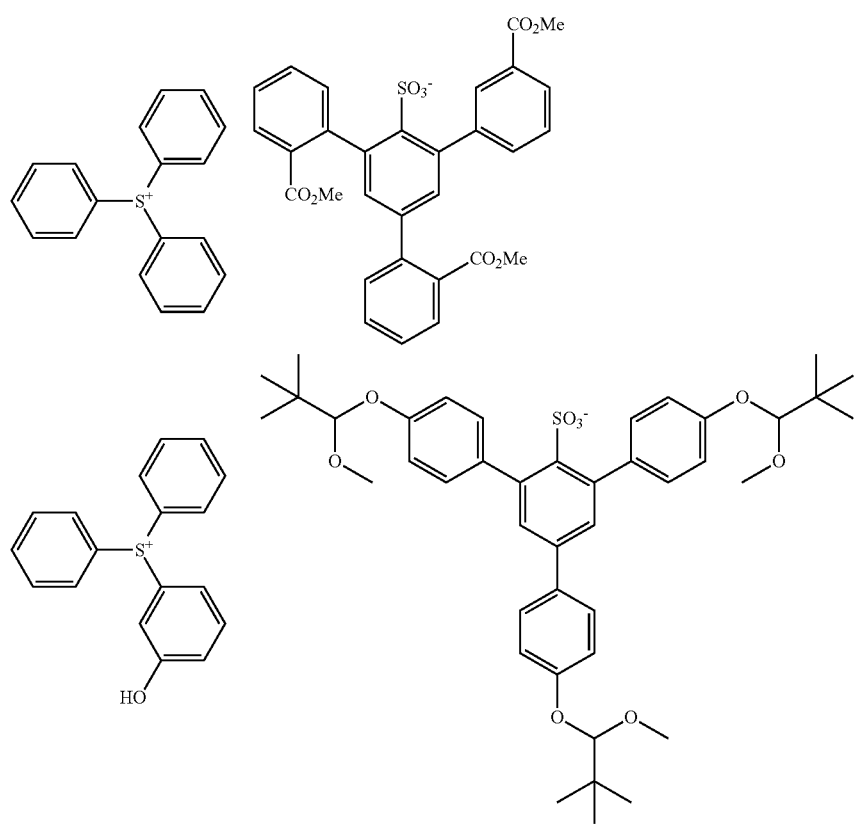
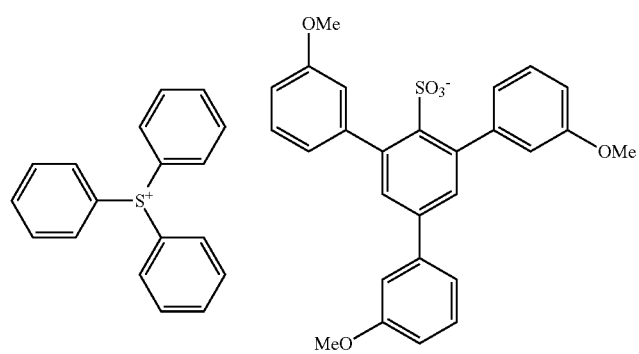

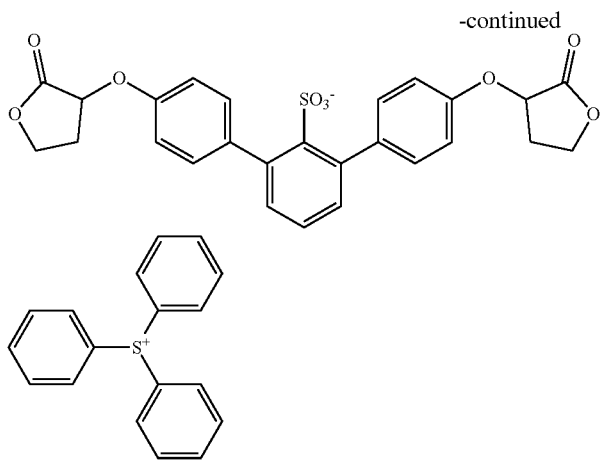

The compound (B) can be synthesized, for example, by a method using a coupling reaction.

For the coupling reaction, for example, Suzuki coupling or the like can be applied. The counter cation can be converted into a desired cation $M^{n+}$ by, for example, a known anion exchange method or a conversion method using an ion exchange resin, as described in JP1994-184170A (JP-H06-184170A).

Examples of the coupling reaction include the following reaction.

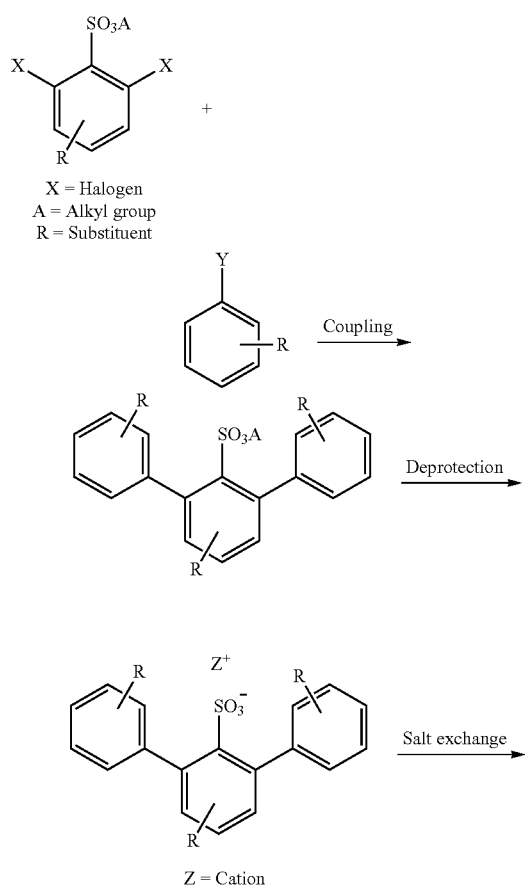

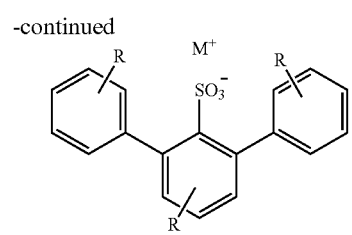

X represents a halogen atom and A represents an alkyl group. R represents a substituent.

Y represents a group that forms a compound XY by a coupling reaction.

The compound (B) may be used singly or in combination of two or more kinds thereof.

The content of the compound (B) (in a case where a plurality of the compounds (B) are present, a total content thereof) in the composition of the embodiment of the present invention is preferably 0.1% to 35% by mass, more preferably 0.5% to 25% by mass, still more preferably 1% to 20%/by mass, and particularly preferably 5% to 20% by mass, with respect to a total solid content of the composition.

[(B') Compound that Generates Acid upon Irradiation with Actinic Rays or Radiation Other than Compound (B)]

The composition of the embodiment of the present invention can contain a compound that generates an acid upon irradiation with actinic rays or radiation other than the compound (B) as long as the effect of the present invention is not impaired.

[Acid Diffusion Control Agent]

The composition of the embodiment of the present invention preferably contains an acid diffusion control agent. The acid diffusion control agent acts as a quencher that suppresses a reaction of the acid-decomposable resin in the unexposed area by excessive generated acids by trapping the acids generated from a photoacid generator and the like upon exposure.

For example, a basic compound (DA), a basic compound (DB) having basicity reduced or lost upon irradiation with actinic rays or radiation, an onium salt (DC) which is a weak acid relative to an acid generator, a low-molecular-weight compound (DD) having a nitrogen atom and a group that is eliminated by an action of an acid, an onium salt compound (DE) having a nitrogen atom in the cationic moiety, can be used as the acid diffusion control agent. In the composition of the embodiment of the present invention, a known acid diffusion control agent can be appropriately used. For example, the known compounds disclosed in paragraphs [0627] to [0664] of the specification of US2016/0070167A, paragraphs [0095] to [0187] of the specification of US2015/0004544A1, paragraphs [0403] to [0423] of the specification of US2016/0237190A1, and paragraphs [0259] to [0328] of the specification of US2016/0274458A1 can be suitably used as the acid diffusion control agent.

As the basic compound (DA), compounds having structures represented by General Formulae (A) to (E) are preferable.

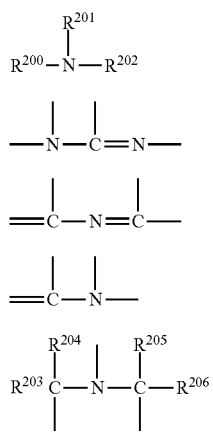

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (having 6 to 20 carbon atoms). $R^{201}$ and $R^{202}$ may be bonded to each other to form a ring.

$R^{203}$, $R^{204}$, $R^{205}$, and $R^{206}$ may be the same as or different from each other and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl groups in each of General Formulae (A) and (E) are more preferably unsubstituted.

As the basic compound (DA), thiazole, benzothiazole, oxazole, benzoxazole, guanidine, aminopyrrolidine, pyrazole, pyrazoline, piperazine, aminomorpholine, aminoalkylmorpholine, piperidine, or compounds having these structures are preferable; and a compound having a thiazole structure, a benzothiazole structure, an oxazole structure, a benzoxazole structure, an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond, or the like is more preferable.

The basic compound (DB) having basicity reduced or lost upon irradiation with actinic rays or radiation (hereinafter also referred to as a "compound (DB)") is a compound which has a proton-accepting functional group, and decomposes under irradiation with actinic rays or radiation to exhibit deterioration in proton-accepting properties, no proton-accepting properties, or a change from the proton-accepting properties to acidic properties.

The proton-accepting functional group refers to a functional group having a group or an electron which is capable of electrostatically interacting with a proton, and for example, means a functional group with a macrocyclic structure, such as a cyclic polyether, or a functional group having a nitrogen atom having an unshared electron pair not contributing to n-conjugation. The nitrogen atom having an unshared electron pair not contributing to n-conjugation is, for example, a nitrogen atom having a partial structure represented by the following formula.

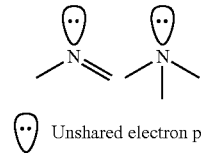

Preferred examples of the partial structure of the proton-accepting functional group include a crown ether structure, an azacrown ether structure, primary to tertiary amine structures, a pyridine structure, an imidazole structure, and a pyrazine structure.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (DB) having the proton-accepting functional group and the proton.

The proton-accepting properties can be confirmed by performing pH measurement.

The acid dissociation constant pKa of the compound generated by decomposition of the compound (DB) upon irradiation with actinic rays or radiation preferably satisfies pKa<-1, and more preferably satisfies -13<pKa<-1, and still more preferably satisfies 13<pKa<-3.

The acid dissociation constant pKa refers to an acid dissociation constant pKa in an aqueous solution, and is defined, for example, in Chemical Handbook (II) (Revised 4th Edition, 1993, compiled by the Chemical Society of Japan, Maruzen Company, Ltd.). A lower value of the acid dissociation constant pKa indicates higher acid strength. Specifically, the acid dissociation constant pKa in an aqueous solution can be actually measured by using an infinite-dilution aqueous solution and measuring the acid dissociation constant at 25° C. Alternatively, the acid dissociation constant pKa can also be determined using the following software package 1 by computation from a value with respect to a Hammett substituent constant and the database of publicly known literature values. Any of the values of pKa described in the present specification indicate values determined by computation using the software package.

Software Package 1: Advanced Chemistry Development (ACD/Labs) Software V 8.14 for Solaris (1994-2007 ACD/Labs).

In the composition of the embodiment of the present invention, the onium salt (DC) which is a weak acid relative to a photoacid generator can be used as the acid diffusion control agent. In a case where the photoacid generator and the onium salt that generates an acid which is a weak acid relative to an acid generated from the photoacid generator are mixed and used, an acid generated from the photoacid generator upon irradiation with actinic rays or radiation produces an onium salt having a strong acid anion by discharging the weak acid through salt exchange in a case where the acid collides with an onium salt having an unreacted weak acid anion. In this process, the strong acid is exchanged with a weak acid having a lower catalytic ability, and thus, the acid is apparently deactivated and the acid diffusion can be controlled.

As the onium salt which is a weak acid relative to the photoacid generator, compounds represented by General Formulae (d1-1) to (d1-3) are preferable.

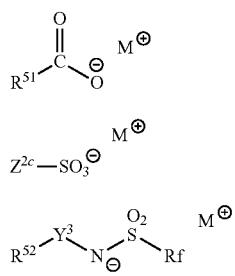

In the formula, $R^{51}$ is a hydrocarbon group which may have a substituent, $Z^{2c}$ is a hydrocarbon group having 1 to 30 carbon atoms, which may have a substituent (provided that carbon adjacent to S is not substituted with a fluorine atom), $R^{52}$ is an organic group, $Y^3$ is a linear, branched, or cyclic alkylene group or an arylene group, Rf is a hydrocarbon group including a fluorine atom, and $M^+$'s are each independently an ammonium cation, a sulfonium cation, or an iodonium cation.

Preferred examples of the sulfonium cation or iodonium cation represented by $M^+$ include the sulfonium cation exemplified for General Formula (ZI) and the iodonium cation exemplified for General Formula (ZI).

The onium salt (DC) which is a weak acid relative to a photoacid generator may be a compound having a cationic moiety and an anionic moiety in the same molecule, in which the cationic moiety and the anionic moiety are linked by a covalent bond (hereinafter also referred to as a "compound (DCA)").

The compound (DCA) is preferably a compound represented by any of General Formulae (C-1) to (C-3).

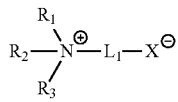

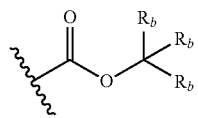

In General Formulae (C-1) to (C-3), $R_1$, $R_2$, and $R_3$ each independently represent a substituent having 1 or more carbon atoms.

$L_1$ represents a divalent linking group that links a cationic moiety with an anionic moiety, or a single bond.

—$X^-$ represents an anionic moiety selected from —COO$^-$, —SO$_3^-$, —SO$_2^-$, and —N$^-$—R$_4$. R$_4$ represents a monovalent substituent having at least one of a carbonyl group: —C(=O)—, a sulfonyl group: —S(=O)$_2$—, or a sulfinyl group: —S(=O)— at a site for linking to an adjacent N atom.

$R_1$, $R_2$, $R_3$, $R_4$, and $L_1$ may be bonded to each other to form a ring structure. Furthermore, in General Formula (C-3), two of $R_1$ to $R_3$ together represent one divalent substituent, and may be bonded to an N atom by a double bond.

Examples of the substituent having 1 or more carbon atoms in each of $R_1$ to $R_3$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group. The alkyl group, the cycloalkyl group, or the aryl group is preferable.

Examples of $L_1$ as a divalent linking group include a linear or branched alkylene group, a cycloalkylene group, an arylene group, a carbonyl group, an ether bond, an ester bond, an amide bond, a urethane bond, a urea bond, and a group formed by a combination of two or more of these groups. $L_1$ is preferably the alkylene group, the arylene group, the ether bond, the ester bond, and the group formed by a combination of two or more of these groups.

The low-molecular-weight compound (DD) having a nitrogen atom and having a group that is eliminated by an action of an acid (hereinafter also referred to as a "compound (DD)") is preferably an amine derivative having a group that is eliminated by an action of an acid on the nitrogen atom.

As the group that is eliminated by an action of an acid, an acetal group, a carbonate group, a carbamate group, a tertiary ester group, a tertiary hydroxyl group, or a hemiaminal ether group is preferable, and the carbamate group or the hemiaminal ether group is more preferable.

The molecular weight of the compound (DD) is preferably 100 to 1,000, more preferably 100 to 700, and still more preferably 100 to 500.

The compound (DD) may have a carbamate group having a protective group on the nitrogen atom. The protective group constituting the carbamate group is represented by General Formula (d-1).

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). $R_b$'s may be bonded to each other to form a ring.

The alkyl group, the cycloalkyl group, the aryl group, or the aralkyl group represented by $R_b$ may be each independently substituted with a functional group such as a hydroxyl group, a cyano group, an amino group, a pyrrolidino group, a piperidino group, a morpholino group, and an oxo group, an alkoxy group, or a halogen atom. The same applies to the alkoxyalkyl group represented by $R_b$.

As $R_b$, a linear or branched alkyl group, a cycloalkyl group, or an aryl group is preferable, and the linear or branched alkyl group, or the cycloalkyl group is more preferable.

Examples of the ring formed by the mutual linkage of two of $R_b$'s include an alicyclic hydrocarbon, an aromatic hydrocarbon, a heterocyclic hydrocarbon, and derivatives thereof.

Examples of the specific structure of the group represented by General Formula (d-1) include, but are not limited to, the structures disclosed in paragraph [0466] of the specification of US2012/0135348A1.

The compound (DD) preferably has a structure represented by General Formula (6).

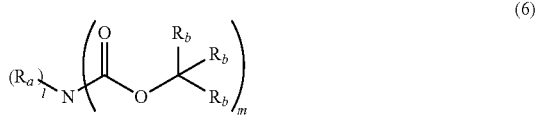

(6)

In General Formula (6), l represents an integer of 0 to 2, m represents an integer of 1 to 3, and these satisfy l+m=3.

$R_a$ represents a hydrogen atom, an alkyl group, a cycloalkyl group, an aryl group, or an aralkyl group. In a case where l is 2, two of $R_a$'s may be the same as or different from each other, and the two of $R_a$'s may be linked to each other to form a heterocycle with the nitrogen atom in the formula. This heterocycle may include a heteroatom other than the nitrogen atom in the formula.

$R_b$ has the same definition as $R_b$ in General Formula (d-1), and preferred examples are also the same.

In General Formula (6), the alkyl group, the cycloalkyl group, the aryl group, and the aralkyl group as $R_a$ may be each independently substituted with the same groups as the group mentioned above as a group which may be substituted in the alkyl group, the cycloalkyl group, the aryl group, and the aralkyl group as $R_b$.

Specific examples of the alkyl group, the cycloalkyl group, the aryl group, and the aralkyl group (these groups may be substituted with the groups as described above) of $R_a$ include the same groups as the specific examples as described above with respect to $R_b$.

Specific examples of the particularly preferred compound (DD) in the present invention include, but are not limited to, the compounds disclosed in paragraph [0475] of the specification of US2012/0135348A1.

The onium salt compound (DE) having a nitrogen atom in the cationic moiety (hereinafter also referred to as a "compound (DE)") is preferably a compound having a basic moiety including a nitrogen atom in the cationic moiety. The basic moiety is preferably an amino group, and more preferably an aliphatic amino group. All of the atoms adjacent to the nitrogen atom in the basic moiety are still more preferably hydrogen atoms or carbon atoms. In addition, from the viewpoint of improving basicity, it is preferable that an electron-withdrawing functional group (such as a carbonyl group, a sulfonyl group, a cyano group, and a halogen atom) is not directly linked to the nitrogen atom.

Preferred specific examples of the compound (DE) include, but are not limited to, the compounds disclosed in paragraph [0203] of US2015/0309408A1.

Preferred examples of the acid diffusion control agent are shown below, but the present invention is not limited thereto. Me represents a methyl group.

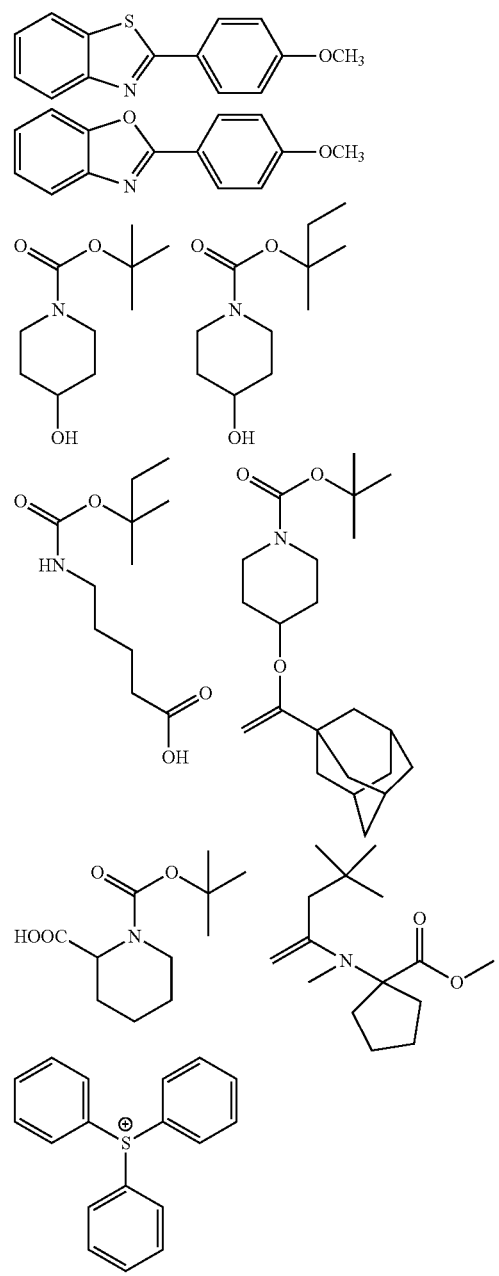

91
-continued
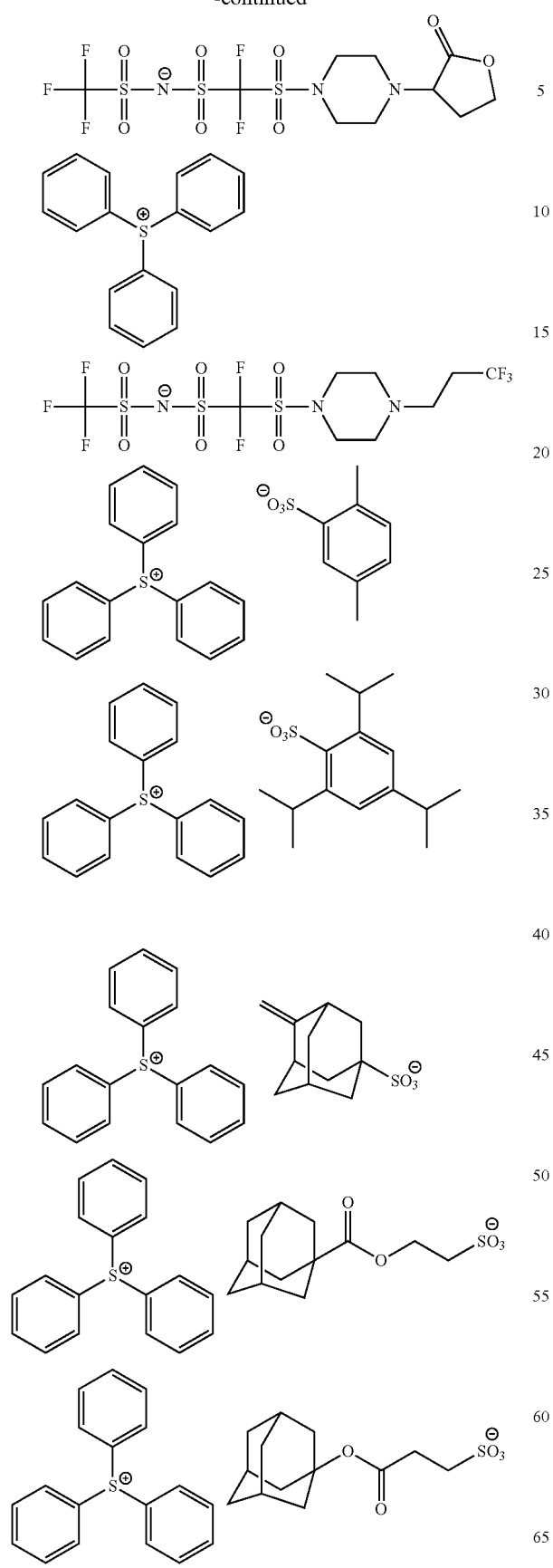
92
-continued
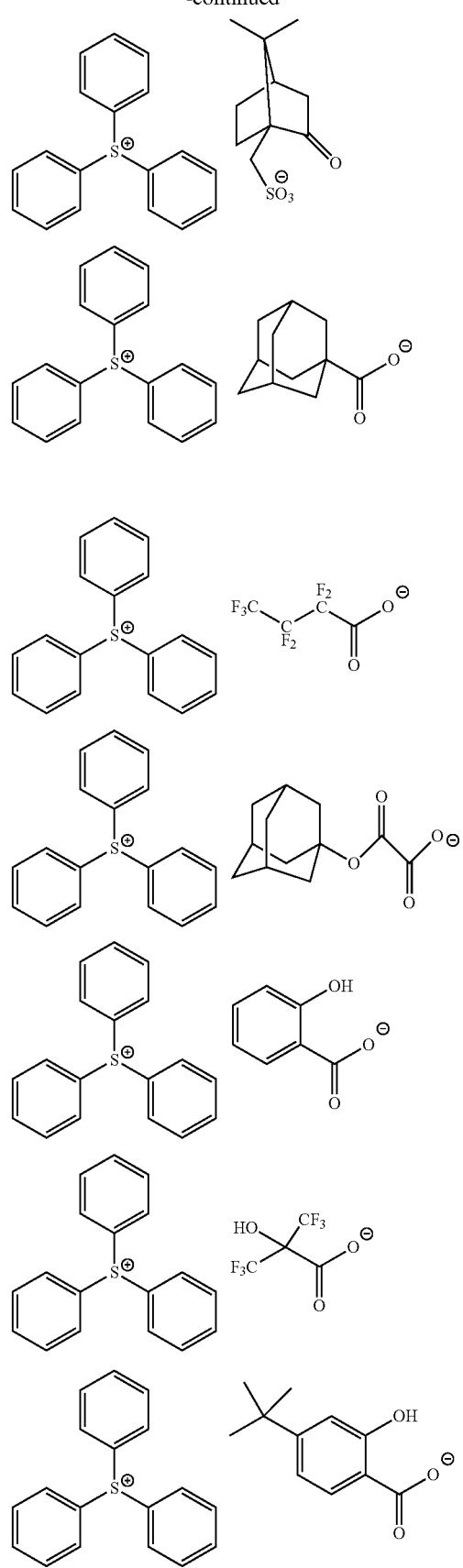

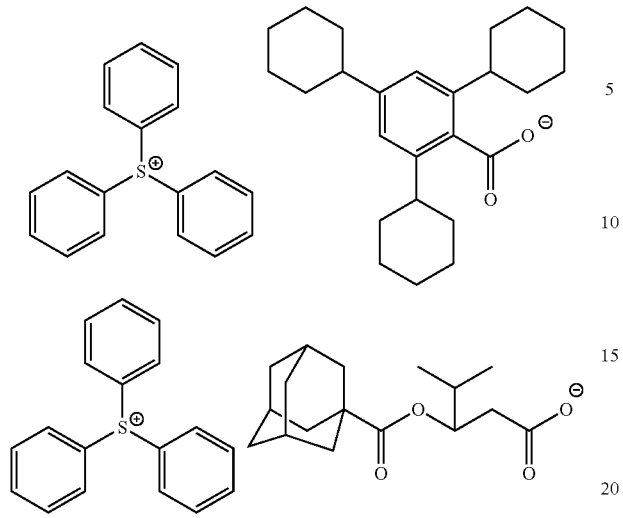
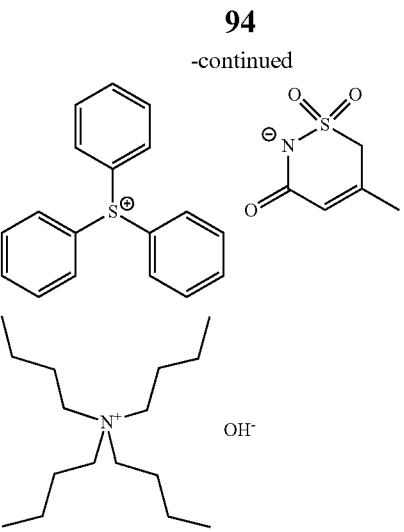
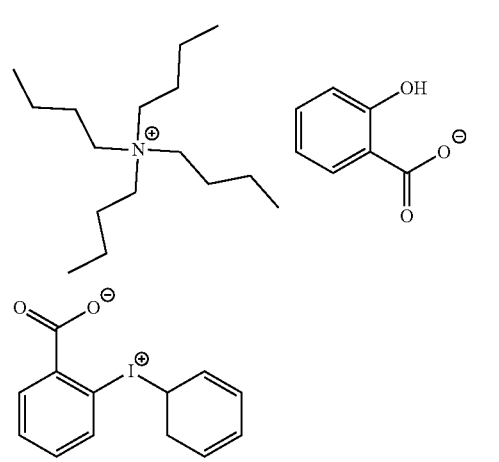
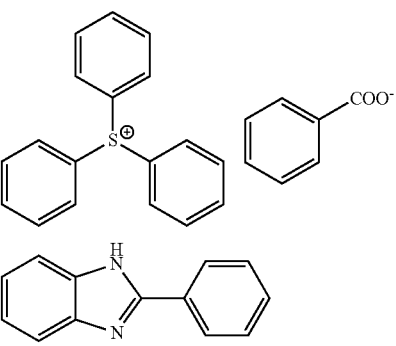
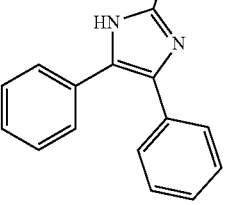
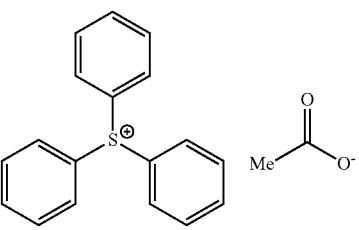
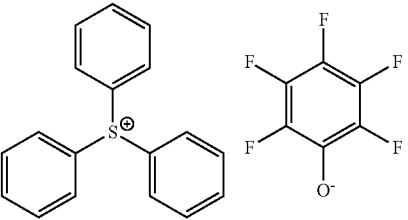

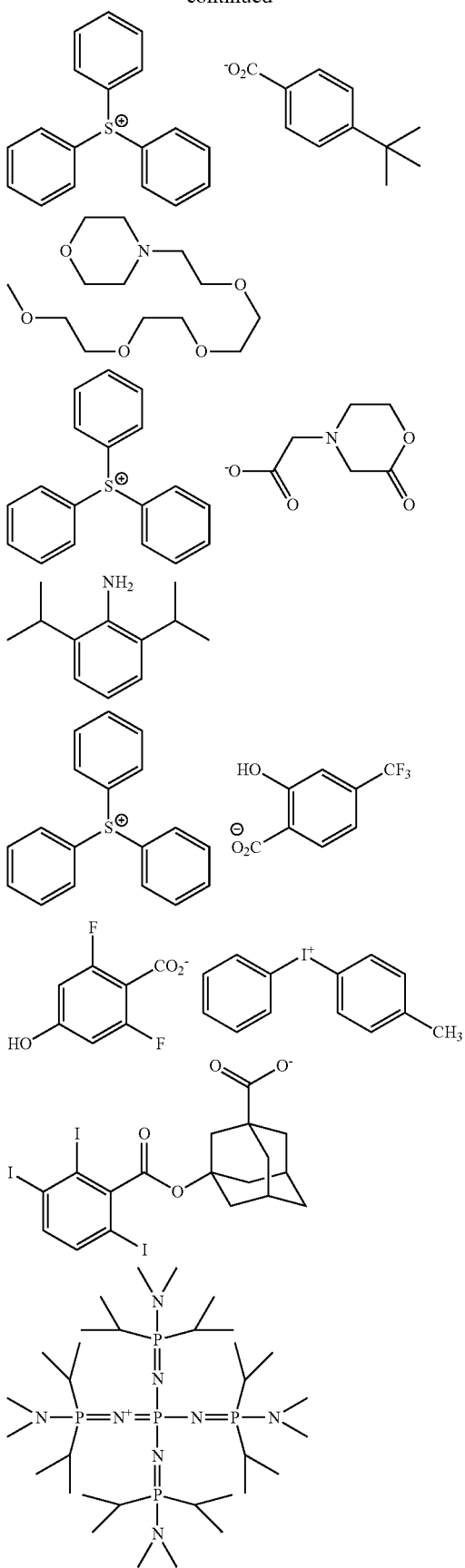
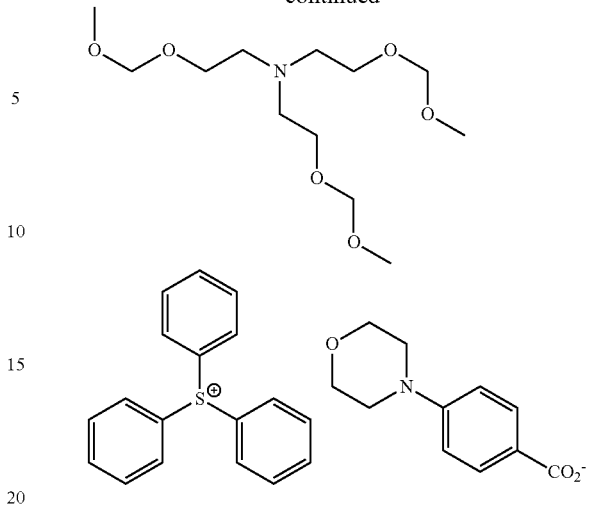

In the composition of the embodiment of the present invention, the acid diffusion control agents may be used singly or in combination of two or more kinds thereof.

The content of the acid diffusion control agent (in a case where a plurality of kinds of the acid diffusion control agents are present, a total content thereof) in the composition of the embodiment of the present invention is preferably 0.001% to 20% by mass, and more preferably 0.01% to 10% by mass, with respect to the total solid content of the composition.

[Solvent]

The composition of the embodiment of the present invention preferably contains a solvent.

In the composition of the embodiment of the present invention, a known resist solvent can be appropriately used. For example, the known solvents disclosed in paragraphs [0665] to [0670] of the specification of US2016/0070167A, paragraphs [0210] to [0235] of the specification of US2015/0004544A1, paragraphs [0424] to [0426] of the specification of US2016/0237190A1, and paragraphs [0357] to [0366] of the specification of US2016/0274458A1 can be suitably used.

Examples of the solvent which can be used in the preparation of the composition include organic solvents such as alkylene glycol monoalkyl ether carboxylate, alkylene glycol monoalkyl ether, alkyl lactic acid ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

As the organic solvent, a mixed solvent obtained by mixing a solvent having a hydroxyl group in the structure and a solvent having no hydroxyl group may be used.

As the solvent having a hydroxyl group and the solvent having no hydroxyl group, the above-mentioned exemplary compounds can be appropriately selected, but as the solvent including a hydroxyl group, alkylene glycol monoalkyl ether or alkyl lactate is preferable, and propylene glycol monomethyl ether (PGME: 1-methoxy-2-propanol), propylene glycol monoethyl ether (PGEE), methyl 2-hydroxyisobutyrate, or ethyl lactate is more preferable. Further, as the solvent having no hydroxyl group, alkylene glycol monoalkyl ether acetate, alkyl alkoxypropionate, a monoketone compound which may have a ring, a cyclic lactone, alkyl acetate, or the like is preferable, and among these, propylene glycol monomethyl ether acetate (PGMEA: 1-methoxy-2-acetoxypropane), ethyl ethoxypropionate, 2-heptanone, γ-butyrolactone, cyclohexanone, cyclopentanone, or butyl acetate is more preferable, and propylene glycol monomethyl ether acetate, γ-butyrolactone, ethyl ethoxypropionate, cyclohexanone, cyclopentanone, or 2-heptanone are still more preferable. As a solvent having no hydroxyl group, propylene carbonate is also preferable.

A mixing ratio (mass ratio) of the solvent having a hydroxyl group to the solvent having no hydroxyl group is 1/99 to 99/1, preferably 10/90 to 90/10, and more preferably 20/80 to 60/40. A mixed solvent containing 50% by mass or more of the solvent having no hydroxyl group is preferable from the viewpoint of coating evenness.

The solvent preferably contains propylene glycol monomethyl ether acetate, and may be either a single solvent of propylene glycol monomethyl ether acetate or a mixed solvent of two or more kinds containing propylene glycol monomethyl ether acetate.

[Surfactant]

The composition of the embodiment of the present invention may further include a surfactant. By containing the surfactant, in a case where an exposure light source at a wavelength of 250 nm or less, in particular, 220 nm or less is used, it is possible to form a pattern with good sensitivity and resolution and less adhesiveness and development defects.

It is particularly preferable to use a fluorine-based and/or silicon-based surfactant as the surfactant.

Examples of the fluorine-based and/or silicon-based surfactants include the surfactants described in [0276] of the specification of US2008/0248425A. In addition, EFTOP EF301 or EF303 (manufactured by Shin-Akita Chemical Co., Ltd.); FLORAD FC430, 431, or 4430 (manufactured by Sumitomo 3M Inc.); MEGAFACE F171, F173, F176, F189, F113, F110, F177, F120, or R08 (manufactured by DIC Corporation); SURFLON S-382, SC101, 102, 103, 104, 105, or 106 (manufactured by Asahi Glass Co., Ltd.); TROYSOL S-366 (manufactured by Troy Chemical Corporation); GF-300 or GF-150 (manufactured by TOAGOSEI Co., Ltd.); SURFLON S-393 (manufactured by Seimi Chemical Co., Ltd.); EFTOP EF121, EF122A, EF122B, RF22C, EF125M, EF135M, EF351, EF352, EF801, EF802, or EF601 (manufactured by JEMCO Inc.); PF636, PF656, PF6320, or PF6520 (manufactured by OMNOVA Solutions Inc.); or FTX-204G, 208G, 218G, 230G, 204D, 208D, 212D, 218D, or 222D (manufactured by NEOS COMPANY LIMITED) may be used. In addition, a polysiloxane polymer, KP-341 (manufactured by Shin-Etsu Chemical Co., Ltd.), can also be used as the silicon-based surfactant.

Furthermore, the surfactant may be synthesized using a fluoroaliphatic compound produced by a telomerization method (also referred to as a telomer method) or an oligomerization method (also referred to as an oligomer method), in addition to the known surfactants as shown above. Specifically, a polymer comprising a fluoroaliphatic group derived from the fluoroaliphatic compound may also be used as the surfactant. The fluoroaliphatic compound can be synthesized in accordance with the method described in JP2002-090991A.

In addition, another surfactant other than the fluorine-based and/or silicon-based surfactants, described in [0280] of US2008/0248425A, may also be used.

These surfactants may be used singly or in combination of two or more kinds thereof.

In a case where the composition of the embodiment of the present invention includes a surfactant, a content thereof is preferably 0% to 2% by mass, more preferably 0.0001% to 2% by mass, and still more preferably 0.0005% to 1% by mass, with respect to the total solid content of the composition.

[Other Additives]

The composition of the embodiment of the present invention can contain, in addition to the components described above, a carboxylic acid, an onium carboxylate salt, a dissolution inhibiting compound having a molecular weight of 3,000 or less described in Proceeding of SPIE, 2724,355 (1996) and the like, a dye, a plasticizer, a photosensitizer, a light absorber, an antioxidant, and the like as appropriate.

In particular, carboxylic acid can be preferably used for improving the performance. The carboxylic acid is preferably an aromatic carboxylic acid such as benzoic acid or naphthoic acid.

In a case where the composition of the embodiment of the present invention includes a carboxylic acid, the content of the carboxylic acid is preferably 0.01% to 10% by mass, more preferably 0.01% to 5% by mass, and still more preferably 0.01% to 3% by mass, with respect to the total solid content of the composition.

The actinic ray-sensitive or radiation-sensitive resin composition of the embodiment of the present invention is used with a film thickness of preferably 10 to 250 nm, more preferably 20 to 200 nm, and still more preferably 30 to 100 nm, from the viewpoint of improving a resolving power. Such a film thickness can be obtained by setting the concentration of solid contents in the composition to an appropriate range to provide the composition with a suitable viscosity and improve the coating property and the film forming property.

The concentration of solid contents of the actinic ray-sensitive or radiation-sensitive resin composition in the embodiment of the present invention is usually 1.0% to 10% by mass, preferably 2.0% to 5.7% by mass, and more preferably 2.0% to 5.3% by mass. By setting the concentration of solid contents within the range, the resist solution can be uniformly applied onto a substrate, and further, it is possible to form a resist pattern having excellent line width roughness.

The concentration of solid contents is a mass percentage of the mass of other components excluding the solvent with respect to the total mass of the actinic ray-sensitive or radiation-sensitive resin composition.

[Use]

The composition of the embodiment of the present invention relates to an actinic ray-sensitive or radiation-sensitive resin composition having properties changed by undergoing a reaction upon irradiation with actinic rays or radiation. More specifically, the composition of the embodiment of the present invention relates to an actinic ray-sensitive or radiation-sensitive resin composition which is used in a step of manufacturing a semiconductor such as an integrated circuit (IC), for the manufacture of a circuit board for a liquid crystal, a thermal head, or the like, the manufacture of a mold structure for imprinting, other photofabrication steps, or production of a planographic printing plate or an acid-curable composition. A pattern formed in the present invention can be used in an etching step, an ion implantation step, a bump electrode forming step, a rewiring forming step, a microelectromechanical system (MEMS), or the like.

[Actinic Ray-Sensitive or Radiation-Sensitive Film]

The present invention also relates to an actinic ray-sensitive or radiation-sensitive film (preferably a resist film) formed with the actinic ray-sensitive or radiation-sensitive composition of the embodiment of the present invention. Such a film is formed, for example, by applying the composition of the embodiment of the present invention onto a support such as a substrate. The thickness of this film is preferably 0.02 to 0.1 µm. As a method for applying the composition on the substrate, a suitable application method such as spin coating, roll coating, flow coating, dip coating, spray coating, and doctor coating is applied on a substrate, but the spin coating is preferable and the rotation speed is preferably 1,000 to 3,000 rotations per minute (rpm). The coating film is prebaked at 60° C. to 150° C. for 1 to 20 minutes, and preferably at 80° C. to 120° C. for 1 to 10 minutes to form a thin film.

For a material constituting a substrate to be processed and an outermost layer thereof, for example, in a case of a semiconductor wafer, a silicon wafer can be used, and examples of the material forming the outermost layer include Si, $SiO_2$, SiN, SiON, and TiN, WSi, BPSG, SOG, and an organic antireflection film.

Before forming the resist film, an antireflection film may be previously coated on the substrate.

As the antireflection film, any of an inorganic film type antireflection film such as titanium, titanium dioxide, titanium nitride, chromium oxide, carbon, and amorphous silicon, and an organic film type antireflection film formed of a light absorber and a polymer material can be used. Further, as the organic antireflection film, a commercially available organic antireflection film such as DUV30 series or DUV-40 series manufactured by Brewer Science Inc., or AR-2, AR-3, or AR-5 manufactured by Shipley Co., Ltd. can be used.

Moreover, in the pattern forming method of the embodiment of the present invention, a topcoat may be formed on the upper layer of the resist film. It is preferable that the topcoat is not mixed with the resist film and can be uniformly applied to the upper layer of the resist film.

The topcoat is not particularly limited, a topcoat known in the related art can be formed by a method known in the related art, and for example, the topcoat can be formed in accordance with the description in paragraphs 0072 to 0082 of JP2014-059543A.

For example, it is preferable that a topcoat containing a basic compound as described in JP2013-061648A is formed on a resist film. Specific examples of the basic compound which can be included in the topcoat include the same ones as those for the above-mentioned acid diffusion inhibitor.

In addition, the topcoat preferably includes a compound which includes at least one group or bond selected from the group consisting of an ether bond, a thioether bond, a hydroxyl group, a thiol group, a carbonyl bond, and an ester bond.

Furthermore, the topcoat preferably contains a resin. The resin which can be contained in the topcoat is not particularly limited, but the same resin as the hydrophobic resin which can be included in the actinic ray-sensitive or radiation-sensitive composition can be used.

With regard to the hydrophobic resin, reference can be made to the descriptions in [0017] to [0023] of JP2013-061647A ([0017] to [0023] of the corresponding US2013/0244438A), and [0016] to [0165] of JP2014-056194A, the contents of which are incorporated herein by reference.

The topcoat preferably includes a resin containing a repeating unit having an aromatic ring. By containing the repeating unit having an aromatic ring, a secondary electron-generating efficiency and an acid-generating efficiency from a compound that generates an acid with actinic rays or radiation increase, particularly upon irradiation with electron beams or EUV exposure, and thus, an effect of realizing high sensitivity and high resolution in the formation of a pattern can be expected.

In a case where the topcoat includes a plurality of resins, it is preferable that the topcoat includes at least one resin (XA) having a fluorine atom and/or a silicon atom. It is more preferable that the topcoat composition includes at least one resin (XA) having a fluorine atom and/or a silicon atom, and a resin (XB) having a content of a fluorine atom and/or silicon atom which is smaller than that of the resin (XA). As a result, in a case where a topcoat film is formed, the resin (XA) is unevenly distributed on a surface of the topcoat film, and thus, that it is possible to improve performance such as development characteristics and immersion liquid followability.

In addition, the topcoat may contain an acid generator and a crosslinking agent.

The topcoat is typically formed from a composition for forming a topcoat.

For the composition for forming a topcoat, it is preferable that the respective components are dissolved in a solvent and filtered using a filter. The filter is preferably made of polytetrafluoroethylene, polyethylene, or nylon, which has a pore size of 0.1 µm or less, more preferably 0.05 µm or less, and still more preferably 0.03 µm or less. Furthermore, in a case where the concentration of solid contents of the composition is high (for example, 25% by mass or more), the pore size of a filter used for filtration using a filter is preferably 3 µm or less, more preferably 0.5 µm or less, still more preferably 0.3 µm or less. The filter is preferably a polytetrafluoroethylene-made, polyethylene-made, or nylon-made filter. In the filtration using a filter as shown in the specification of JP2002-062667A, circulating filtration may be performed or the filtration may be performed by the linkage of a plurality of kinds of filters in series or in parallel. In addition, the composition may be filtered in plural times. Furthermore, the composition may be subjected to a deaeration treatment or the like before or after filtration using a filter.

The composition for forming a topcoat preferably does not include impurities such as a metal. The content of the metal components included in these materials is preferably 10 ppm or less, more preferably 5 ppm or less, and still more preferably 1 ppm or less, and it is particularly preferable that substantially no metal component is included (below a detection limit of the measuring apparatus).

It is also preferable to partially or wholly subjecting the inside of a device used in a producing step (a step for synthesizing a raw material, and the like) of a raw material (a resin, a photoacid generator, and the like) of a resist composition to a glass lining treatment so that a content of metal impurities of the resist composition is adjusted to be small (for example, on the order of ppm by mass). Such a method is described, for example, in The Chemical Daily, Dec. 21, 2017.

In a case where the exposure which will be described later is liquid immersion exposure, the topcoat is arranged between the resist film and the immersion liquid, and also functions as a layer which does not bring the resist film into direct contact with the immersion liquid. In this case, preferred characteristics required for the topcoat (composition for forming a topcoat) are coating suitability onto the resist film, transparency to radiation, particularly to light at 193 nm, and sparing solubility in an immersion liquid (preferably water). Further, it is preferable that the topcoat is not mixed with the resist film and can be uniformly applied onto a surface of the resist film.

Moreover, in order to uniformly apply the composition for forming a topcoat onto a surface of the resist film while not dissolving the resist film, it is preferable that the composition for forming a topcoat contains a solvent in which the resist film is not dissolved. It is more preferable to use a solvent of a component different from a developer (organic developer) containing an organic solvent which will be described in detail later as the solvent in which the resist film is not dissolved.

A method for applying the composition for forming a topcoat is not particularly limited, and a spin coating method, a spray coating method, a roller coating method, a dip method, or the like which is known in the related art can be used.

The thickness of the topcoat is not particularly limited, but is usually 5 nm to 300 nm, preferably 10 nm to 300 nm, more preferably 20 nm to 200 nm, and still more preferably 30 nm to 100 nm, from the viewpoint of transparency to an exposure light source.

After forming the topcoat, the substrate is post-baked (PB) as necessary.

From the viewpoint of resolution, it is preferable that the refractive index of the topcoat is close to that of the resist film.

The topcoat is preferably insoluble in an immersion liquid, and more preferably insoluble in water.

With regard to the receding contact angle of the topcoat, the receding contact angle (23° C.) of the immersion liquid with respect to the topcoat is preferably 50 to 100 degrees, and more preferably 80 to 100 degrees, from the viewpoint of immersion liquid followability.

In the liquid immersion exposure, from the viewpoint that the immersion liquid needs to move on a wafer following the movement of an exposure head that is scanning the wafer at a high speed and forming an exposure pattern, the contact angle of the immersion liquid with respect to the topcoat in a dynamic state is important, and in order to obtain better resist performance, it is preferable that the immersion liquid has a receding contact angle in the range.

During the release of the topcoat, an organic developer may be used, and another release agent may be separately used. As the release agent, a solvent hardly permeating the resist film is preferable. From the viewpoint that the release of the topcoat can be carried out at the same time as the development of the resist film, the topcoat is preferably releasable by an organic developer. The organic developer used for the release is not particularly limited as long as it makes it possible to dissolve and remove a less exposed area of the resist film.

From the viewpoint of the release with the organic developer, the dissolution rate of the topcoat in the organic developer is preferably 1 to 300 nm/sec, and more preferably 10 to 100 nm/sec.

Here, the dissolution rate of the topcoat in the organic developer is a film thickness decreasing rate in a case where the topcoat is exposed to a developer after film formation, and in the present invention, it is a rate in a case where the topcoat is dipped in butyl acetate at 23° C.

An effect of reducing development defects after developing a resist film is accomplished by adjusting the dissolution rate of a topcoat in an organic developer to 1/sec or more, and preferably 10 nm/sec or more. Further, by setting the dissolution rate to 300 nm/sec or less, and preferably 100 nm/sec, an effect that the line edge roughness of a pattern after the development of the resist film is improved is accomplished, possibly due to an effect of reducing the exposure unevenness during the liquid immersion exposure.

The topcoat may be removed using another known developer, for example, an aqueous alkali solution. Specific examples of the usable aqueous alkali solution include an aqueous tetramethylammonium hydroxide solution.

[Pattern Forming Method]

The present invention also relates to a pattern forming method including a resist film forming step of forming a resist film using the actinic ray-sensitive or radiation-sensitive resin composition of the embodiment of the present invention, an exposing step of exposing the resist film, and a developing step of developing the exposed resist film using a developer.

In the present invention, the exposure is preferably carried out using electron beams, an ArF excimer laser, or extreme ultraviolet rays, and more preferably electron beams or extreme ultraviolet rays.

For exposure (pattern forming step) on a resist film in the production of a precision integrated circuit element, first, irradiation with an ArF excimer laser, electron beams, or extreme ultraviolet rays (EUV) is preferably performed patternwise on the resist film of the present invention. In a case of the ArF excimer laser, the exposure dose is approximately 1 to 100 mJ/cm$^2$, preferably approximately 20 to 60 mJ/cm$^2$; in a case of the electron beams, the exposure dose is approximately 0.1 to 20 µC/cm$^2$, and preferably approximately 3 to 10 µC/cm$^2$; and in a case of the extreme ultraviolet rays, the exposure dose is approximately 0.1 to 20 mJ/cm$^2$, and preferably approximately 3 to 15 mJ/cm$^2$.

Subsequently, post-exposure baking is performed on a hot plate, preferably at 60° C. to 150° C. for 5 seconds to 20 minutes, more preferably at 80° C. to 120° C. for 15 seconds to 10 minutes, and still more preferably at 80° C. to 120° C. for 1 to 10 minutes, and then development, rinsing, and drying are performed to form a pattern. Here, the post-exposure baking is appropriately adjusted depending on the acid decomposability of the repeating unit having an acid-decomposable group in the resin (A). In a case where the acid decomposability is low, it is also preferable that the temperature for post-exposure baking is 110° C. or higher and the heating time is 45 seconds or longer.

The developer is appropriately selected, but an alkali developer (typically an aqueous alkali solution) or a developer containing an organic solvent (also referred to as an organic developer) is preferably used. In a case where the developer is an aqueous alkali solution, development is performed with an aqueous alkali solution of tetramethylammonium hydroxide (TMAH), tetrabutylammonium hydroxide (TBAH), or the like at 0.1% to 5% by mass, and preferably 2% to 3% by mass for 0.1 to 3 minutes, and preferably 0.5 to 2 minutes by an ordinary method such as a dip method, a puddle method, a spray method, or the like. An appropriate amount of an alcohol and/or a surfactant may be added to the alkali developer. Thus, in the formation of a negative tone pattern, the film in the unexposed area is dissolved and the exposed area is hardly dissolved in the developer; and in the formation of a positive tone pattern, the film in the exposed area is dissolved and the film in the unexposed area is hardly dissolved in the developer, so that a desired pattern is formed on the substrate.

In a case where the pattern forming method of the embodiment of the present invention has a step of performing development using an alkali developer, as the alkali developer, for example, an aqueous alkali solution of inorganic alkalis such as sodium hydroxide, potassium hydroxide, sodium carbonate, sodium silicate, sodium metasilicate, and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, tetraalkylammonium hydroxides such as tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, ethyltrimethylammonium hydroxide, butyltrimethylammonium hydroxide, methyltriamylammonium hydroxide, and dibutyldipentylammonium hydroxide, quaternary ammonium salts such as trimethylphenylammonium hydroxide, trimethylbenzylammonium hydroxide, triethylbenzylammonium hydroxide, and dimethylbis(2-hydroxytetyl)ammonium hydroxide, or cyclic amines such as pyrrole and piperidine can be used.

Furthermore, the aqueous alkali solution can be used after adding an appropriate amount of alcohols or a surfactant thereto.

The alkali concentration of the alkali developer is usually 0.1% to 20% by mass.

The pH of the alkali developer is usually 10.0 to 15.0.

In particular, a 2.38%-by-mass aqueous tetramethylammonium hydroxide solution is desirable.

Pure water may be used as the rinsing liquid in the rinse treatment performed after the alkali development, and an appropriate amount of a surfactant may be added to the pure water.

In addition, after the developing treatment or the rinsing treatment, a treatment of removing the developer or the rinsing liquid adhering to a pattern with a supercritical fluid can be performed.

In a case where the pattern forming method of the embodiment of the present invention has a step of performing development using a developer containing an organic solvent, as the developer in the step (hereinafter also referred to as an organic developer), a polar solvent such as a ketone-based solvent, an ester-based solvent, an alcohol-based solvent, an amide-based solvent, and an ether-based solvent, or a hydrocarbon-based solvent can be used.

In the present invention, the ester-based solvent is a solvent having an ester group in the molecule, the ketone-based solvent is a solvent having a ketone group in the molecule, the alcohol-based solvent is a solvent having an alcoholic hydroxyl group in the molecule, the amide-based solvent is a solvent having an amido group in the molecule, and the ether-based solvent is a solvent having an ether bond in the molecule. Among those, a solvent having a plurality of the functional groups in one molecule is also present, but in this case, it is applicable to any of solvent species including the functional group contained in the solvent. For example, diethylene glycol monomethyl ether is applicable to any of the alcohol-based solvent and the ether-based solvent in the classification. In addition, the hydrocarbon-based solvent is a hydrocarbon solvent having no substituent.

In particular, a developer containing at least one solvent selected from the ketone-based solvent, the ester-based solvent, the alcohol-based solvent, or the ether-based solvent is preferable.

It is preferable to use an ester-based solvent having 7 or more carbon atoms (preferably 7 to 14 carbon atoms, more preferably 7 to 12 carbon atoms, and still more preferably 7 to 10 carbon atoms), and 2 or less heteroatoms as the developer from the viewpoint that the swelling of the resist film can be suppressed.

The heteroatom of the ester-based solvent is an atom other than a carbon atom and a hydrogen atom, and examples thereof include an oxygen atom, a nitrogen atom, and a sulfur atom. The number of the heteroatoms is preferably 2 or less.

Preferred examples of the ester-based solvents having 7 or more carbon atoms and 2 or less heteroatoms include amyl acetate, isoamyl acetate, 2-methylbutyl acetate, 1-methylbutyl acetate, hexyl acetate, pentyl propionate, hexyl propionate, heptyl propionate, butyl butanoate, and isobutyl isobutanoate, and isoamyl acetate or isobutyl isobutanoate is particularly preferably used.

As the developer, a mixed solvent of the ester-based solvent and the hydrocarbon-based solvent or a mixed solvent of the ketone-based solvent and the hydrocarbon-based solvent may be used instead of the ester-based solvent having 7 or more carbon atoms and having 2 or less heteroatoms as mentioned above. Also in this case, it is effective in suppressing the swelling of the resist film.

In a case where the ester-based solvent and the hydrocarbon-based solvent are used in combination, it is preferable to use isoamyl acetate as the ester-based solvent. In addition, from the viewpoint of adjusting the solubility of the resist film, a saturated hydrocarbon solvent (for example, octane, nonane, decane, dodecane, undecane, and hexadecane) is preferably used as the hydrocarbon-based solvent.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, 2,5-dimethyl-4-hexanone, diisobutyl ketone, cyclohexanone, methylcyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate, and diisobutyl ketone and 2,5-dimethyl-4-hexanone are particularly preferably used.

Examples of the ester-based solvent include methyl acetate, butyl acetate, ethyl acetate, isopropyl acetate, pentyl acetate, isoamyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, and methyl 2-hydroxyisobutyrate.

Examples of the alcohol-based solvent include alcohols such as methyl alcohol, ethyl alcohol, n-propyl alcohol, isopropyl alcohol, n-butyl alcohol, sec-butyl alcohol, 4-methyl-2-pentanol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol; and glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include anisole, dioxane, and tetrahydrofuran, in addition to the glycol ether-based solvents.

As the amide-based solvent, for example, N-methyl-2-pyrrolidone, N,N-dimethylacetamide, N,N-dimethylformamide, hexamethylphosphoric triamide, 1,3-dimethyl-2-imidazolidinone, or the like can be used.

Examples of the hydrocarbon-based solvent include aromatic hydrocarbon-based solvents such as toluene and xylene, and aliphatic hydrocarbon-based solvents such as pentane, hexane, octane, decane, and undecane.

In addition, the aliphatic hydrocarbon-based solvent which is a hydrocarbon-based solvent may be a mixture of compounds having the same number of carbon atoms but different structures. For example, in a case where decane is used as the aliphatic hydrocarbon-based solvent, 2-methylnonane, 2,2-dimethyloctane, 4-ethyloctane, isooctane, or the like which is a compound having the same number of carbon atoms and different structures, may be included in the aliphatic hydrocarbon-based solvent.

In addition, only one kind or a plurality of kinds of the compounds as described above having the same number of carbon atoms and different structures may be included.

A plurality of the solvents may be mixed or the solvent may be used in admixture with a solvent other than those described above or water. It should be noted that in order to fully exert the effects of the present invention, the moisture content of the developer as a whole is preferably less than 10% by mass, and the developer is more preferably substantially free of the moisture.

The concentration of the organic solvent (in a case of mixing a plurality of the organic solvents, a total thereof) in the organic developer is preferably 50% by mass or more, more preferably 50% to 100% by mass, still more preferably 85% to 100% by mass, even still more preferably 90% to 100% by mass, and particularly preferably 95% to 100% by mass. Most preferably, the organic solvent consists substantially only of an organic solvent. In addition, a case of consisting substantially only of an organic solvent includes a case of containing a trace amount of a surfactant, an antioxidant, a stabilizer, an antifoaming agent, or the like.

In particular, the organic developer is preferably a developer containing at least one organic solvent selected from the group consisting of a ketone-based solvent, an ester-based solvent, an alcohol-based solvent, an amide-based solvent, and an ether-based solvent.

The vapor pressure of the organic developer at 20° C. is preferably 5 kPa or less, more preferably 3 kPa or less, and particularly preferably 2 kPa or less. By setting the vapor pressure of the organic developer to 5 kPa or less, evaporation of the developer on the substrate or in the development cup is suppressed, the temperature uniformity in a wafer plane is improved, and as a result, the dimensional uniformity in the wafer plane is improved.

Specific examples of the organic developer having a vapor pressure of 5 kPa or less include ketone-based solvents such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone, and methyl isobutyl ketone, ester-based solvents such as butyl acetate, pentyl acetate, isoamyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate, and propyl lactate, alcohol-based solvents such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol, ether-based solvents such as tetrahydrofuran, amide-based solvents such as N-methyl-2-pyrrolidone, N,N-dimethylacetamide, and N,N-dimethylformamide, aromatic hydrocarbon-based solvents such as toluene and xylene, and aliphatic hydrocarbon-based solvents such as octane and decane.

Specific examples of the organic developer having a vapor pressure of 2 kPa or less, which is a particularly preferable range, include ketone-based solvents such as 1-octanone, 2-octanone, 1-nonanone, 2-nonanone, 2-heptanone, 4-heptanone, 2-hexanone, diisobutyl ketone, cyclohexanone, methylcyclohexanone, and phenylacetone, ester-based solvents such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate, and propyl lactate, alcohol-based solvents such as n-butyl alcohol, sec-butyl alcohol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol, amide-based solvents such as N-methyl-2-pyrrolidone, N,N-dimethylacetamide, and N,N-dimethylformamide, aromatic hydrocarbon-based solvents such as xylene, and aliphatic hydrocarbon-based solvents such as octane, decane, and undecane.

The organic developer may include a basic compound. Specific examples and preferred examples of the basic compound which can be included in the developer used in the present invention are the same ones as those in the basic compound which can be included in the above-described actinic ray-sensitive or radiation-sensitive composition.

An appropriate amount of a surfactant can be added to the organic developer, as necessary.

The surfactant is not particularly limited, but, for example, an ionic or nonionic fluorine-based and/or silicon-based surfactant or the like can be used. Examples of such the fluorine- and/or silicon-based surfactant include the surfactants described in, for example, JP1987-036663A (JP-S62-036663A), JP1986-226746A (JP-S61-226746A), JP1986-226745A (JP-S61-226745A), JP1987-170950A (JP-S62-170950A), JP1988-034540A (JP-S63-034540A), JP1995-230165A (JP-H07-230165A), JP1996-062834A (JP-H08-062834A), JP1997-054432A (JP-H09-054432A), JP1997-005988A (JP-H09-005988A), U.S. Pat. Nos. 5,405,720A, 5,360,692A, 5,529,881A, 5,296,330A, 5,436,098A, 5,576,143A, 5,294,511A, and 5,824,451A, and nonionic surfactants are preferable. The nonionic surfactant is not particularly limited, but it is more preferable to use a fluorine-based surfactant or a silicon-based surfactant.

The amount of the surfactant to be used is preferably 0.0001% to 2% by mass, more preferably 0.0001% to 1% by mass, and particularly preferably 0.0001% to 0.1% by mass, with respect to the total amount of the developer.

As the developing method, for example, a method in which a substrate is dipped in a tank filled with a developer for a certain period of time (a dip method), a method in which development is performed by heaping a developer up onto the surface of a substrate by surface tension, and then stopping it for a certain period of time (a puddle method), a method in which a developer is sprayed on the surface of a substrate (a spray method), a method in which a developer is continuously jetted onto a substrate rotating at a constant rate while scanning a developer jetting nozzle at a constant rate (a dynamic dispense method), or the like can be applied.

In a case where the various developing methods include a step of jetting a developer from developing nozzles of a developing device toward the resist film, the jetting pressure of the developer to be jetted (flow rate per unit area of the developer to be jetted) is preferably 2 mL/sec/mm$^2$ or less, more preferably 1.5 mL/sec/mm$^2$ or less, and still more preferably 1 mL/sec/mm$^2$ or less. There is no particular lower limit to the flow rate, but the lower limit is preferably 0.2 mL/sec/mm$^2$ or more in consideration of a throughput.

By setting the jetting pressure of the developer to be jetted within the range, it is possible to significantly reduce the pattern defects derived from resist residues after development.

Although the details of this mechanism are not clear, it is considered that by setting the jetting pressure to be in the range, the pressure applied to the resist film by the developer is likely to be reduced and the resist film/pattern is prevented from being scraped or broken carelessly.

In addition, the jetting pressure (mL/sec/mm$^2$) of the developer is a value at the outlet of the developing nozzle in the developing device.

Examples of the method of adjusting the jetting pressure of the developer include a method of adjusting a jetting pressure with a pump or the like, and a method of changing a pressure by adjusting the pressure with a supply from a pressure tank.

Furthermore, after a step of performing development using a developer including an organic solvent, a step of stopping the development may be carried out while substituting the solvent with another solvent.

A step of performing washing using a rinsing liquid may be included after the step of performing development using a developer including an organic solvent, but from the viewpoint of a throughput (productivity), an amount of the rinsing liquid to be used, and the like, a step of performing washing using a rinsing liquid may not be included.

The rinsing liquid used in the rinsing step after the developing step using a developer including an organic solvent is not particularly limited as long as the rinsing liquid does not dissolve the resist pattern, and a solution including a common organic solvent can be used. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent include the same ones as those described for the developer including an organic solvent, and in particular, suitable examples thereof include butyl acetate and methyl isobutyl carbinol.

It is preferable to perform a step of performing washing, more preferably using a rinsing liquid containing at least one organic solvent selected from the group consisting of an ester-based solvent, an alcohol-based solvent, and a hydrocarbon-based solvent, and still more preferably using a rinsing liquid containing the alcohol-based solvent or the hydrocarbon-based solvent, after the step of performing development using a developer including an organic solvent.

Among the organic solvents, the hydrocarbon-based solvent is also preferably used, and the aliphatic hydrocarbon-based solvent is more preferably used, as the organic solvent included in the rinsing liquid. As the aliphatic hydrocarbon-based solvent used in the rinsing liquid, from the viewpoint of further improving the effects, an aliphatic hydrocarbon-based solvent having 5 or more carbon atoms (for example, pentane, hexane, octane, decane, undecane, dodecane, and hexadecane) is preferable, an aliphatic hydrocarbon-based solvent having 8 or more carbon atoms is more preferable, and an aliphatic hydrocarbon-based solvent having 10 or more carbon atoms is still more preferable.

Incidentally, the upper limit value of the number of carbon atoms in the aliphatic hydrocarbon-based solvent is not particularly limited, and for example, is 16 or less, preferably 14 or less, and more preferably 12 or less.

Among the aliphatic hydrocarbon-based solvents, decane, undecane, or dodecane is particularly preferable, and undecane is the most preferable.

By using the hydrocarbon-based solvent (in particular, the aliphatic hydrocarbon-based solvent) as the organic solvent included in the rinsing liquid as described above, the developer permeating into the resist film slightly after development is washed away, the swelling is further suppressed, and thus, an effect of suppressing pattern collapse is further exhibited.

The respective components in a plural number may be mixed or the components may also be used in admixture with an organic solvent other than the solvents.

The moisture content of the rinsing liquid is preferably 10% by mass or less, more preferably 5% by mass or less, and particularly preferably 3% by mass or less. By setting the moisture content to 10% by mass or less, good development characteristics can be obtained.

The vapor pressure at 20° C. of the rinsing liquid which is used after the step of performing development using a developer including an organic solvent is preferably from 0.05 kPa to 5 kPa, more preferably from 0.1 kPa to 5 kPa, and most preferably from 0.12 kPa to 3 kPa. By setting the vapor pressure of the rinsing liquid to be from 0.05 kPa to 5 kPa, the temperature uniformity in a wafer plane is improved, and further, the dimensional uniformity in a wafer plane is enhanced by suppression of swelling due to the permeation of the rinsing liquid.

The rinsing liquid can be used after an appropriate amount of a surfactant is added thereto.

In the rinsing step, a wafer which has been developed using a developer including an organic solvent is subjected to a washing treatment using a rinsing liquid including an organic solvent. A method for the washing treatment is not particularly limited, for example, a method in which a rinsing liquid is continuously jetted on a substrate rotating at a constant speed (a rotation application method), a method in which a substrate is dipped in a tank filled with a rinsing liquid for a certain period of time (a dip method), a method in which a rinsing liquid is sprayed on a substrate surface (a spray method), or the like, and among these, a method in which a washing treatment is performed using the rotation application method, and a substrate is rotated at a rotation speed of 2,000 rpm to 4,000 rpm after washing, thereby removing the rinsing liquid from the substrate, is preferable. Further, it is also preferable that a heating step (postbaking) is included after the rinsing step. The developer and the rinsing liquid remaining between and inside the patterns are removed by the baking. The heating step after the rinsing step is performed, usually at 40° C. to 160° C., and preferably 70° C. to 95° C., usually for 10 seconds to 3 minutes, and preferably for 30 seconds to 90 seconds.

In a case where there is no step of performing washing with a rinsing liquid, for example, the development treatment method described in paragraphs [0014] to [0086] of JP2015-216403A can be adopted.

Moreover, the pattern forming method of the embodiment of the present invention may include a developing step using an organic developer and a developing step using an alkali developer. A portion having a low exposure intensity is removed by development using an organic developer, and a portion having a high exposure intensity is removed by performing development using an alkali developer. By virtue of multiple development processes in which development is performed in a plurality of times in such a manner, a pattern can be formed by keeping only a region with an intermediate exposure intensity from not being dissolved, so that a finer pattern than usual can be formed (the same mechanism as in paragraph [0077] of JP2008-292975A).

It is preferable that various materials (for example, a resist solvent, a developer, a rinsing liquid, a composition for forming an antireflection film, and a composition for forming a topcoat) used in the actinic ray-sensitive or radiation-sensitive composition in the embodiment of the present invention, and the pattern forming method of the embodiment of the present invention include no impurities such as metals, metal salts including halogen, acids, alkalis, and components including a sulfur atom or a phosphorus atom. Here, examples of the impurities including a metal atom include Na, K, Ca, Fe, Cu, Mn, Mg, Al, Cr, Ni, Zn, Ag, Sn, Pb, Li, and salts thereof.

The content of the impurities included in these materials is preferably 1 ppm or less, more preferably 1 ppb or less, still more preferably 100 parts per trillion (ppt) or less, and particularly preferably 10 ppt or less, and it is the most preferable that substantially no metal component is included (below a detection limit of the measuring apparatus).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a filter made of polytetrafluoroethylene, polyethylene, nylon, or the like is preferable. The filter may be a composite material in which these materials are combined with an ion exchange medium. As the filter, a filter which has been washed with an organic solvent in advance may be used. In the step of filtration using a filter, a plurality of kinds of filters linked in series or in parallel may be used. In a case of using a plurality of kinds of filters, a combination of filters having different pore diameters and/or materials may be used. In addition, various materials may be filtered plural times, and the step of filtering plural times may be a circulating filtration step.

In addition, examples of a method for reducing the impurities such as metals included in various materials include a method in which a raw material having a low metal content is selected as a raw material constituting various materials and the raw material constituting the various materials is subjected to filtration using a filter; and a method in which distillation under conditions suppressing contamination as much as possible by performing a lining with TEFLON (registered trademark), or the like in the inside of a device is performed. Preferred conditions for the filtration using a filter performed on the raw materials constituting various materials are the same ones as the above-mentioned conditions.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

In addition, as a method for reducing the impurities such as metals included in the organic treatment liquid of the present invention, a method in which a raw material having a low metal content is selected as a raw material constituting various materials, the raw material constituting the various materials is subjected to filtration using a filter; distillation under conditions suppressing contamination as much as possible by performing a lining with TEFLON (registered trademark) in the inside of a device; or the like. Preferred conditions for the filtration using a filter performed on the raw materials constituting various materials are the same ones as the above-mentioned conditions.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

[Storage Container]

As an organic solvent (also referred to as an "organic treatment liquid") which can be used for a developer and a rinsing liquid, it is preferable to use one stored in a storage container for storing an organic treatment liquid for patterning a chemically amplified or non-chemically amplified resist film, in which the container has a storage part. The storage container is preferably, for example, a storage container for storing an organic treatment liquid for patterning a resist film, in which the inner wall of the storage part being in contact with the organic treatment liquid is formed from a resin different from any of a polyethylene resin, a polypropylene resin, and a polyethylene-polypropylene resin, or of a metal subjected to a rust prevention/metal elution prevention treatment. An organic solvent to be used as an organic treatment liquid for patterning a resist film is stored in the storage part of the storage container, and the organic solvent jetted from the storage part can be used at the time of patterning the resist film.

In a case where the storage container further has a sealing part for sealing the storage part, the sealing part is also preferably formed of a resin different from one or more resins selected from the group consisting of a polyethylene resin, a polypropylene resin, and a polyethylene-polypropylene resin, or of a metal which has been subjected to a rust prevention/metal elution prevention treatment.

Here, the sealing part refers to a member capable of shielding the storage part from the outside air, and suitable examples thereof include a packing and an O ring.

The resin different from one or more resins selected from the group consisting of a polyethylene resin, a polypropylene resin, and a polyethylene-polypropylene resin is preferably a perfluoro resin.

Examples of the perfluoro resin include a tetrafluoroethylene resin (PTFE), a tetrafluoroethylene-perfluoroalkyl vinyl ether copolymer resin (PFA), a tetrafluoroethylene-hexafluoropropylene copolymer resin (FEP), a tetrafluoroethylene-ethylene copolymer resin (ETFE), a trifluoroethylene chloride-ethylene copolymer resin (ECTFE), a polyvinylidene fluoride resin (PVDF), a trifluoroethylene chloride resin (PCTFE), and a polyvinyl fluoride resin (PVF).

Particularly preferred examples of the perfluoro resin include a tetrafluoroethylene resin, a tetrafluoroethylene-perfluoroalkyl vinyl ether copolymer, and a tetrafluoroethylene-hexafluoropropylene copolymer resin.

Examples of the metal in the metal which has been subjected to a rust prevention/metal elution prevention treatment include carbon steel, alloy steel, nickel chromium steel, nickel chromium molybdenum steel, chromium steel, chromium molybdenum steel, and manganese steel.

As the rust prevention/metal elution prevention treatment, a coating technique is preferably applied.

The coating technique is roughly divided into three types of metal coating (various plating), inorganic coating (various chemical conversion treatments, glass, concrete, ceramics, and the like), and organic coating (a rust preventive oil, a paint, rubber, and plastics).

Preferred examples of the coating technique include a rust preventive oil, a rust inhibitor, a corrosion inhibitor, a chelate compound, a strippable plastic, and a surface treatment with a lining agent.

Among those, corrosion inhibitors, such as various chromates, nitrites, silicates, phosphates, oleic acid, dimer acid, carboxylic acids such as naphthenic acid, carboxylic acid metal soaps, sulfonates, amine salts, and esters (glycerol esters of higher fatty acids and phosphoric acid esters), chelate compounds such as ethylene diamine tetraacetic acid, gluconic acid, nitrilotriacetic acid, hydroxyethyl ethylene diamine triacetic acid, and diethylene triamine pentaacetic acid, and a fluorine resin lining are preferable. A phosphate treatment and the fluorine resin lining are particularly preferable.

Although it does not directly prevent rust as compared with a direct coating treatment, it is also preferable to adopt a "pretreatment" which is a step prior to a rust prevention treatment, as a treatment method leading to prolongation of the rust prevention period by a coating treatment.

As a specific example of such a pretreatment, a treatment for removing a variety of corrosive factors such as chlorides and sulfates present on the metal surface by washing or polishing can be suitably mentioned.

Specific examples of the storage container include the following ones.

FluoroPurePFA composite drum manufactured by Entegris Inc. (wetted inner surface; PFA resin lining)

Steel drum manufactured by JE Corporation (wetted inner surface; zinc phosphate-coated film)

Furthermore, examples of the storage container which can be used in the present invention include the containers described in paragraphs [0013] to [0030] of JP1999-021393A (JP-H11-021393A) and paragraphs [0012] to [0024] of JP1998-045961A (JP-H10-045961A).

In order to prevent breakdown of a chemical liquid pipe and various parts (a filter, an O-ring, a tube, and the like) due to electrostatic charging and subsequent electrostatic discharging, a conductive compound may be added to the organic treatment liquid of the present invention. The conductive compound is not particularly limited, but examples thereof include methanol. The addition amount of the conductive compound is not particularly limited, but is preferably 10% by mass or less, and more preferably 5% by mass or less from the viewpoint of maintaining preferable development characteristics. With regard to the members of the chemical liquid pipe, it is possible to use various pipes coated with stainless steel (SUS), or a polyethylene resin, a polypropylene resin, or a fluorine resin (a polytetrafluoroethylene resin, a perfluoroalkoxy resin, or the like), which has been subjected to an antistatic treatment. Similarly, a polyethylene resin, a polypropylene resin, or a fluorine resin (a polytetrafluoroethylene resin, a perfluoroalkoxy resin, or the like), which has been subjected to an antistatic treatment, can be used for a filter and an O-ring.

Moreover, generally, the developer and the rinsing liquid are stored in a waste liquid tank through a pipe after use. At that time, in a case where a hydrocarbon-based solvent is used as the rinsing liquid, there is a method of passing a solvent in which a resist is dissolved through a pipe again in order to prevent the resist dissolved in the developer from being precipitated and adhering to the back surface of the wafer, the side surface of the pipe or the like. Examples of the method of passing the solvent through the pipe include a method in which the back surface, the side surface, and the like of a substrate are washed with a solvent in which a resist is dissolved and then the solvent is allowed to flow after performing washing with a rinsing liquid, and a method of flowing a solvent in which a resist is dissolved so as to pass through a pipe while being not in contact with the resist.

The solvent to be passed through the pipe is not particularly limited as long as it can dissolve the resist, examples thereof include the above-mentioned organic solvents, and propylene glycol monomethyl ether acetate (PGMEA), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate, ethylene glycol monoethyl ether acetate, propylene glycol monomethyl ether (PGME), propylene glycol monoethyl ether, propylene glycol monopropyl ether, propylene glycol monobutyl ether, ethylene glycol monomethyl ether, ethylene glycol monoethyl ether, 2-heptanone, ethyl lactate, 1-propanol, acetone, or the like can be used. Among those, PGMEA, PGME, or cyclohexanone can be preferably used.

[Method for Manufacturing Electronic Device]

Moreover, the present invention further relates to a method for manufacturing an electronic device, the method including the above-described pattern forming method. The electronic device manufactured by the method for manufacturing an electronic device of an embodiment of the present invention is suitably mounted on electric or electronic equipment (for example, home electronics, office automation (OA)-related equipment, media-related equipment, optical equipment, and telecommunication equipment).

[Compound]

In addition, the present invention also relates to a compound represented by General Formula (1).

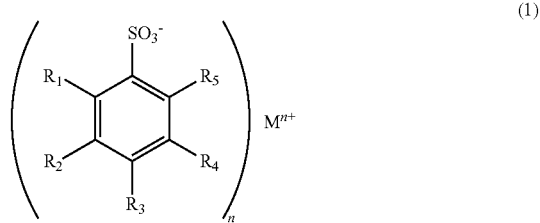

(1)

In General Formula (1), $R_1$, $R_3$, and $R_5$ each represent a group represented by General Formula (Ar).

$R_2$ and $R_4$ each independently represent a hydrogen atom or a substituent.

$M^{n+}$ represents a cation. n represents an integer of 1 or more.

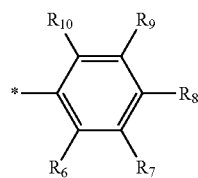

(Ar)

In General Formula (Ar), $R_6$ to $R_{10}$ each independently represent a hydrogen atom or a substituent. At least one of $R_6$, . . . , or $R_{10}$ is a group including a polar group, a group including a group having a polarity that increases through decomposition by an action of an acid, or a group including a group having a solubility in an alkali developer that increases through decomposition by an action of an alkali developer. * represents a bond to a benzene ring in General Formula (1).

$R_2$, $R_4$, $M^{n+}$, and n in General Formula (1) are the same as $R_2$, $R_4$, $M^{n+}$, and n in General Formula (1) in the compound (B), respectively.

$R_6$ to $R_{10}$ in General Formula (Ar) are the same as $R_6$ to $R_{10}$ in General Formula (Ar) in the compound (B), respectively.

EXAMPLES

Hereinbelow, the present invention will be described in more detail with reference to Examples. The materials, the amounts of materials used, the proportions, the treatment details, the treatment procedure, and the like shown in Examples below may be appropriately modified as long as the modifications do not depart from the spirit of the present invention. Therefore, the scope of the present invention should not be construed as being limited to Examples shown below.

<Resin (A)>

The structure of the repeating unit and a content (molar ratio) thereof, a weight-average molecular weight (Mw), and a dispersity (Mw/Mn) of the resin (A) used are shown below.

(A-1)

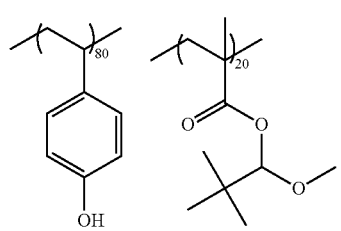

Mw = 8800
Mw/Mn = 1.6

(A-2)

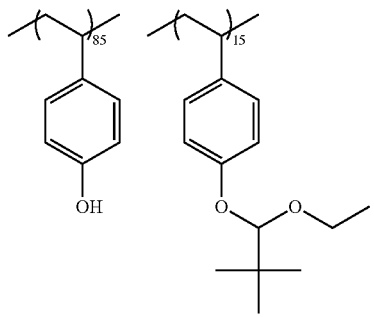

Mw = 4600
Mw/Mn = 1.2

(A-3)

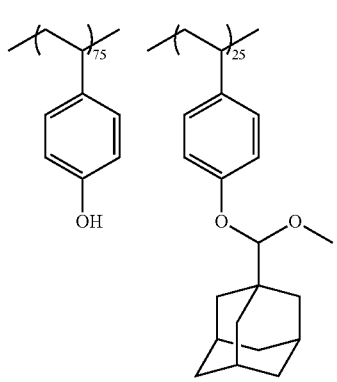

Mw = 5000
Mw/Mn = 1.4

(A-4)

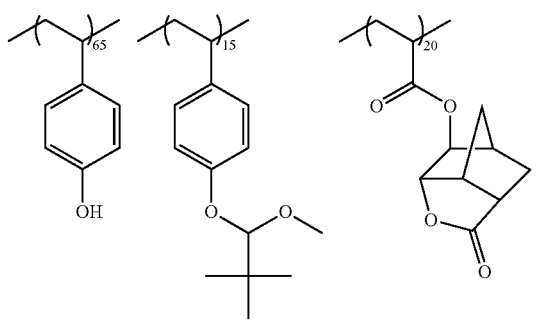

Mw = 6000
Mw/Mn = 1.6

(A-5)
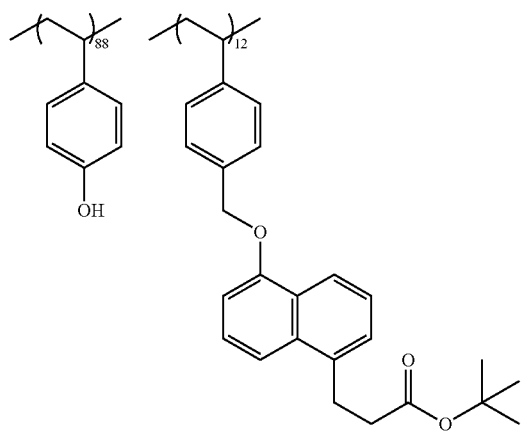
Mw = 7000
Mw/Mn = 1.4
(A-6)
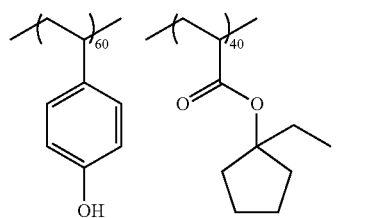
Mw = 5000
Mw/Mn = 1.6
(A-7)
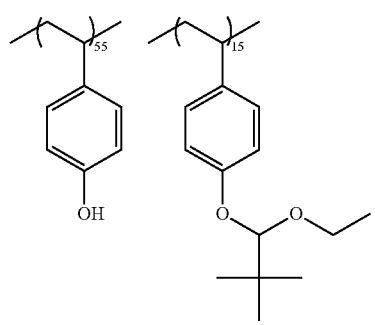
Mw = 12000
Mw/Mn = 1.7
(A-8)
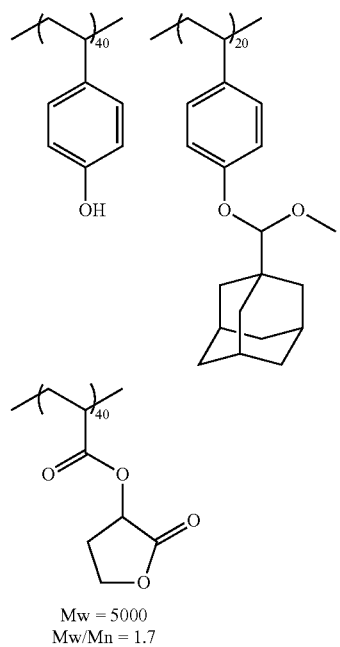
Mw = 5000
Mw/Mn = 1.7
(A-9)
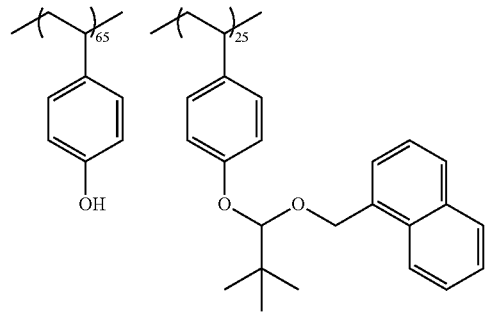
Mw = 9000
Mw/Mn = 1.6
(A-10)
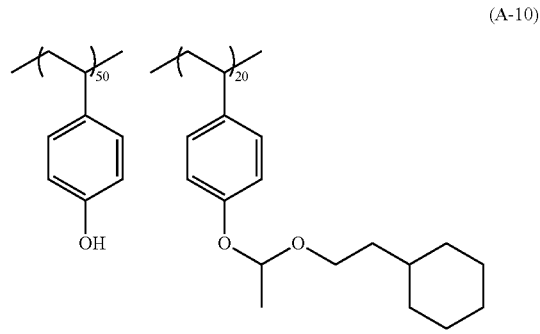

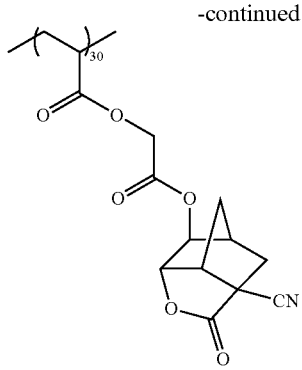
Mw = 15000
Mw/Mn = 1.7
(A-11)
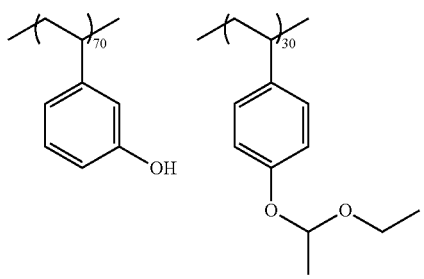
Mw = 8000
Mw/Mn = 1.7
(A-12)
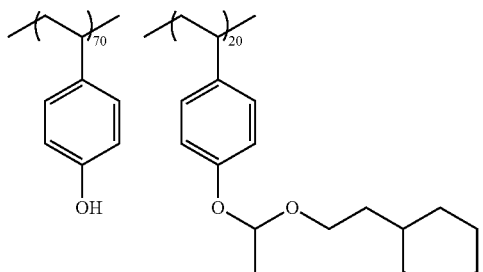
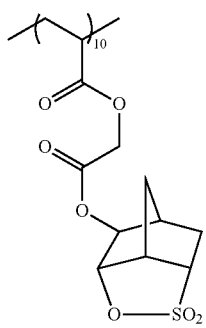
Mw = 7300
Mw/Mn = 1.5
(A-13)
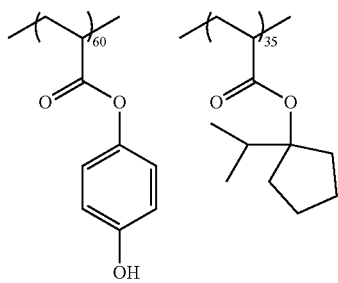
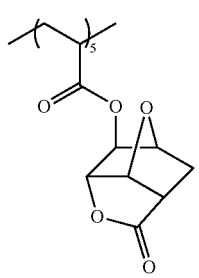
Mw = 12000
Mw/Mn = 1.6
(A-14)
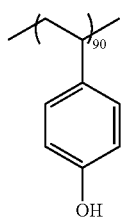
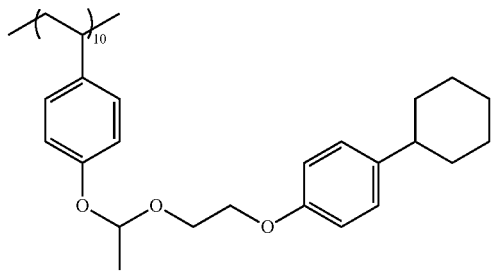
Mw = 18000
Mw/Mn = 1.2
(A-15)
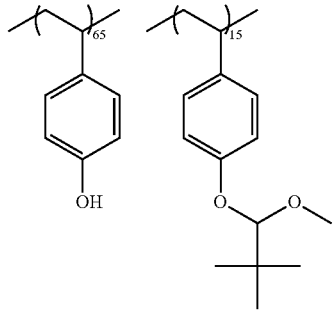

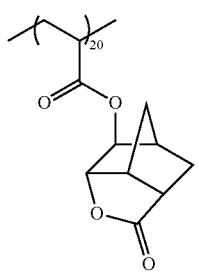
Mw = 5500
Mw/Mn = 1.7
(A-16)
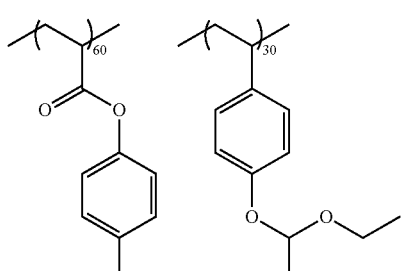
Mw = 9000
Mw/Mn = 1.6
(A-17)
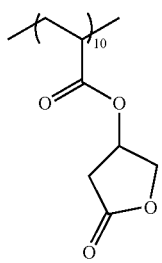
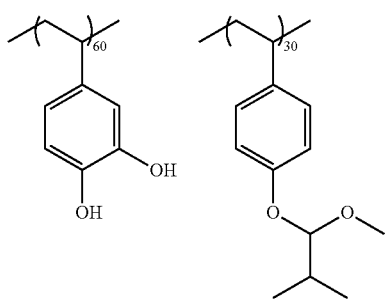
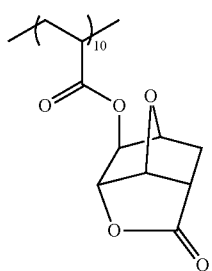
Mw = 9000
Mw/Mn = 1.6
(A-18)
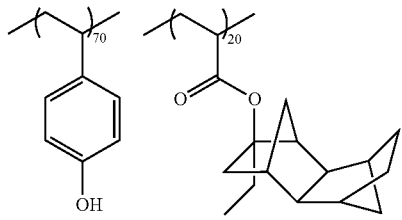
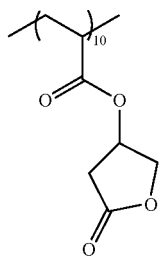
Mw = 10000
Mw/Mn = 1.6
(A-19)
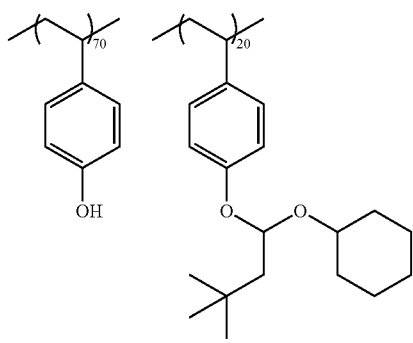
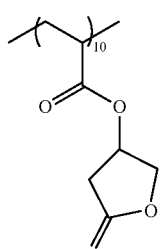
Mw = 5000
Mw/Mn = 1.7
(A-20)
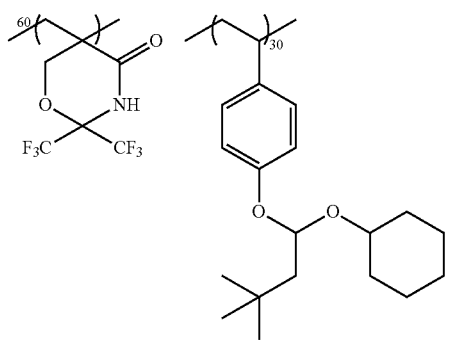

-continued
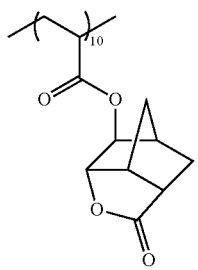
Mw = 8000
Mw/Mn = 1.4
(A-21)
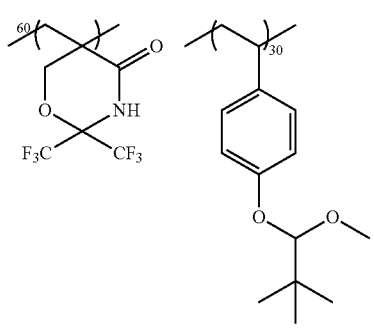
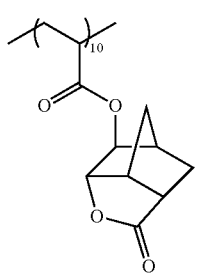
Mw = 9000
Mw/Mn = 1.6
(A-22)
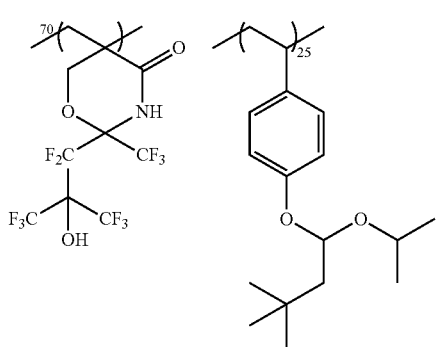
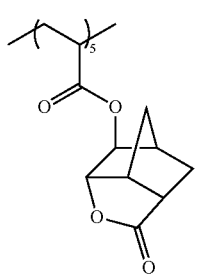
Mw = 10000
Mw/Mn = 1.7
-continued
(A-23)
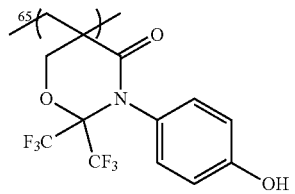
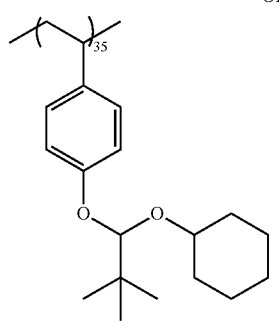
Mw = 17000
Mw/Mn = 1.7
(A-24)
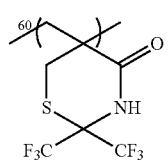
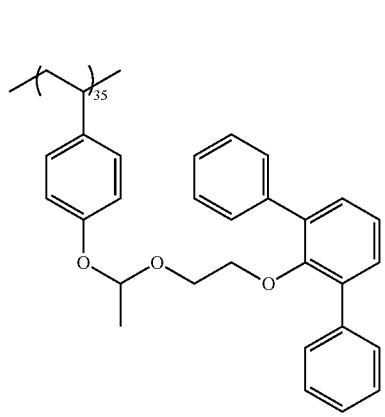
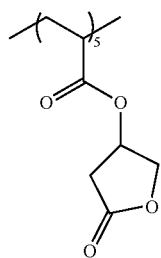
Mw = 9000
Mw/Mn = 1.7

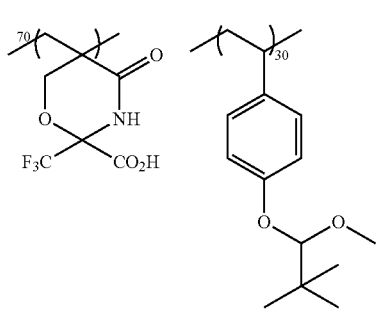
(A-25)
Mw = 13000
Mw/Mn = 1.7
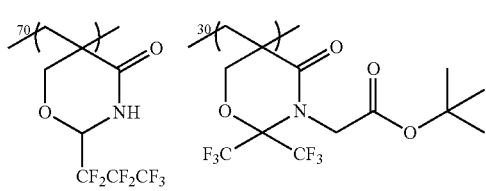
(A-26)
Mw = 5000
Mw/Mn = 1.5
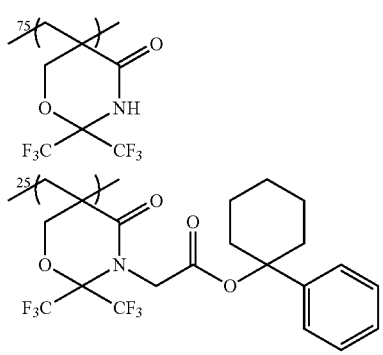
(A-27)
Mw = 7000
Mw/Mn = 1.8
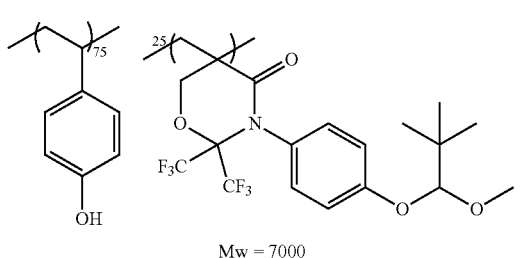
(A-28)
Mw = 7000
Mw/Mn = 1.8
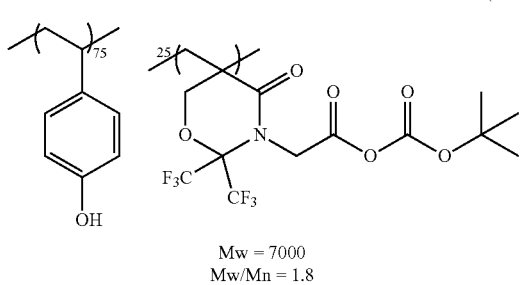
(A-29)
Mw = 7000
Mw/Mn = 1.8
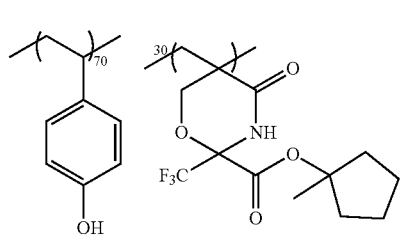
(A-30)
Mw = 8000
Mw/Mn = 1.8
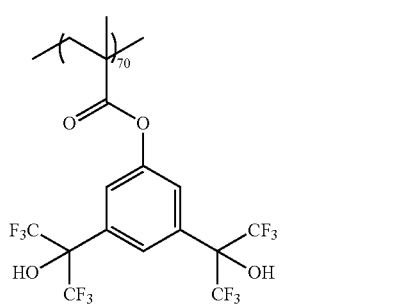
(A-31)
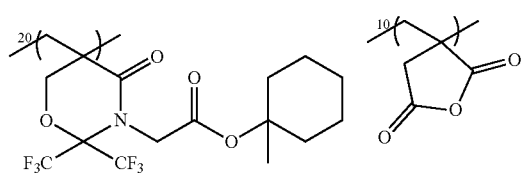
Mw = 7000
Mw/Mn = 1.7
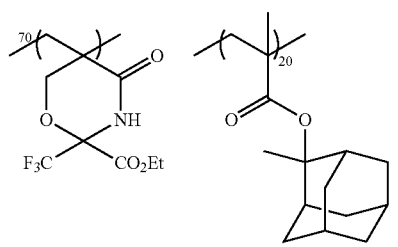
(A-32)
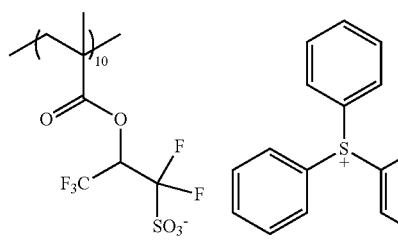
Mw = 8000
Mw/Mn = 1.6
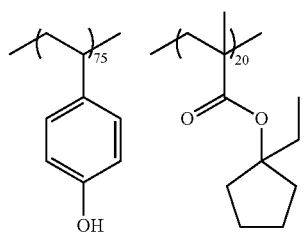
(A-33)

-continued

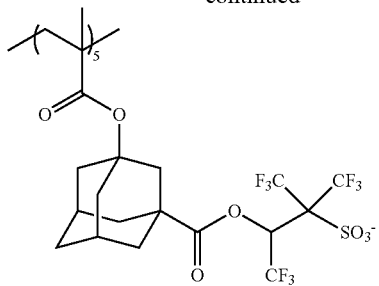

Mw = 10000
Mw/Mn = 1.5

(A-34)

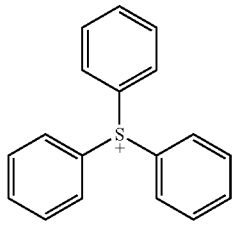

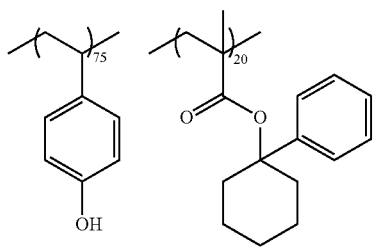

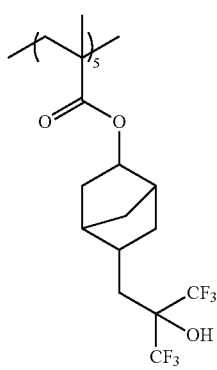

Mw = 7500
Mw/Mn = 1.6

Furthermore, the number attached to the leftmost repeating unit in each of the resin (A-20) to the resin (A-25) represents a content (molar ratio) of the repeating unit.

The number attached to each repeating unit in each of the resin (A-26) and the resin (A-27) represents a content (molar ratio).

The number attached to the repeating unit on the right side of each of the resin (A-28) to the resin (A-30) represent a content (molar ratio) of the repeating unit.

The number attached to the rightmost repeating unit in the resin (A-31) and the number attached to the second repeating unit from the right represent the content (molar ratio).

The number attached to the leftmost repeating unit in the resin (A-32) represents a content (molar ratio) of the repeating unit.

<Photoacid Generator (B)>

Synthesis Example 1: Synthesis of Photoacid Generator (B-2)

(1) (Synthesis of B-2-1)

40.0 g of 2,4,6-trichlorobenzenesulfonyl chloride was dissolved in 222 g of chloroform, the solution was cooled to 0° C., 15.9 g of isobutyl alcohol and 19.2 g of pyridine were added thereto, and the mixture was stirred at room temperature for 6 hours. 1 N hydrochloric acid was added to the reaction mixture to separate the layers, and the organic layer was washed with 1 N hydrochloric acid, saturated aqueous sodium hydrogen carbonate, and saturated saline, and dried by addition of anhydrous magnesium sulfate. After filtration, the solvent in the filtrate was evaporated under reduced pressure and vacuum-dried to obtain 32.3 g of a compound (B-2-1).

(2) (Synthesis of B-2-2)

5.00 g of the compound (B-2-1), 17.0 g of 4-(methoxycarbonyl)phenylboronic acid, 20.1 g of potassium phosphate, 645 mg of Sphos, 100 g of tetrahydrofuran, and 30 g of pure water were charged and degassed. Then, 177 mg of palladium acetate was added thereto and the mixture was stirred at 80° C. for 10 hours. Ethyl acetate was added to the reaction mixture to separate the layers, and the organic layer was washed with saturated saline and dried by addition of anhydrous magnesium sulfate. After filtration, the filtrate was passed through silica gel and washed with ethyl acetate. After evaporating the solvent under reduced pressure, 40 ml of chloroform was added to the crude product to dissolve it, 200 mg of activated carbon ANOX2 (manufactured by Osaka Gas Chemicals Co., Ltd.) and 100 mg of trimercaptotriazine were added thereto, and the mixture was stirred at room temperature for 2 hours (palladium as a catalyst was adsorbed to activated carbon and trimercaptotriazine). The activated carbon ANOX2 was removed by filtration, and the chloroform organic layer was washed with a 10-wt % aqueous sodium hydrogen carbonate solution, then washed twice with a 0.1-mol/L hydrochloric acid aqueous solution, and further washed twice with ultrapure water. After evaporating the solvent under reduced pressure, 50 ml of ethyl acetate was added to the residue, and the mixture was evaporated under reduced pressure to azeotropically dehydrate water. The obtained crude product was recrystallized from ethyl acetate/n-hexane and vacuum-dried to obtain 3.52 g of a compound (B-2-2).

(3) (Synthesis of B-2-3)

2.00 g of the compound (B-2-2), 40 g of acetonitrile, and 534 mg of sodium iodide were charged and stirred at 80° C. for 8 hours. The solid was separated by filtration, and washed with acetone and hexane. After vacuum-drying, 1.54 g of a compound (B-2-3) was obtained.

(4) (Synthesis of B-2)

1.50 g of the compound (B-2-3), 882 mg of triphenylsulfonium bromide, 10 g of methylene chloride, and 10 g of pure water were charged and stirred at room temperature for 3 hours. The organic phase was washed with pure water, the solvent was evaporated under reduced pressure, and the mixture was azeotropically distilled with isopropyl ether. The obtained crude product was recrystallized from ethyl acetate/isopropyl ether and vacuum-dried to obtain a compound (B-2) (2.10 g).

$^1$H-NMR spectrum (400 MHz, DMSO-d6) of the compound (B-2): δ=8.05-7.69 (m, 27H), 7.47 (s, 2H), 3.88 (s, 6H), and 3.86 (s, 3H).

Synthesis Example 2. Synthesis of Photoacid Generator (B-3)

By the same method as in the synthesis of the compound (B-2), except that 17.0 g of 4-(methoxycarbonyl) phenylboronic acid was changed to 13.0 g of 4-hydroxyphenylboronic acid, 2.23 g of a compound (B-3) was obtained.

$^1$H-NMR spectrum (400 MHz, DMSO-d6) of the compound (B-3): δ=9.53 (s, 1H), 9.12 (s, 2H), 7.90-7.19 (m, 21H), 7.14 (s, 2H), 6.84-6.63 (m, 6H).

Hereinafter, the compounds (B-1), and (B-4) to (B-80) were synthesized using the same method. In the software package 1, it was confirmed that the pKa of an acid generated by the compounds (B-1) to (B-80) was from −10 to 5. In addition, Me represents a methyl group.

The compounds (B-1) to (B-80) are each a compound obtained by combination of a cation shown in Table 1 and an anion shown in Table 1.

The following compounds (B'-1) and (B'-2) were used in Comparative Examples.

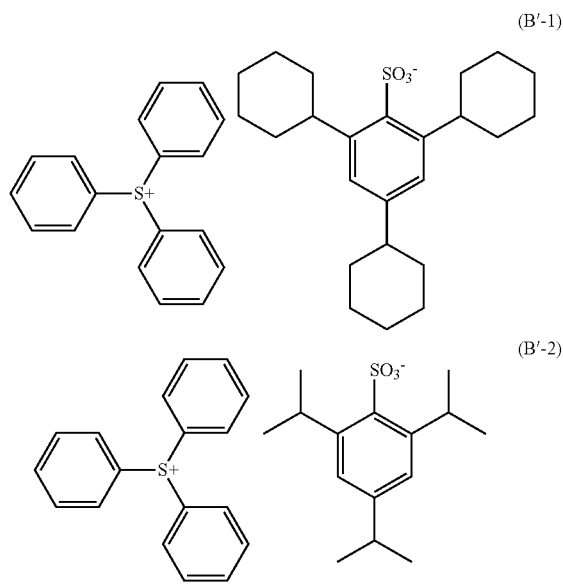

(B'-1)

(B'-2)

TABLE 1

| PAG | | Cation | | | | | | | | | | | | | |
|---|---|---|---|---|---|---|---|---|---|---|---|---|---|---|---|
| Anion | | 1 | 2 | 3 | 4 | 5 | 6 | 7 | 8 | 9 | 10 | 11 | 12 | 13 | 14 |
| | 1 | B-64 | B-78 | B-65 | | | | B-66 | | | | | | | |
| | 2 | B-73 | | | | | | | | | | | | | |
| | 3 | B-1 | B-4 | | | | | | | | | | | | |
| | 4 | B-3 | | | B-57 | | | B-37 | | | | | | | |
| | 5 | B-2 | B-43 | B-6 | | | | | | | B-59 | | | | |
| | 6 | | B-48 | | | | | | | | | | | | |
| | 7 | | B-32 | | | | | | | | | | | B-27 | |
| | 8 | B-28 | | | | | | | | | | | | | |
| | 9 | | | | B-80 | | | | | | | B-50 | | | |
| | 10 | B-53 | B-31 | | | | B-26 | | | B-56 | | | | | |
| | 11 | B-55 | | | | B-54 | | | | | | | | | |
| | 12 | | B-17 | | | | | B-61 | | | | | | | |
| | 13 | B-47 | | | | | | | | | | | | | |
| | 14 | B-79 | | | | | | | | | | | | | |
| | 15 | | | | B-70 | | | | | | | | | | |
| | 16 | | B-23 | | | | | | | | | B-25 | | | |
| | 17 | B-29 | | | | | | | | | | | B-44 | | B-24 |
| | 18 | | B-46 | | | | | | | | | | | | |
| | 19 | B-35 | | | B-33 | | B-58 | | | | | | | | |
| | 20 | B-75 | B-72 | | | | | | B-36 | | | | | | |
| | 21 | B-76 | B-18 | | | | | | | | | | | | |
| | 22 | | | | | | | | | | | | B-19 | | |
| | 23 | B-52 | B-34 | | | | | | | | | | | | |
| | 24 | | B-38 | | B-14 | | | | | | | | | | |
| | 25 | | | | | | | | | | | | | B-20 | |
| | 26 | B-62 | B-67 | | | | | | | | | | | | |
| | 27 | B-8 | | | | | | | | | | | | | |

TABLE 1-continued
| 28 | B-12 |      |      |      |      | B-45 |      |      |      |
| 29 | B-16 |      |      |      |      |      |      | B-49 |      |
| 30 |      | B-69 |      |      | B-51 |      |      | B-71 |      |
| 31 | B-13 | B-68 |      |      |      |      |      |      |      |
| 32 | B-15 |      | B-63 |      |      |      |      |      |      |
|       |    | Cation |      |      |      |      |      |      |      |      |      |      |      |      |
|-------|----|--------|------|------|------|------|------|------|------|------|------|------|------|------|
| PAG   |    | 15     | 16   | 17   | 18   | 19   | 20   | 21   | 22   | 23   | 24   | 25   | 26   | 27   |
| Anion | 1  | B-77   | B-5  |      |      |      |      |      |      |      | B-42 |      |      |      |
|       | 2  |        | B-74 | B-7  |      |      |      |      |      |      |      |      |      |      |
|       | 3  |        |      |      |      |      |      | B-39 |      |      |      |      |      | B-40 |
|       | 4  |        |      |      | B-11 |      |      |      |      |      |      |      |      |      |
|       | 5  |        |      |      |      |      |      |      |      |      |      | B-9  |      |      |
|       | 6  |        |      |      |      |      |      |      |      |      |      |      |      |      |
|       | 7  |        |      |      |      |      |      |      |      |      |      |      |      |      |
|       | 8  |        |      |      |      |      |      |      |      | B-22 |      |      |      |      |
|       | 9  |        |      |      |      |      |      |      | B-21 |      |      |      |      |      |
|       | 10 |        |      |      |      |      |      |      |      |      |      |      |      |      |
|       | 11 |        |      |      |      | B-60 |      |      |      |      |      |      |      |      |
|       | 12 |        |      |      |      |      |      |      |      |      |      |      |      |      |
|       | 13 |        |      |      |      |      |      |      |      |      |      |      |      |      |
|       | 14 |        |      |      |      |      |      |      |      |      |      |      |      |      |
|       | 15 |        |      |      |      |      |      |      |      |      |      |      |      |      |
|       | 16 |        |      |      |      |      |      |      |      |      |      |      |      |      |
|       | 17 |        |      |      |      |      |      |      |      |      |      |      |      |      |
|       | 18 |        |      |      |      |      |      |      |      |      |      |      |      |      |
|       | 19 |        |      |      |      |      |      |      |      |      |      |      |      |      |
|       | 20 |        |      |      |      |      |      |      |      |      |      |      |      |      |
|       | 21 |        |      |      |      |      |      |      |      |      |      |      |      |      |
|       | 22 |        |      |      |      |      |      |      |      |      |      |      |      |      |
|       | 23 |        |      |      |      |      |      |      |      |      |      |      |      |      |
|       | 24 |        |      |      |      |      |      | B-10 |      |      |      |      |      |      |
|       | 25 |        |      |      |      |      |      |      |      |      |      |      |      |      |
|       | 26 |        |      |      |      |      |      |      |      |      |      |      |      |      |
|       | 27 |        |      |      |      |      |      |      |      |      |      |      | B-41 |      |
|       | 28 |        |      |      |      |      |      |      |      |      |      |      |      |      |
|       | 29 | B-30   |      |      |      |      |      |      |      |      |      |      |      |      |
|       | 30 |        |      |      |      |      |      |      |      |      |      |      |      |      |
|       | 31 |        |      |      |      |      |      |      |      |      |      |      |      |      |
|       | 32 |        |      |      |      |      |      |      |      |      |      |      |      |      |
The structures of the cations shown in Table 1 are shown below. Me represents a methyl group and Bu represents an n-butyl group.
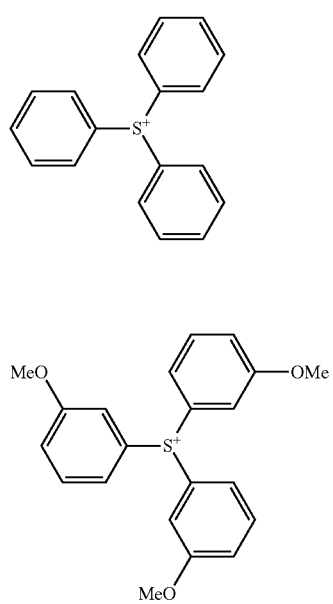
1
2
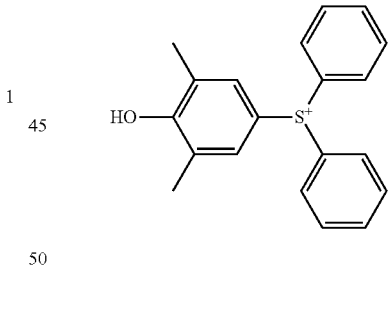
3
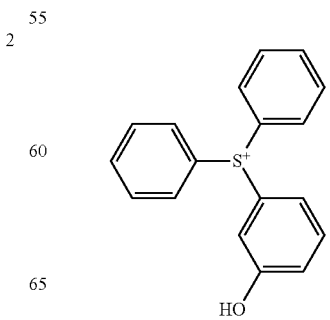
4

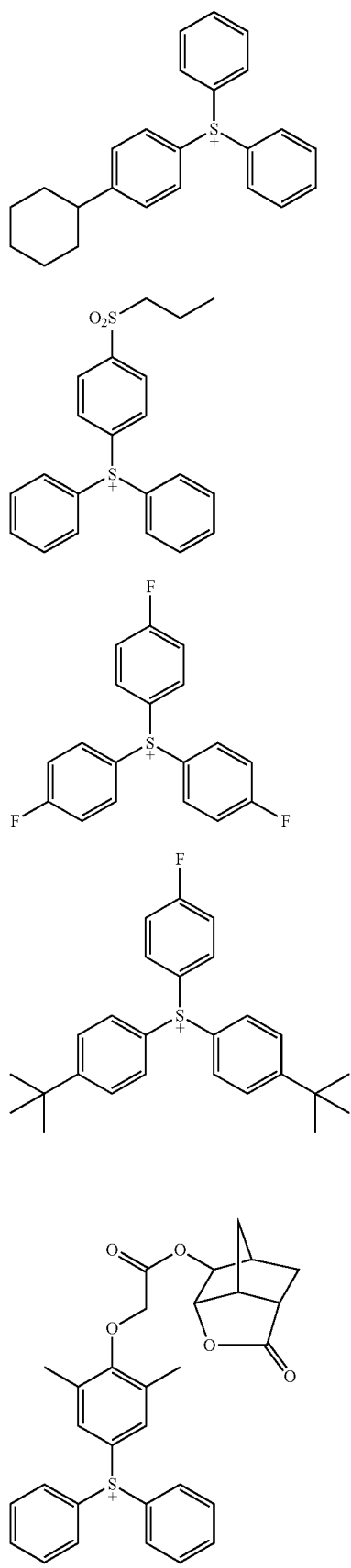
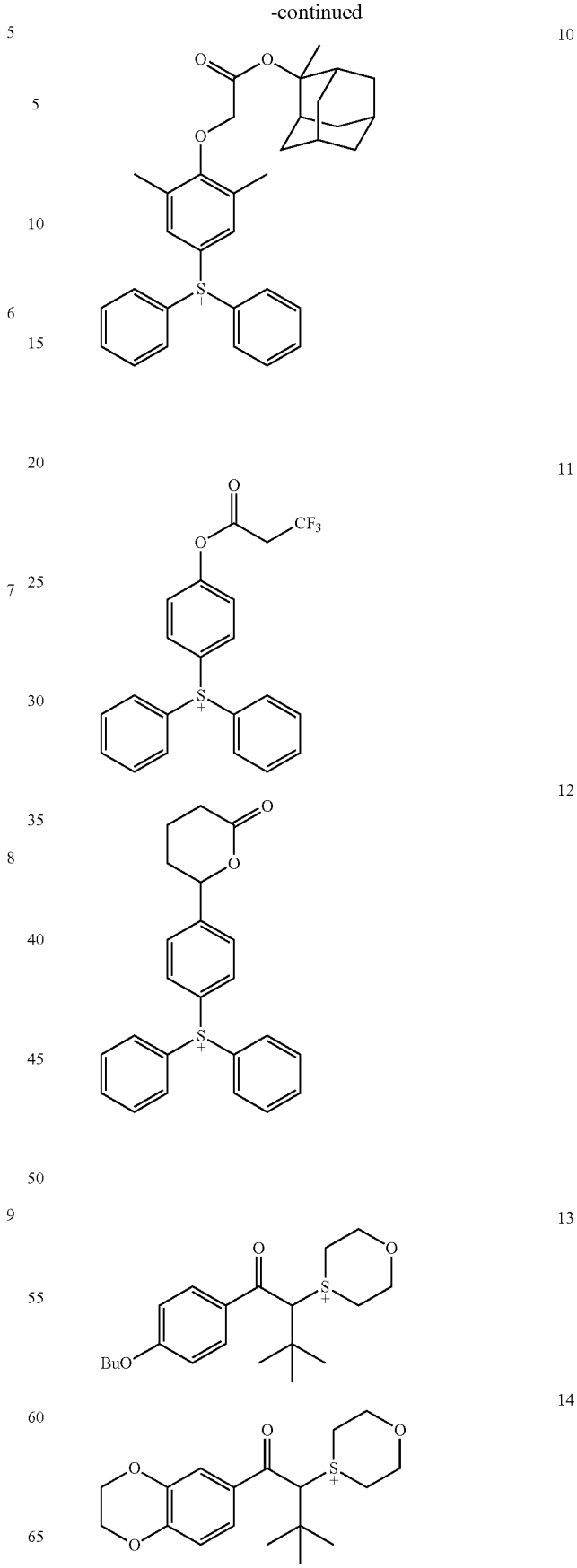

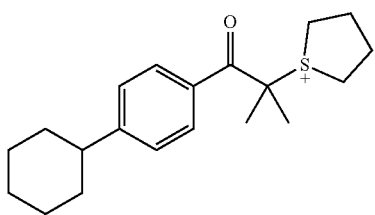
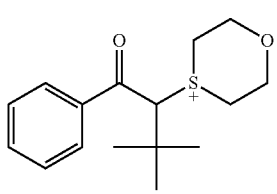
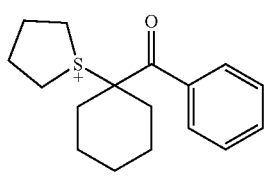
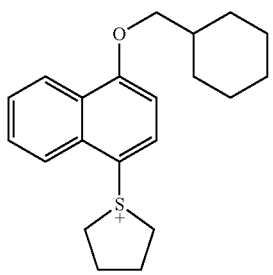
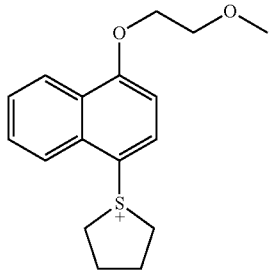
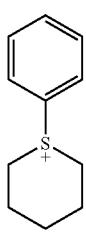
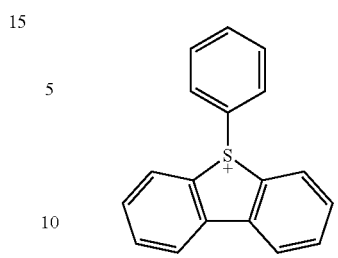
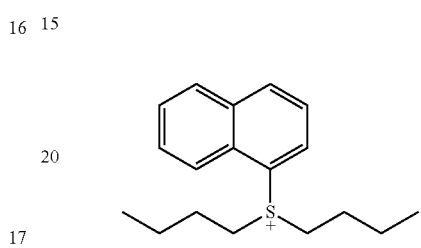
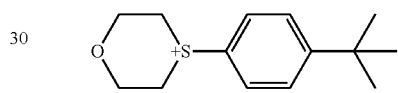
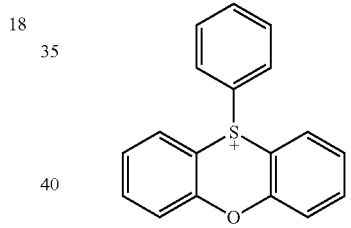
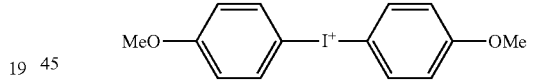
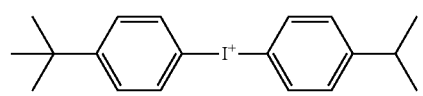
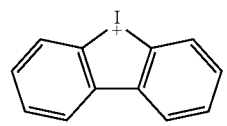
The structures of the anions shown in Table 1 are shown below. Me represents a methyl group and Bu represents an n-butyl group.

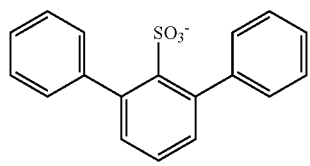 1
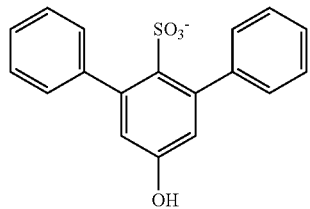 2
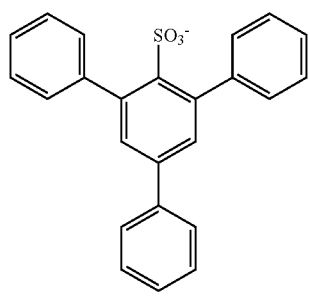 3
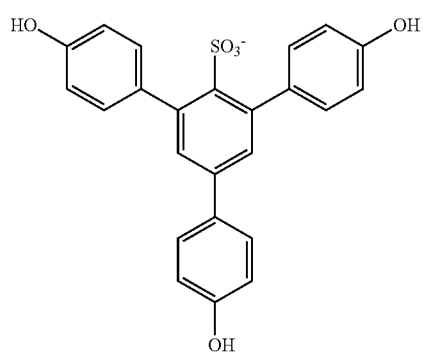 4
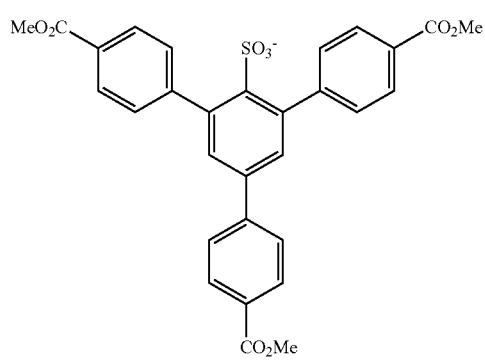 5
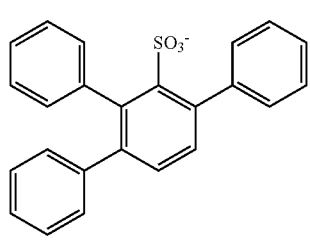 6

7
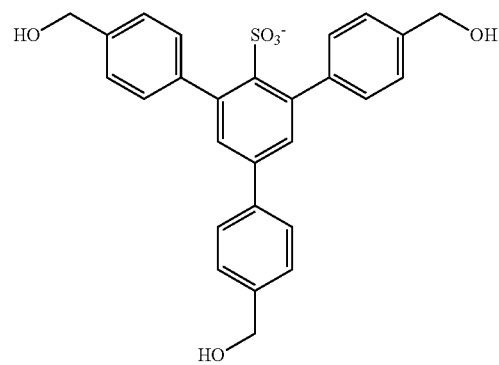
8
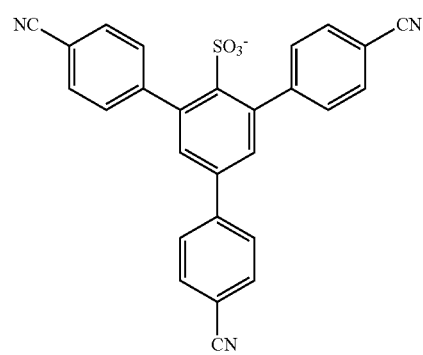
9
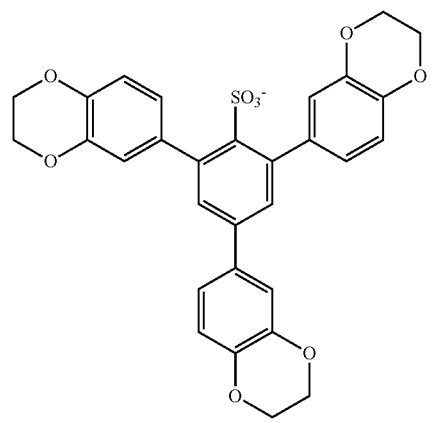
10
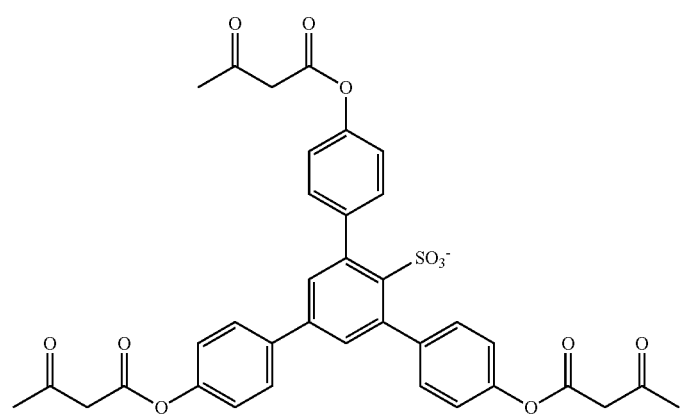

-continued
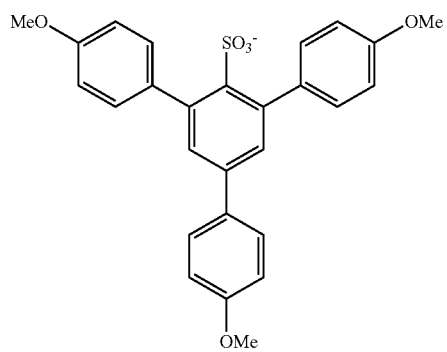
11
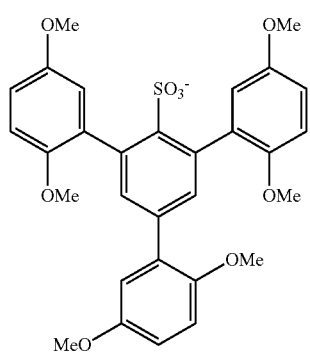
12
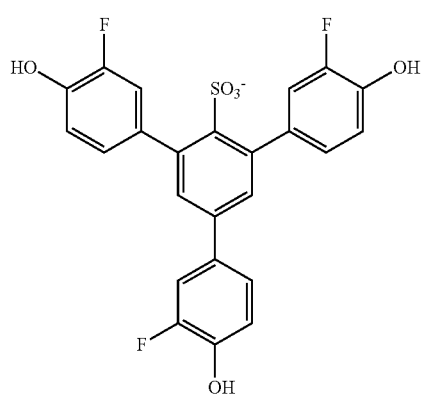
13
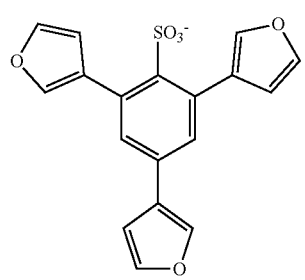
14
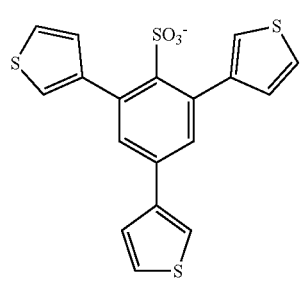
15

16
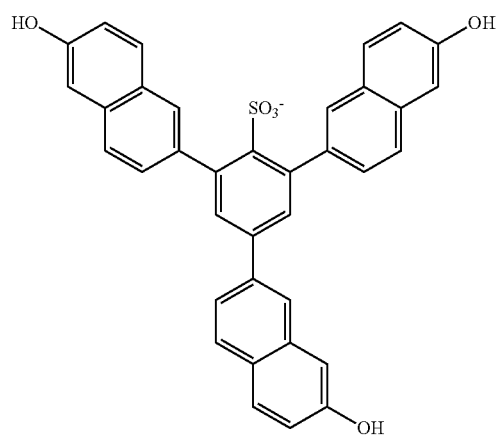
17
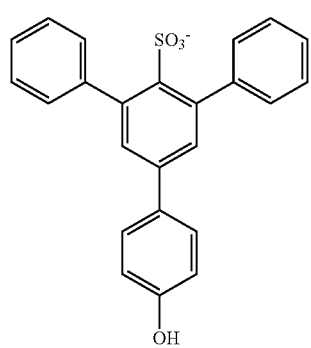
18
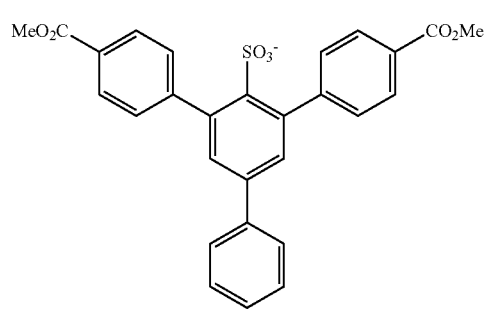
19
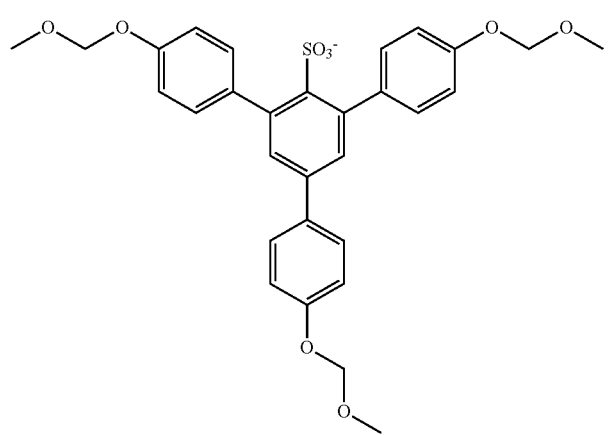

-continued
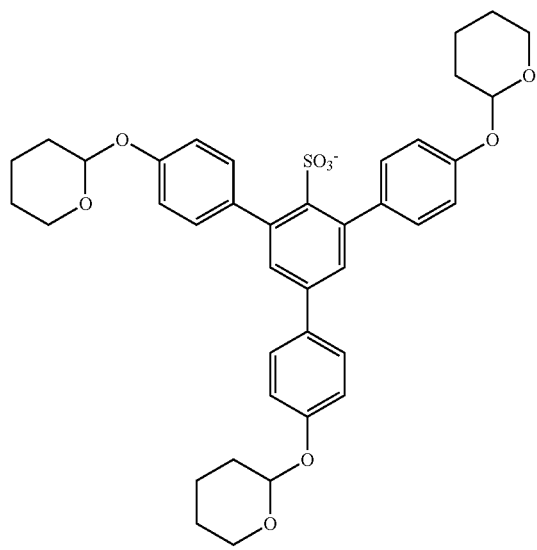
20
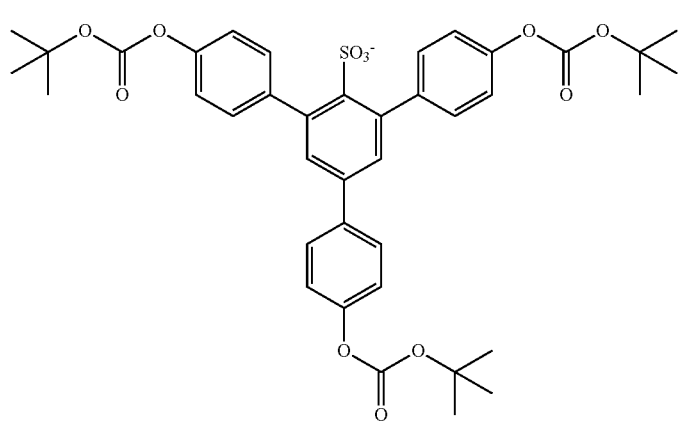
21
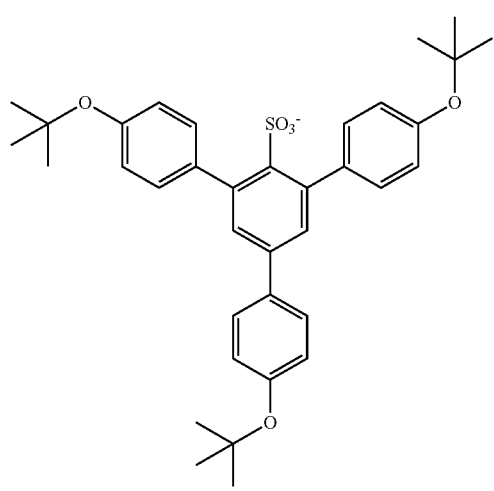
22

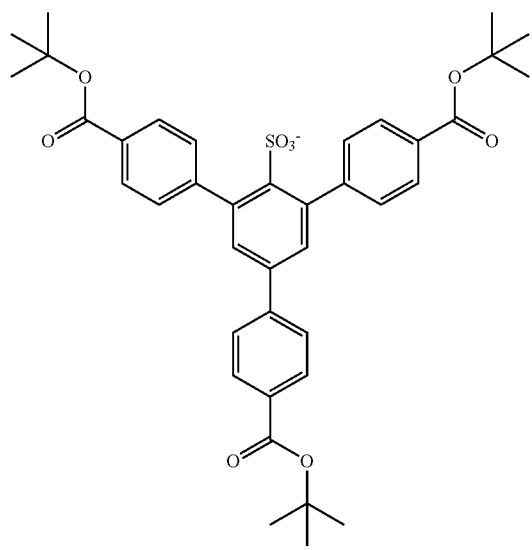
23
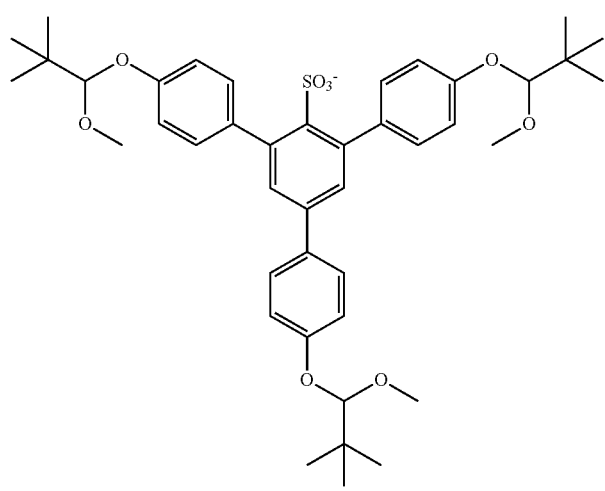
24
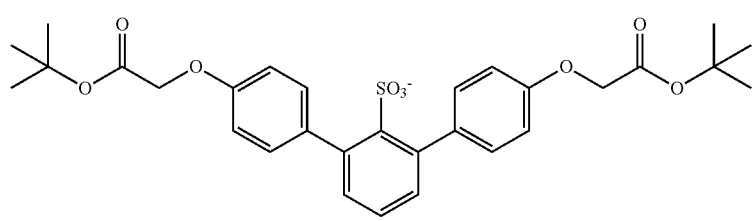
25

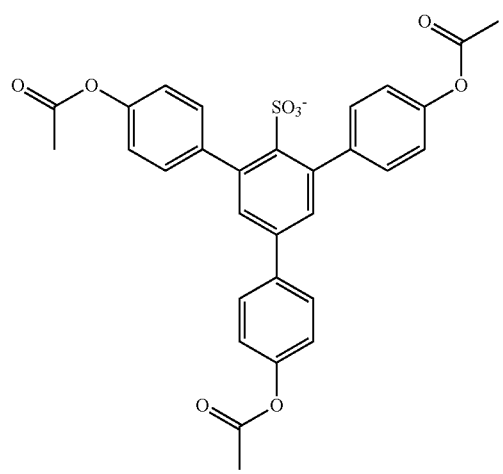
26
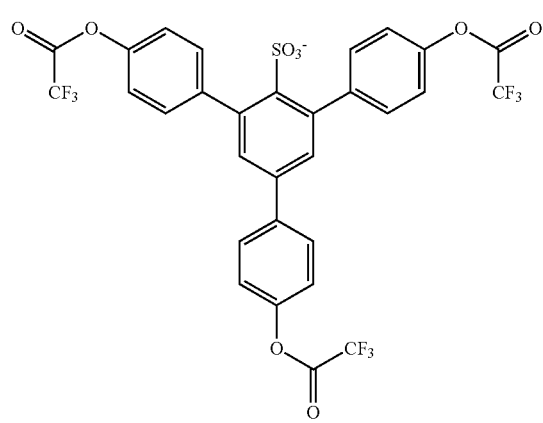
27
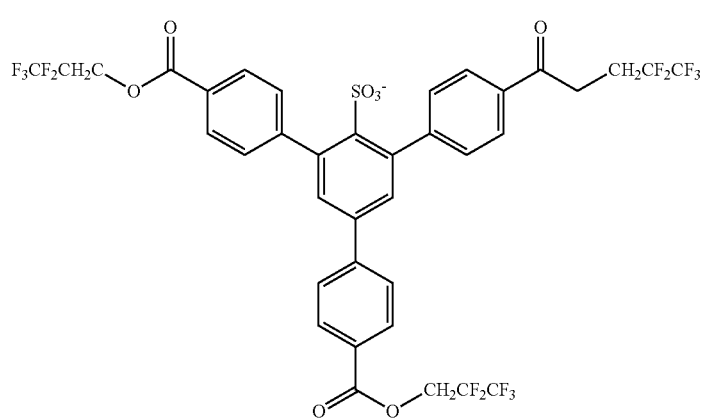
28
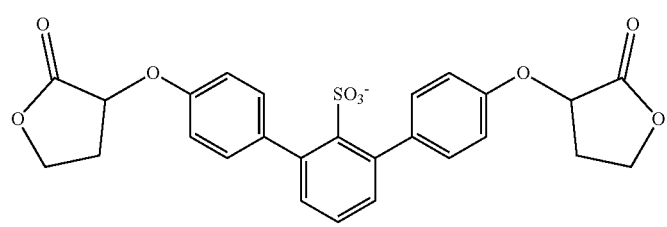
29

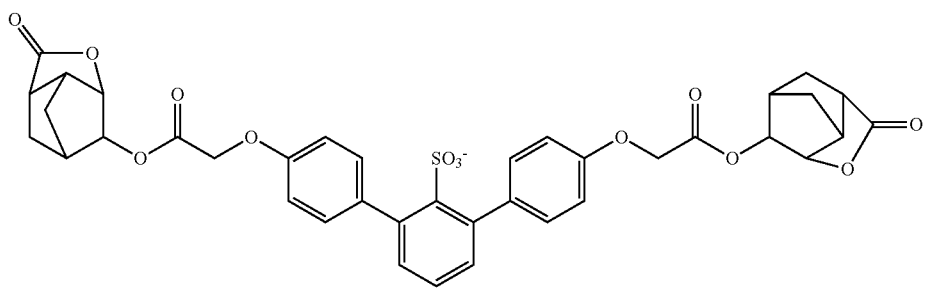
30
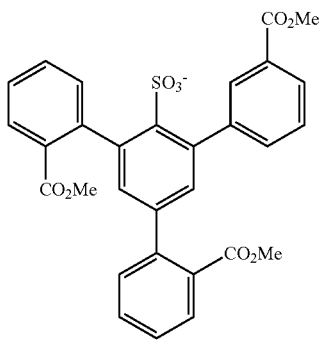
31
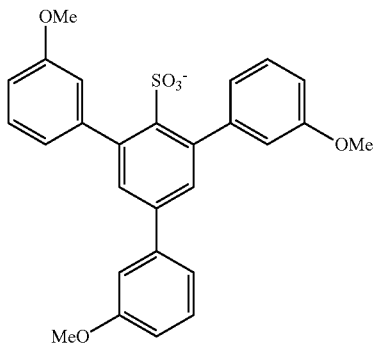
32
<Acid Diffusion Control Agent>
The structures of the acid diffusion control agents used are shown below.
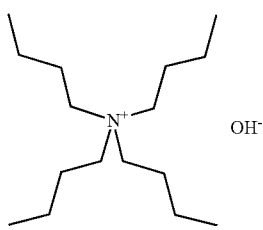
(C-1)
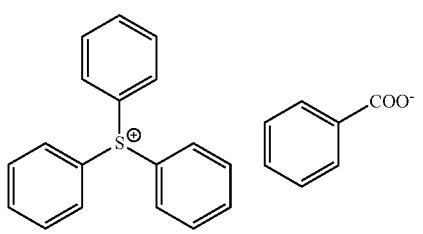
(C-2)
-continued
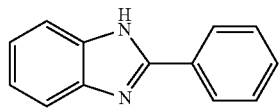
(C-3)
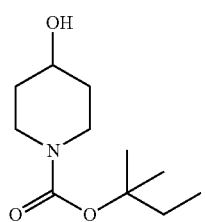
(C-4)

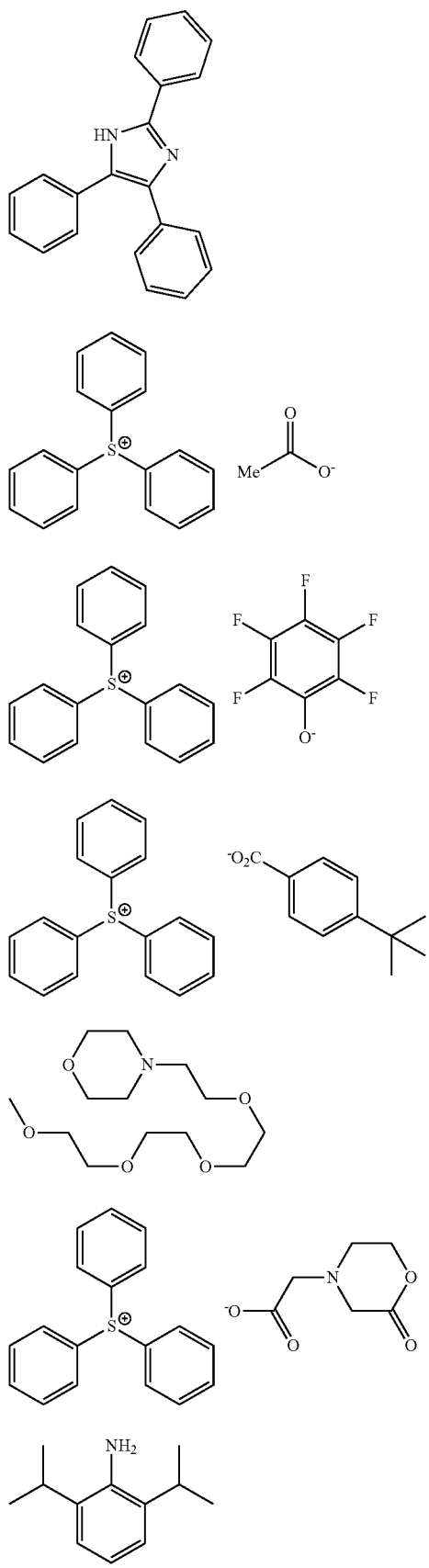

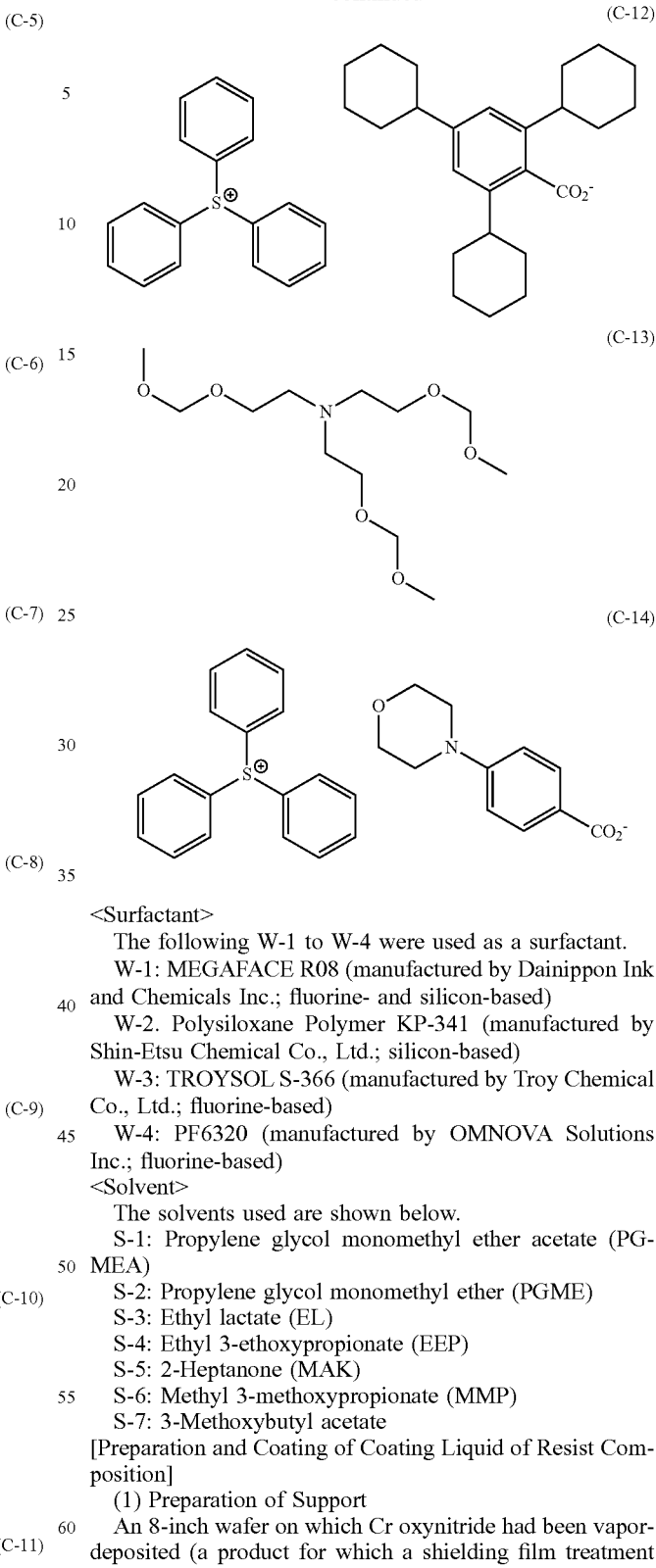

<Surfactant>

The following W-1 to W-4 were used as a surfactant.

W-1: MEGAFACE R08 (manufactured by Dainippon Ink and Chemicals Inc.; fluorine- and silicon-based)

W-2. Polysiloxane Polymer KP-341 (manufactured by Shin-Etsu Chemical Co., Ltd.; silicon-based)

W-3: TROYSOL S-366 (manufactured by Troy Chemical Co., Ltd.; fluorine-based)

W-4: PF6320 (manufactured by OMNOVA Solutions Inc.; fluorine-based)

<Solvent>

The solvents used are shown below.

S-1: Propylene glycol monomethyl ether acetate (PGMEA)
S-2: Propylene glycol monomethyl ether (PGME)
S-3: Ethyl lactate (EL)
S-4: Ethyl 3-ethoxypropionate (EEP)
S-5: 2-Heptanone (MAK)
S-6: Methyl 3-methoxypropionate (MMP)
S-7: 3-Methoxybutyl acetate

[Preparation and Coating of Coating Liquid of Resist Composition]

(1) Preparation of Support

An 8-inch wafer on which Cr oxynitride had been vapor-deposited (a product for which a shielding film treatment used for an ordinary photomask blank had been carried out) was prepared.

(2) Preparation of Resist Composition

The components shown in Table 2 below were dissolved in a solvent to prepare a solution having a solid content (concentration of solid contents) shown in Table 2, and this solution was filtered through a polyethylene filter having a pore size of 0.03 m to prepare a resist composition.

(3) Preparation of Resist Film

A resist composition was applied onto the 8-inch wafer using a spin coater Mark8 manufactured by Tokyo Electron Limited, and dried on a hot plate at 120° C. for 600 seconds to obtain a resist film having a film thickness of 100 nm. That is, a resist-coated wafer was obtained.

[EB Exposure and Development]

(4) Preparation of Resist Pattern

The resist film obtained in (3) was subjected to pattern irradiation using an electron beam drawing apparatus (manufactured by Advantest Corporation; F7000S, accelerating voltage: 50 KeV). After the irradiation, the film was heated on a hot plate at 100° C. for 600 seconds, dipped using a 2.38%-by-mass aqueous tetramethylammonium hydroxide (TMAH) solution for 60 seconds, then rinsed with water for 30 seconds, and dried.

[Evaluation]

(5) Evaluation of Resist Pattern

The obtained pattern was evaluated on resolution and development defects by the following methods. The results are shown in Table 3 below.

The irradiation energy upon resolution of a 1:1 line-and-space pattern with a line width of 50 nm was defined as a sensitivity (Eop).

<L/S Resolution>

A marginal resolving power (a minimum line width at which lines and spaces (line:space=1:1) are separated and resolved) at an exposure dose showing the sensitivity (Eop) was taken as a resolving power (nm).

<Isolated Space Pattern (IS) Resolution>

A marginal resolving power (a minimum space width at which lines and spaces are separated and resolved) of an isolated space (line:space=100:1) at the sensitivity (Eop) was determined. Then, this value was defined as an "isolated space pattern resolving power (nm)". A smaller value thereof indicates better performance.

<Development Defects>

Using a defect inspection apparatus, KLA 2360 (trade name), manufactured by KLA Tencor Ltd., a 1:1 line-and-space pattern with a line width of 50 nm formed at the sensitivity (Eop) was measured by setting a pixel size of the defect inspection apparatus to 0.16 μm and a threshold value to 20 to detect defects (defects/cm$^2$) extracted from a difference produced at the time of superposing pixel units on a reference image, and the number of the defects per unit area (defects/cm$^2$) was computed. Then, by performing a defect review, the development defects were classified and extracted from all the defects, and the number of development defects per unit area (defects/cm$^2$) was computed. The value of less than 0.5 was designated as A, the value of 0.5 or more and less than 1.0 was designated as B, the value of 1.0 or more and less than 5.0 was designated as C, and a value of 5.0 or more was designated as D. A smaller value thereof indicates better performance.

Furthermore, in Table 2 below, the content (% by mass) of each component other than the solvent means a content ratio with respect to the total solid content. In addition, the content ratio (% by mass) of the solvent used with respect to all the solvents is described in Table 2 below.

TABLE 2

| Resist composition | Resin (A) Compound | Resin (A) Content (% by mass) | Acid generator (B) Compound | Acid generator (B) Content (% by mass) | Acid diffusion control agent Compound | Acid diffusion control agent Content (% by mass) | Surfactant Type (0.01% by mass) | Solvent Solvent 1 | Solvent Content ratio of solvent 1 (% by mass) | Solvent Solvent 2 | Solvent Content ratio of solvent 2 (% by mass) | Solvent Solvent 3 | Solvent Content ratio of solvent 3 (% by mass) | Solid content (% by mass) |
|---|---|---|---|---|---|---|---|---|---|---|---|---|---|---|
| R-1 | (A-1) | 93.01 | (B-1) | 6.78 | (C-1) | 020 | W-1 | S-1 | 60 | S-2 | 40 | — | — | 26 |
| R-2 | (A-2) | 94.11 | (B-2) | 5.78 | (C-3) | 010 | W-3 | S-1 | 90 | S-4 | 10 | — | — | 28 |
| R-3 | (A-3) | 96.55 | (B-5) | 3.35 | (C-2) | 010 | — | S-1 | 80 | S-2 | 10 | S-3 | 10 | 31 |
| R-4 | (A-4) | 92.21 | (B-8) | 7.68 | (C-4) | 010 | W-4 | S-1 | 60 | S-5 | 40 | — | — | 28 |
| R-5 | (A-5) | 89.89 | (B-7) | 10.00 | (C-3) | 010 | W-2 | S-1 | 20 | S-2 | 20 | S-3 | 60 | 36 |
| R-6 | (A-2) | 88.68 | (B-10) | 11.22 | (C-1) | 010 | — | S-1 | 30 | S-3 | 30 | S-7 | 40 | 29 |
| R-7 | (A-3) | 93.11 | (B-11) | 6.78 | (C-5) | 010 | W-1 | S-1 | 20 | S-2 | 20 | S-3 | 60 | 30 |
| R-8 | (A-4) | 90.31 | (B-9) | 9.58 | (C-3) | 010 | W-3 | S-1 | 20 | S-4 | 20 | S-6 | 60 | 26 |
| R-9 | (A-2) | 91.16 | (B-6) | 8.74 | (C-1) | 010 | — | S-1 | 90 | S-4 | 10 | — | — | 28 |
| R-10 | (A-6) | 92.10 | (B-2) | 7.79 | (C-2) | 010 | W-1 | S-1 | 80 | S-2 | 10 | S-3 | 10 | 31 |
| R-11 | (A-3) | 86.37 | (B-3) | 13.50 | (C-4) | 012 | W-3 | S-1 | 20 | S-2 | 20 | S-3 | 60 | 36 |
| R-12 | (A-1) | 84.90 | (B-2) | 15.00 | (C-1) | 010 | — | S-1 | 30 | S-2 | 30 | S-7 | 40 | 29 |
| R-13 | (A-3) | 90.97 | (B-12) | 8.92 | (C-4) | 010 | W-4 | S-1 | 20 | S-2 | 20 | S-3 | 60 | 30 |
| R-14 | (A-4) | 86.60 | (B-4) | 13.25 | (C-5) | 014 | W-2 | S-1 | 20 | S-2 | 20 | S-3 | 60 | 32 |
| R-15 | (A-5) | 89.97 | (B-8) | 9.87 | (C-1) | 016 | — | S-1 | 40 | S-3 | 60 | — | — | 31 |
| R-16 | (A-2) | 95.05 | (B-2) | 4.85 | (C-3) | 010 | — | S-1 | 20 | S-2 | 20 | S-3 | 60 | 29 |
| R-17 | (A-2) | 93.55 | (B-7) | 6.25 | (C-3) | 020 | — | S-1 | 30 | S-2 | 20 | S-3 | 50 | 28 |
| R-18 | (A-1) | 90.89 | (B-1) | 9.00 | (C-1) | 010 | W-2 | S-1 | 20 | S-3 | 80 | — | — | 28 |
| R-19 | (A-3) | 89.30 | (B'-1) | 10.50 | (C-2) | 020 | — | S-1 | 20 | S-3 | 20 | S-5 | 60 | 32 |
| R-20 | (A-2) | 92.92 | (B'-1) | 6.87 | (C-3) | 020 | W-2 | S-1 | 40 | S-3 | 30 | S-7 | 30 | 31 |
| R-21 | (A-4) | 90.02 | (B'-2) | 9.87 | (C-1) | 010 | W-1 | S-1 | 30 | S-2 | 20 | S-3 | 50 | 29 |
| R-22 | (A-7) | 94.23 | (B-7) | 5.62 | (C-6) | 0.14 | W-1 | S-1 | 60 | S-2 | 40 | — | — | 2.7 |
| R-23 | (A-2) | 90.32 | (B-8) | 9.51 | (C-10) | 0.16 | W-3 | S-1 | 80 | S-4 | 10 | — | — | 2.6 |
| R-24 | (A-3) | 87.22 | (B-15) | 12.58 | (C-2) | 0.20 | — | S-1 | 80 | S-2 | 10 | S-3 | 10 | 3.0 |
| R-25 | (A-8) | 89.76 | (B-8) | 10.05 | (C-9) | 0.18 | W-4 | S-1 | 60 | S-3 | 40 | — | — | 2.9 |
| R-26 | (A-4) | 88.46 | (B-16) | 11.43 | (C-6) | 0.10 | W-2 | S-1 | 20 | S-2 | 20 | S-3 | 60 | 3.4 |
| R-27 | (A-2) | 85.41 | (B-14) | 14.47 | (C-1) | 0.12 | — | S-1 | 40 | S-4 | 30 | S-7 | 30 | 3.5 |
| R-28 | (A-9) | 92.61 | (B-11) | 7.28 | (C-7) | 0.10 | W-1 | S-1 | 30 | S-2 | 20 | S-5 | 50 | 3.0 |
| R-29 | (A-10) | 89.44 | (B-9) | 10.39 | (C-3) | 0.16 | W-3 | S-1 | 30 | S-2 | 20 | S-6 | 50 | 2.8 |
| R-30 | (A-5) | 91.16 | (B-12) | 8.74 | (C-10) | 0.10 | — | S-1 | 90 | S-5 | 10 | — | — | 2.8 |
| R-31 | (A-7) | 92.31 | (B-13) | 7.58 | (C-11) | 0.10 | W-1 | S-1 | 80 | S-2 | 10 | S-6 | 10 | 2.9 |
| R-32 | (A-8) | 91.35 | (B-2) | 8.53 | (C-8) | 0.12 | — | S-1 | 70 | S-2 | 20 | S-4 | 10 | 2.7 |
| R-33 | (A-9) | 94.15 | (B-40) | 5.72 | (C-11) | 0.12 | W-1 | S-1 | 40 | S-4 | 20 | S-5 | 40 | 3.3 |

TABLE 2-continued

| Resist compo-sition | Resin (A) Com-pound | Content (% by mass) | Acid generator (B) Com-pound | Content (% by mass) | Acid diffusion control agent Com-pound | Content (% by mass) | Surfactant Type (0.01% by mass) | Solvent 1 | Content ratio of solvent 1 (% by mass) | Sol-vent 2 | Content ratio of solvent 2 (% by mass) | Sol-vent 3 | Content ratio of solvent 3 (% by mass) | Solid content (% by mass) |
|---|---|---|---|---|---|---|---|---|---|---|---|---|---|---|
| R-34 | (A-4) | 94.06 | (B-68) | 5.78 | (C-2) | 0.16 | — | S-1 | 40 | S-2 | 40 | S-3 | 20 | 3.3 |
| R-35 | (A-9) | 91.72 | (B-77) | 8.13 | (C-14) | 0.14 | W-2 | S-1 | 60 | S-2 | 30 | S-6 | 10 | 3.3 |
| R-36 | (A-15) | 90.96 | (B-72) | 8.85 | (C-6) | 0.19 | — | S-1 | 90 | S-2 | 10 | — | — | 2.7 |
| R-37 | (A-6) | 91.63 | (B-12) | 8.23 | (C-1) | 0.14 | — | S-1 | 60 | S-2 | 40 | — | — | 2.9 |
| R-38 | (A-20) | 91.63 | (B-20) | 8.19 | (C-14) | 0.17 | W-3 | S-1 | 20 | S-2 | 60 | S-3 | 20 | 2.7 |
| R-39 | (A-7) | 93.80 | (B-46) | 6.04 | (C-10) | 0.15 | W-4 | S-1 | 80 | S-2 | 10 | S-3 | 10 | 2.9 |
| R-40 | (A-28) | 89.52 | (B-23) | 10.35 | (C-9) | 0.12 | W-1 | S-1 | 80 | S-3 | 20 | — | — | 3.3 |
| R-41 | (A-21) | 86.55 | (B-57) | 13.33 | (C-5) | 0.12 | — | S-1 | 90 | S-2 | 10 | — | — | 2.7 |
| R-42 | (A-16) | 91.00 | (B-53) | 8.83 | (C-7) | 0.16 | W-1 | S-1 | 60 | S-2 | 30 | S-3 | 10 | 2.6 |
| R-43 | (A-26) | 90.94 | (B-78) | 8.94 | (C-13) | 0.12 | — | S-1 | 40 | S-3 | 30 | S-4 | 30 | 2.9 |
| R-44 | (A-25) | 92.26 | (B-39) | 7.63 | (C-13) | 0.11 | — | S-1 | 20 | S-2 | 50 | S-3 | 30 | 3.1 |
| R-45 | (A-10) | 87.44 | (B-44) | 12.42 | (C-12) | 0.13 | W-1 | S-1 | 30 | S-2 | 60 | S-3 | 10 | 3.0 |
| R-46 | (A-31) | 88.52 | (B-65) | 11.29 | (C-4) | 0.18 | W-3 | S-1 | 30 | S-3 | 70 | — | — | 2.7 |
| R-47 | (A-22) | 89.96 | (B-64) | 9.94 | (C-9) | 0.10 | — | S-1 | 60 | S-3 | 30 | S-4 | 10 | 3.5 |
| R-48 | (A-2) | 93.04 | (B-73) | 6.80 | (C-6) | 0.15 | W-2 | S-1 | 20 | S-2 | 50 | S-3 | 30 | 3.1 |
| R-49 | (A-20) | 89.57 | (B-79) | 10.30 | (C-12) | 0.13 | — | S-1 | 20 | S-2 | 30 | S-4 | 50 | 3.4 |
| R-50 | (A-5) | 90.23 | (B-54) | 9.65 | (C-12) | 0.11 | W-1 | S-1 | 60 | S-2 | 30 | S-4 | 10 | 2.9 |
| R-51 | (A-18) | 85.89 | (B-35) | 13.92 | (C-4) | 0.18 | W-4 | S-1 | 80 | S-4 | 10 | S-5 | 10 | 3.4 |
| R-52 | (A-14) | 85.32 | (B-11) | 14.53 | (C-11) | 0.15 | — | S-1 | 60 | S-2 | 40 | — | — | 2.9 |
| R-53 | (A-23) | 87.23 | (B-5) | 12.66 | (C-5) | 0.11 | — | S-1 | 60 | S-2 | 30 | S-3 | 10 | 3.3 |
| R-54 | (A-30) | 93.60 | (B-41) | 6.20 | (C-5) | 0.20 | — | S-1 | 60 | S-2 | 40 | — | — | 3.2 |
| R-55 | (A-28) | 89.55 | (B-74) | 10.26 | (C-4) | 0.18 | W-1 | S-1 | 80 | S-3 | 20 | — | — | 3.0 |
| R-56 | (A-12) | 89.11 | (B-26) | 10.69 | (C-7) | 0.20 | — | S-1 | 90 | S-2 | 10 | — | — | 3.0 |
| R-57 | (A-11) | 85.33 | (B-30) | 14.47 | (C-1) | 0.20 | — | S-1 | 40 | S-2 | 40 | S-3 | 20 | 3.0 |
| R-58 | (A-15) | 93.38 | (B-75) | 6.47 | (C-3) | 0.14 | W-2 | S-1 | 60 | S-2 | 30 | S-3 | 10 | 3.4 |
| R-59 | (A-34) | 94.26 | (B-32) | 5.62 | (C-7) | 0.11 | W-2 | S-1 | 20 | S-2 | 60 | S-3 | 20 | 3.0 |
| R-60 | (A-2) | 92.59 | (B-16) | 7.30 | (C-8) | 0.10 | W-3 | S-1 | 40 | S-2 | 50 | S-3 | 10 | 3.3 |
| R-61 | (A-4) | 91.95 | (B-34) | 7.91 | (C-6) | 0.13 | W-1 | S-1 | 80 | S-2 | 20 | — | — | 3.2 |
| R-62 | (A-25) | 90.04 | (B-22) | 9.77 | (C-5) | 0.19 | — | S-1 | 20 | S-3 | 80 | — | — | 3.1 |
| R-63 | (A-32) | 92.14 | (B-49) | 7.70 | (C-6) | 0.16 | — | S-1 | 30 | S-2 | 30 | S-3 | 40 | 3.1 |
| R-64 | (A-26) | 93.64 | (B-17) | 6.17 | (C-10) | 0.18 | W-4 | S-1 | 80 | S-2 | 10 | S-3 | 10 | 2.8 |
| R-65 | (A-12) | 90.45 | (B-27) | 9.40 | (C-1) | 0.15 | — | S-1 | 80 | S-2 | 20 | — | — | 3.3 |
| R-66 | (A-5) | 89.11 | (B-19) | 10.78 | (C-2) | 0.11 | — | S-1 | 40 | S-4 | 40 | S-5 | 20 | 3.1 |
| R-67 | (A-4) | 93.07 | (B-62) | 6.75 | (C-2) | 0.17 | W-2 | S-1 | 30 | S-4 | 60 | S-5 | 10 | 2.9 |
| R-68 | (A-15) | 91.96 | (B-2) | 7.87 | (C-6) | 0.16 | W-3 | S-1 | 40 | S-3 | 60 | — | — | 3.3 |
| R-69 | (A-16) | 90.17 | (B-37) | 9.73 | (C-8) | 0.10 | — | S-1 | 20 | S-2 | 80 | — | — | 3.2 |
| R-70 | (A-17) | 90.35 | (B-50) | 9.45 | (C-12) | 0.19 | W-1 | S-1 | 40 | S-2 | 50 | S-3 | 10 | 2.9 |
| R-71 | (A-1) | 88.33 | (B-36) | 11.51 | (C-14) | 0.16 | — | S-1 | 20 | S-3 | 60 | S-4 | 20 | 3.4 |
| R-72 | (A-22) | 90.34 | (B-38) | 9.49 | (C-3) | 0.16 | W-4 | S-1 | 60 | S-2 | 30 | S-3 | 10 | 3.3 |
| R-73 | (A-13) | 92.71 | (B-33) | 7.17 | (C-13) | 0.12 | — | S-1 | 30 | S-2 | 20 | S-3 | 50 | 3.4 |
| R-74 | (A-1) | 91.62 | (B-47) | 8.21 | (C-14) | 0.16 | W-2 | S-1 | 60 | S-2 | 10 | S-3 | 30 | 3.1 |
| R-75 | (A-16) | 88.11 | (B-18) | 11.70 | (C-10) | 0.19 | — | S-1 | 80 | S-2 | 10 | S-3 | 10 | 3.2 |
| R-76 | (A-3) | 87.36 | (B-60) | 12.45 | (C-4) | 0.18 | W-1 | S-1 | 60 | S-2 | 30 | S-3 | 10 | 3.4 |
| R-77 | (A-33) | 93.00 | (B-63) | 6.83 | (C-1) | 0.16 | W-1 | S-1 | 20 | S-3 | 60 | S-4 | 20 | 3.3 |
| R-78 | (A-29) | 88.39 | (B-24) | 11.44 | (C-9) | 0.16 | W-3 | S-1 | 30 | S-2 | 30 | S-3 | 40 | 2.6 |
| R-79 | (A-8) | 86.97 | (B-80) | 12.92 | (C-12) | 0.11 | — | S-1 | 20 | S-2 | 80 | — | — | 2.9 |
| R-80 | (A-27) | 93.73 | (B-8) | 6.14 | (C-10) | 0.12 | W-2 | S-1 | 40 | S-2 | 40 | S-3 | 20 | 3.3 |
| R-81 | (A-4) | 89.64 | (B-43) | 10.20 | (C-2) | 0.15 | W-4 | S-1 | 20 | S-2 | 80 | — | — | 3.0 |
| R-82 | (A-29) | 88.83 | (B-21) | 11.00 | (C-2) | 0.16 | W-1 | S-1 | 60 | S-2 | 30 | S-4 | 10 | 3.0 |
| R-83 | (A-10) | 89.61 | (B-28) | 10.22 | (C-4) | 0.17 | — | S-1 | 80 | S-2 | 10 | S-3 | 10 | 3.3 |
| R-84 | (A-13) | 85.11 | (B-66) | 14.79 | (C-11) | 0.10 | — | S-1 | 80 | S-3 | 10 | S-4 | 10 | 3.3 |
| R-85 | (A-19) | 93.06 | (B-13) | 6.80 | (C-1) | 0.13 | W-2 | S-1 | 40 | S-3 | 50 | S-4 | 10 | 3.2 |
| R-86 | (A-4) | 90.29 | (B-76) | 9.52 | (C-2) | 0.19 | — | S-1 | 60 | S-2 | 20 | S-3 | 20 | 2.9 |
| R-87 | (A-19) | 84.96 | (B-29) | 14.93 | (C-5) | 0.11 | — | S-1 | 30 | S-2 | 20 | S-4 | 50 | 3.2 |
| R-88 | (A-6) | 85.04 | (B-45) | 14.75 | (C-7) | 0.20 | W-1 | S-1 | 60 | S-4 | 30 | S-5 | 10 | 3.3 |
| R-89 | (A-30) | 85.86 | (B-56) | 13.99 | (C-2) | 0.14 | W-3 | S-1 | 40 | S-3 | 50 | S-6 | 10 | 3.3 |
| R-90 | (A-3) | 85.02 | (B-51) | 14.83 | (C-5) | 0.14 | W-4 | S-1 | 60 | S-3 | 20 | S-6 | 20 | 3.1 |
| R-91 | (A-4) | 87.95 | (B-67) | 11.87 | (C-5) | 0.17 | W-1 | S-1 | 60 | S-3 | 10 | S-5 | 30 | 3.3 |
| R-92 | (A-31) | 86.74 | (B-25) | 13.10 | (C-8) | 0.15 | W-2 | S-1 | 60 | S-3 | 10 | S-5 | 30 | 2.9 |
| R-93 | (A-14) | 93.71 | (B-58) | 6.13 | (C-11) | 0.15 | W-1 | S-1 | 60 | S-2 | 30 | S-4 | 10 | 3.0 |
| R-94 | (A-5) | 90.34 | (B-69) | 9.56 | (C-3) | 0.10 | — | S-1 | 40 | S-3 | 50 | S-6 | 10 | 3.3 |
| R-95 | (A-24) | 92.35 | (B-71) | 7.50 | (C-3) | 0.15 | — | S-1 | 20 | S-2 | 50 | S-3 | 30 | 3.1 |
| R-96 | (A-4) | 94.36 | (B-52) | 5.52 | (C-13) | 0.11 | W-1 | S-1 | 40 | S-3 | 30 | S-6 | 30 | 2.9 |
| R-97 | (A-17) | 90.10 | (B-55) | 9.70 | (C-13) | 0.19 | W-1 | S-1 | 40 | S-3 | 20 | S-4 | 40 | 3.0 |
| R-98 | (A-18) | 93.22 | (B-48) | 6.59 | (C-10) | 0.18 | W-3 | S-1 | 60 | S-2 | 40 | — | — | 2.7 |
| R-99 | (A-15) | 94.24 | (B-61) | 5.61 | (C-5) | 0.15 | — | S-1 | 20 | S-3 | 80 | — | — | 2.9 |
| R-100 | (A-32) | 92.72 | (B-42) | 7.10 | (C-1) | 0.18 | — | S-1 | 20 | S-2 | 60 | S-5 | 20 | 2.7 |
| R-101 | (A-4) | 87.32 | (B-31) | 12.52 | (C-11) | 0.15 | W-1 | S-1 | 40 | S-2 | 50 | S-3 | 10 | 3.2 |
| R-102 | (A-24) | 90.56 | (B-70) | 9.33 | (C-3) | 0.10 | W-4 | S-1 | 20 | S-2 | 50 | S-3 | 30 | 2.9 |
| R-103 | (A-27) | 85.27 | (B-59) | 14.60 | (C-8) | 0.13 | — | S-1 | 80 | S-2 | 20 | — | — | 2.5 |

TABLE 3

| | Resist composition | LS resolution [nm] | Isolated space pattern resolution [nm] | Development defects |
|---|---|---|---|---|
| Example 1a | R-1 | 22 | 23 | B |
| Example 2a | R-2 | 24 | 23 | A |
| Example 3a | R-3 | 22 | 21 | B |
| Example 4a | R-4 | 23 | 23 | A |
| Example 5a | R-5 | 21 | 20 | A |
| Example 6a | R-6 | 24 | 23 | A |
| Example 7a | R-7 | 24 | 22 | A |
| Example 8a | R-8 | 26 | 25 | A |
| Example 9a | R-9 | 27 | 25 | A |
| Example 10a | R-10 | 25 | 23 | A |
| Example 11a | R-11 | 23 | 22 | A |
| Example 12a | R-12 | 22 | 23 | A |
| Example 13a | R-13 | 23 | 20 | A |
| Example 14a | R-14 | 22 | 23 | B |
| Example 15a | R-15 | 21 | 21 | A |
| Example 16a | R-16 | 25 | 25 | A |
| Example 17a | R-17 | 26 | 24 | A |
| Example 18a | R-18 | 22 | 20 | B |
| Comparative Example 1a | R-19 | 25 | 23 | D |
| Comparative Example 2a | R-20 | 27 | 25 | D |
| Comparative Example 3a | R-21 | 40 | 38 | B |
| Example 19a | R-22 | 23 | 22 | B |
| Example 20a | R-23 | 25 | 23 | A |
| Example 21a | R-24 | 24 | 24 | B |
| Example 22a | R-25 | 25 | 23 | A |
| Example 23a | R-26 | 23 | 22 | A |
| Example 24a | R-27 | 21 | 20 | A |
| Example 25a | R-28 | 26 | 21 | A |
| Example 26a | R-29 | 28 | 25 | A |
| Example 27a | R-30 | 25 | 26 | A |
| Example 28a | R-31 | 22 | 20 | A |
| Example 29a | R-32 | 23 | 22 | A |
| Example 30a | R-33 | 22 | 22 | A |
| Example 31a | R-34 | 20 | 22 | A |
| Example 32a | R-35 | 23 | 21 | A |
| Example 33a | R-36 | 23 | 21 | A |
| Example 34a | R-37 | 21 | 20 | A |
| Example 35a | R-38 | 22 | 25 | A |
| Example 36a | R-39 | 26 | 22 | B |
| Example 37a | R-40 | 23 | 24 | A |
| Example 38a | R-41 | 25 | 21 | A |
| Example 39a | R-42 | 21 | 20 | A |
| Example 40a | R-43 | 25 | 26 | A |
| Example 41a | R-44 | 27 | 23 | A |
| Example 42a | R-45 | 23 | 21 | A |
| Example 43a | R-46 | 21 | 20 | A |
| Example 44a | R-47 | 25 | 22 | A |
| Example 45a | R-48 | 25 | 26 | A |
| Example 46a | R-49 | 23 | 24 | A |
| Example 47a | R-50 | 25 | 26 | A |
| Example 48a | R-51 | 25 | 21 | A |
| Example 49a | R-52 | 25 | 22 | A |
| Example 50a | R-53 | 24 | 21 | A |
| Example 51a | R-54 | 25 | 24 | A |
| Example 52a | R-55 | 22 | 20 | A |
| Example 53a | R-56 | 21 | 21 | A |
| Example 54a | R-57 | 25 | 24 | A |
| Example 55a | R-58 | 22 | 23 | A |
| Example 56a | R-59 | 27 | 24 | A |
| Example 57a | R-60 | 24 | 21 | A |
| Example 58a | R-61 | 23 | 21 | A |
| Example 59a | R-62 | 23 | 21 | A |
| Example 60a | R-63 | 23 | 25 | B |
| Example 61a | R-64 | 25 | 23 | A |
| Example 62a | R-65 | 22 | 21 | A |
| Example 63a | R-66 | 25 | 24 | A |
| Example 64a | R-67 | 20 | 20 | A |
| Example 65a | R-68 | 27 | 22 | A |
| Example 66a | R-69 | 25 | 25 | A |
| Example 67a | R-70 | 24 | 24 | A |
| Example 68a | R-71 | 22 | 22 | A |
| Example 69a | R-72 | 25 | 24 | A |
| Example 70a | R-73 | 23 | 25 | A |
| Example 71a | R-74 | 24 | 21 | A |
| Example 72a | R-75 | 23 | 24 | A |
| Example 73a | R-76 | 23 | 21 | A |
| Example 74a | R-77 | 25 | 26 | A |
| Example 75a | R-78 | 22 | 24 | A |
| Example 76a | R-79 | 21 | 23 | A |
| Example 77a | R-80 | 25 | 23 | A |
| Example 78a | R-81 | 22 | 21 | A |
| Example 79a | R-82 | 26 | 25 | A |
| Example 80a | R-83 | 26 | 21 | A |
| Example 81a | R-84 | 26 | 25 | A |
| Example 82a | R-85 | 24 | 23 | A |
| Example 83a | R-86 | 22 | 23 | A |
| Example 84a | R-87 | 25 | 24 | A |
| Example 85a | R-88 | 26 | 25 | A |
| Example 86a | R-89 | 24 | 20 | A |
| Example 87a | R-90 | 26 | 22 | A |
| Example 88a | R-91 | 21 | 20 | A |
| Example 89a | R-92 | 24 | 23 | A |
| Example 90a | R-93 | 27 | 23 | B |
| Example 91a | R-94 | 24 | 24 | A |
| Example 92a | R-95 | 23 | 22 | A |
| Example 93a | R-96 | 22 | 24 | A |
| Example 94a | R-97 | 23 | 20 | A |
| Example 95a | R-98 | 23 | 23 | A |
| Example 96a | R-99 | 22 | 24 | A |
| Example 97a | R-100 | 25 | 21 | A |
| Example 98a | R-101 | 23 | 24 | A |
| Example 99a | R-102 | 26 | 20 | A |
| Example 100a | R-103 | 23 | 22 | A |

From the results in Table 3, it can be seen that a pattern obtained by the pattern forming method of the present invention has excellent resolution and suppressed development defects.

[Extreme Ultraviolet Ray (EUV) Exposure]

(4) Preparation of Resist Pattern

A wafer on which the resist film obtained in (3) had been applied was subjected to patternwise exposure through an exposure mask (line/space=1/1) using an EUV exposure apparatus (Micro Exposure Tool, manufactured by Exitech, numerical aperture (NA): 0.3, Quadrupole, outer sigma: 0.68, inner sigma: 0.36). After the exposure, the film was heated on a hot plate at 100° C. for 90 seconds, dipped using a 2.38%-by-mass aqueous tetramethylammonium hydroxide (TMAH) solution for 60 seconds, and then rinsed with water for 30 seconds. Then, the wafer was rotated at a rotation speed of 4,000 rpm for 30 seconds, baked at 95° C. for 60 seconds, and dried.

[Evaluation]

(5) Evaluation of Resist Pattern

The obtained pattern was evaluated on resolution and development defects by the following methods. The results are shown in Table 4 below.

The irradiation energy upon resolution of a 1:1 line-and-space pattern with a line width of 50 nm was defined as a sensitivity (Eop).

<L/S Resolution>

A marginal resolving power (a minimum line width at which lines and spaces (line:space=1:1) are separated and resolved) at an exposure dose showing the sensitivity (Eop) was taken as a resolving power (nm).

<Isolated Space Pattern (IS) Resolution>

A marginal resolving power (a minimum space width at which lines and spaces are separated and resolved) of an isolated space (line:space=100:1) at the sensitivity (Eop)

was determined. Then, this value was defined as an "isolated space pattern resolving power (nm)". A smaller value thereof indicates better performance.

<Development Defects>

Using a defect inspection apparatus, KLA 2360 (trade name), manufactured by KLA Tencor Ltd., a 1:1 line-and-space pattern with a line width of 50 nm formed at the sensitivity (Eop) was measured by setting a pixel size of the defect inspection apparatus to 0.16 µm and a threshold value to 20 to detect defects (defects/cm$^2$) extracted from a difference produced at the time of superposing pixel units on a reference image, and the number of the defects per unit area (defects/cm$^2$) was computed. Then, by performing a defect review, the development defects were classified and extracted from all the defects, and the number of development defects per unit area (defects/cm$^2$) was computed. The value of less than 0.5 was designated as A, the value of 0.5 or more and less than 1.0 was designated as B, the value of 1.0 or more and less than 5.0 was designated as C, and a value of 5.0 or more was designated as D. A smaller value thereof indicates better performance.

TABLE 4

| | Resist composition | LS resolution [nm] | Isolated space pattern resolution [nm] | Development defects |
|---|---|---|---|---|
| Example 1b | R-1 | 21 | 22 | B |
| Example 2b | R-2 | 24 | 23 | A |
| Example 3b | R-3 | 22 | 21 | B |
| Example 4b | R-4 | 23 | 23 | A |
| Example 5b | R-5 | 21 | 20 | A |
| Example 6b | R-6 | 24 | 23 | A |
| Example 7b | R-7 | 24 | 22 | A |
| Example 8b | R-8 | 25 | 25 | A |
| Example 9b | R-9 | 27 | 24 | A |
| Example 10b | R-10 | 22 | 23 | A |
| Example 11b | R-11 | 23 | 22 | A |
| Example 12b | R-12 | 22 | 21 | A |
| Example 13b | R-13 | 23 | 22 | A |
| Example 14b | R-14 | 23 | 23 | B |
| Example 15b | R-15 | 21 | 21 | A |
| Example 16b | R-16 | 25 | 25 | A |
| Example 17b | R-17 | 26 | 24 | A |
| Example 18b | R-18 | 22 | 20 | B |
| Comparative Example 1b | R-19 | 25 | 24 | D |
| Comparative Example 2b | R-20 | 27 | 26 | D |
| Comparative Example 3b | R-21 | 42 | 38 | B |
| Example 19b | R-22 | 27 | 23 | B |
| Example 20b | R-23 | 23 | 23 | A |
| Example 21b | R-24 | 25 | 24 | B |
| Example 22b | R-25 | 26 | 23 | A |
| Example 23b | R-26 | 20 | 19 | A |
| Example 24b | R-27 | 24 | 22 | A |
| Example 25b | R-28 | 23 | 23 | A |
| Example 26b | R-29 | 27 | 26 | A |
| Example 27b | R-30 | 26 | 23 | A |
| Example 28b | R-31 | 22 | 22 | A |
| Example 29b | R-32 | 24 | 25 | A |
| Example 30b | R-33 | 24 | 24 | A |
| Example 31b | R-34 | 23 | 24 | A |
| Example 32b | R-35 | 24 | 26 | A |
| Example 33b | R-36 | 23 | 21 | A |
| Example 34b | R-37 | 24 | 20 | A |
| Example 35b | R-38 | 24 | 25 | A |
| Example 36b | R-39 | 24 | 20 | B |
| Example 37b | R-40 | 23 | 21 | A |
| Example 38b | R-41 | 22 | 25 | A |
| Example 39b | R-42 | 23 | 22 | A |
| Example 40b | R-43 | 23 | 24 | A |
| Example 41b | R-44 | 22 | 26 | A |
| Example 42b | R-45 | 26 | 26 | A |
| Example 43b | R-46 | 25 | 21 | A |
| Example 44b | R-47 | 22 | 24 | A |
| Example 45b | R-48 | 24 | 26 | A |
| Example 46b | R-49 | 22 | 25 | A |
| Example 47b | R-50 | 22 | 24 | B |
| Example 48b | R-51 | 27 | 22 | A |
| Example 49b | R-52 | 27 | 22 | A |
| Example 50b | R-53 | 24 | 24 | A |
| Example 51b | R-54 | 25 | 24 | A |
| Example 52b | R-55 | 23 | 26 | A |
| Example 53b | R-56 | 24 | 25 | B |
| Example 54b | R-57 | 26 | 21 | A |
| Example 55b | R-58 | 22 | 21 | A |
| Example 56b | R-59 | 27 | 26 | A |
| Example 57b | R-60 | 24 | 21 | A |
| Example 58b | R-61 | 24 | 23 | A |
| Example 59b | R-62 | 25 | 24 | A |
| Example 60b | R-63 | 22 | 20 | A |
| Example 61b | R-64 | 24 | 22 | A |
| Example 62b | R-65 | 26 | 23 | A |
| Example 63b | R-66 | 27 | 23 | A |
| Example 64b | R-67 | 23 | 20 | A |
| Example 65b | R-68 | 23 | 22 | B |
| Example 66b | R-69 | 27 | 21 | A |
| Example 67b | R-70 | 26 | 24 | A |
| Example 68b | R-71 | 26 | 24 | A |
| Example 69b | R-72 | 26 | 23 | A |
| Example 70b | R-73 | 23 | 25 | A |
| Example 71b | R-74 | 26 | 23 | A |
| Example 72b | R-75 | 25 | 21 | A |
| Example 73b | R-76 | 22 | 23 | A |
| Example 74b | R-77 | 23 | 26 | B |
| Example 75b | R-78 | 24 | 25 | A |
| Example 76b | R-79 | 24 | 23 | A |
| Example 77b | R-80 | 25 | 24 | A |
| Example 78b | R-81 | 23 | 22 | A |
| Example 79b | R-82 | 25 | 22 | A |
| Example 80b | R-83 | 22 | 25 | A |
| Example 81b | R-84 | 23 | 26 | A |
| Example 82b | R-85 | 25 | 24 | A |
| Example 83b | R-86 | 24 | 22 | A |
| Example 84b | R-87 | 26 | 21 | A |
| Example 85b | R-88 | 23 | 21 | A |
| Example 86b | R-89 | 25 | 24 | A |
| Example 87b | R-90 | 26 | 24 | A |
| Example 88b | R-91 | 21 | 20 | A |
| Example 89b | R-92 | 27 | 21 | A |
| Example 90b | R-93 | 24 | 24 | A |
| Example 91b | R-94 | 23 | 23 | A |
| Example 92b | R-95 | 24 | 21 | B |
| Example 93b | R-96 | 22 | 20 | A |
| Example 94b | R-97 | 23 | 25 | A |
| Example 95b | R-98 | 26 | 24 | A |
| Example 96b | R-99 | 27 | 20 | A |
| Example 97b | R-100 | 26 | 22 | A |
| Example 98b | R-101 | 22 | 21 | A |
| Example 99b | R-102 | 26 | 26 | B |
| Example 100b | R-103 | 23 | 25 | A |

From the results in Table 4, it can be seen that the pattern obtained by the pattern forming method of the present invention has excellent resolution and suppressed development defects.

According to the present invention, it is possible to provide an actinic ray-sensitive or radiation-sensitive resin composition which can attain both an improvement of a resolving power and a reduction in development defects at a high level. According to the present invention, it is possible to provide an actinic ray-sensitive or radiation-sensitive film using the actinic ray-sensitive or radiation-sensitive resin composition, a pattern forming method, a method for manufacturing an electronic device, and a compound.

Although the present invention has been described in detail and with reference to specific embodiments, it will be apparent to those skilled in the art that various changes and modifications can be made without departing from the spirit and the scope of the invention.

What is claimed is:

1. An actinic ray-sensitive or radiation-sensitive resin composition comprising the following (A) and (B):
   (A) a resin having a solubility in an alkali developer that increases through decomposition by an action of an acid; and
   (B) a compound that generates an acid upon irradiation with actinic rays or radiation and is represented by General Formula (1),

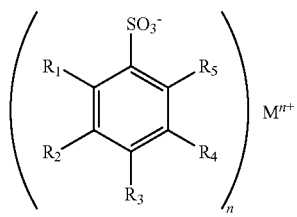

in General Formula (1), $R_1$ and $R_5$ each independently represent an aryl group or a heteroaryl group, $R_2$ to $R_4$ each independently represent a hydrogen atom or a substituent, $M^{n+}$ represents a cation, and n represents an integer of 1 or more;
wherein the content of the resin (A) in the actinic ray-sensitive or radiation-sensitive resin composition is 20 to 99.5 mass % and the content of the compound (B) in the actinic ray-sensitive or radiation-sensitive resin composition is 0.1 to 35 mass %, with respect to the total solids content of the composition; and wherein the actinic ray-sensitive or radiation-sensitive resin composition does not include a compound which generates an acid with a pKa lower than the acid generated by the compound (B).

2. The actinic ray-sensitive or radiation-sensitive resin composition according to claim 1,
wherein in General Formula (1), $R_3$ represents an aryl group.

3. The actinic ray-sensitive or radiation-sensitive resin composition according to claim 1,
wherein in General Formula (1), at least one of $R_1$, $R_2$, $R_3$, $R_4$, or $R_5$ is a group including a polar group, a group including a group having a polarity that increases through decomposition by an action of an acid, or a group including a group having a solubility in an alkali developer that increases through decomposition by an action of an alkali developer.

4. The actinic ray-sensitive or radiation-sensitive resin composition according to claim 1,
wherein in General Formula (1), $R_1$, $R_3$, and $R_5$ are each a group represented by General Formula (Ar),

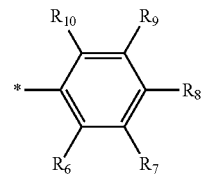

in General Formula (Ar), $R_6$ to $R_{10}$ each independently represent a hydrogen atom or a substituent, at least one of $R_6$, $R_7$, $R_8$, $R_9$, or $R_{10}$ is a group including a polar group, a group including a group having a polarity that increases through decomposition by an action of an acid, or a group including a group having a solubility in an alkali developer that increases through decomposition by an action of an alkali developer, and * represents a bond to a benzene ring in General Formula (1).

5. The actinic ray-sensitive or radiation-sensitive resin composition according to claim 1,
wherein in General Formula (1), $R_1$, $R_3$, and $R_5$ are each a group represented by General Formula (Ar1),

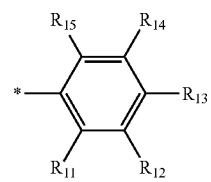

in General Formula (Ar1), $R_{11}$ to $R_{15}$ each independently represent a hydrogen atom or a substituent, at least one of $R_{11}$, $R_{12}$, $R_{13}$, $R_{14}$, or $R_{15}$ represents the following substituent Y, and * represents a bond to a benzene ring in General Formula (1),
Substituent Y: a hydroxyl group, a carboxyl group, a group having a carbonyl bond, an acyloxy group, an alkoxycarbonyloxy group, an aryloxycarbonyloxy group, an aryloxycarbonyl group, an alkoxycarbonyl group, a carbamoyl group, or an imido group.

6. The actinic ray-sensitive or radiation-sensitive resin composition according to claim 1,
wherein a pKa of an acid generated from the compound (B) upon irradiation with actinic rays or radiation is −10 to 5.

7. An actinic ray-sensitive or radiation-sensitive film formed of the actinic ray-sensitive or radiation-sensitive resin composition according to claim 1.

8. A pattern forming method comprising:
a resist film forming step of forming a resist film using the actinic ray-sensitive or radiation-sensitive resin composition according to claim 1;
an exposing step of exposing the resist film; and
a developing step of developing the exposed resist film using a developer.

9. A method for manufacturing an electronic device, comprising the pattern forming method according to claim 8.

* * * * *